(12) United States Patent
Murray et al.

(10) Patent No.: US 11,717,350 B2
(45) Date of Patent: Aug. 8, 2023

(54) METHODS FOR ROBOTIC ASSISTANCE AND NAVIGATION IN SPINAL SURGERY AND RELATED SYSTEMS

(71) Applicant: GLOBUS MEDICAL, INC., Audubon, PA (US)

(72) Inventors: Patrick Murray, Collegeville, PA (US); David Left, Philadelphia, PA (US); Albert Hill, Richboro, PA (US); John LaColla, West Chester, PA (US); Shruthi Muralidharan, King of Prussia, PA (US); Jeff Nichols, Media, PA (US)

(73) Assignee: Globus Medical Inc., Audubon, PA (US)

( * ) Notice: Subject to any disclaimer, the term of this patent is extended or adjusted under 35 U.S.C. 154(b) by 316 days.

(21) Appl. No.: 17/103,306

(22) Filed: Nov. 24, 2020

(65) Prior Publication Data
US 2022/0160428 A1    May 26, 2022

(51) Int. Cl.
*A61B 34/10*    (2016.01)
*A61B 34/30*    (2016.01)
(Continued)

(52) U.S. Cl.
CPC .......... *A61B 34/10* (2016.02); *A61B 17/7086* (2013.01); *A61B 34/30* (2016.02); *G16H 20/40* (2018.01); *G16H 30/20* (2018.01); *A61B 17/7001* (2013.01); *A61B 2017/00119* (2013.01); *A61B 2017/564* (2013.01); *A61B 2017/681* (2013.01); *A61B 2034/104* (2016.02);
(Continued)

(58) Field of Classification Search
CPC ......... A61B 34/10; A61B 34/30; A61B 34/70; A61B 34/7086; G16H 20/40; G16H 30/20
See application file for complete search history.

(56) References Cited

U.S. PATENT DOCUMENTS

| 4,150,293 | A | 4/1979 | Franke |
| 5,246,010 | A | 9/1993 | Gazzara et al. |
| (Continued) | | | |

OTHER PUBLICATIONS

US 8,231,638 B2, 07/2012, Swarup et al. (withdrawn)

*Primary Examiner* — Christopher J Beccia

(57) ABSTRACT

A surgical navigation system is provided to create a plan to correct a deformed spinal alignment. A processor is configured to obtain a first set of image data associated with a deformed alignment in a spine of a patient from at least one imaging device. The processor is also configured to process the first set of image data to identify a set of deformed alignment parameters associated with the deformed alignment. The processor is further configured to identify a set of corrected alignment parameters. The processor is also configured to process the first set of image data, the set of deformed alignment parameters, and the set of corrected alignment parameters to generate a correction plan to surgically manipulate the deformed alignment to the preferred alignment. The processor is additionally configured to provide navigation through the correction plan to facilitate surgical manipulation of a patient spine to the preferred alignment. The processor is also configured to receive information relating to forces on a rod-link reducer or surgical implants from strain gauges to aid the correction plan.

18 Claims, 28 Drawing Sheets

(51) Int. Cl.
*A61B 17/70* (2006.01)
*G16H 20/40* (2018.01)
*G16H 30/20* (2018.01)
*A61B 17/56* (2006.01)
*A61B 17/00* (2006.01)
*A61B 17/68* (2006.01)
*A61B 34/20* (2016.01)

(52) U.S. Cl.
CPC ............ *A61B 2034/2065* (2016.02); *A61B 2562/0261* (2013.01)

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |

(56) References Cited

U.S. PATENT DOCUMENTS

| | | |
|---|---|---|
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Winash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Willliams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 3,035,685 A1 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |

(56) References Cited

U.S. PATENT DOCUMENTS

| | | |
|---|---|---|
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Greer et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 2001/0036302 A1 | 11/2001 | Miller |
| 2002/0035321 A1 | 3/2002 | Bucholz et al. |
| 2004/0068172 A1 | 4/2004 | Nowinski et al. |

(56) References Cited

U.S. PATENT DOCUMENTS

| | | |
|---|---|---|
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | von Jako |
| 2008/0109012 A1 | 5/2008 | Falco et al. |
| 2008/0144906 A1 | 6/2008 | Allred et al. |
| 2008/0161680 A1 | 7/2008 | von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |

(56) References Cited

U.S. PATENT DOCUMENTS

| | | |
|---|---|---|
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1* | 8/2016 | Scholl ............ A61B 34/10 |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

\* cited by examiner

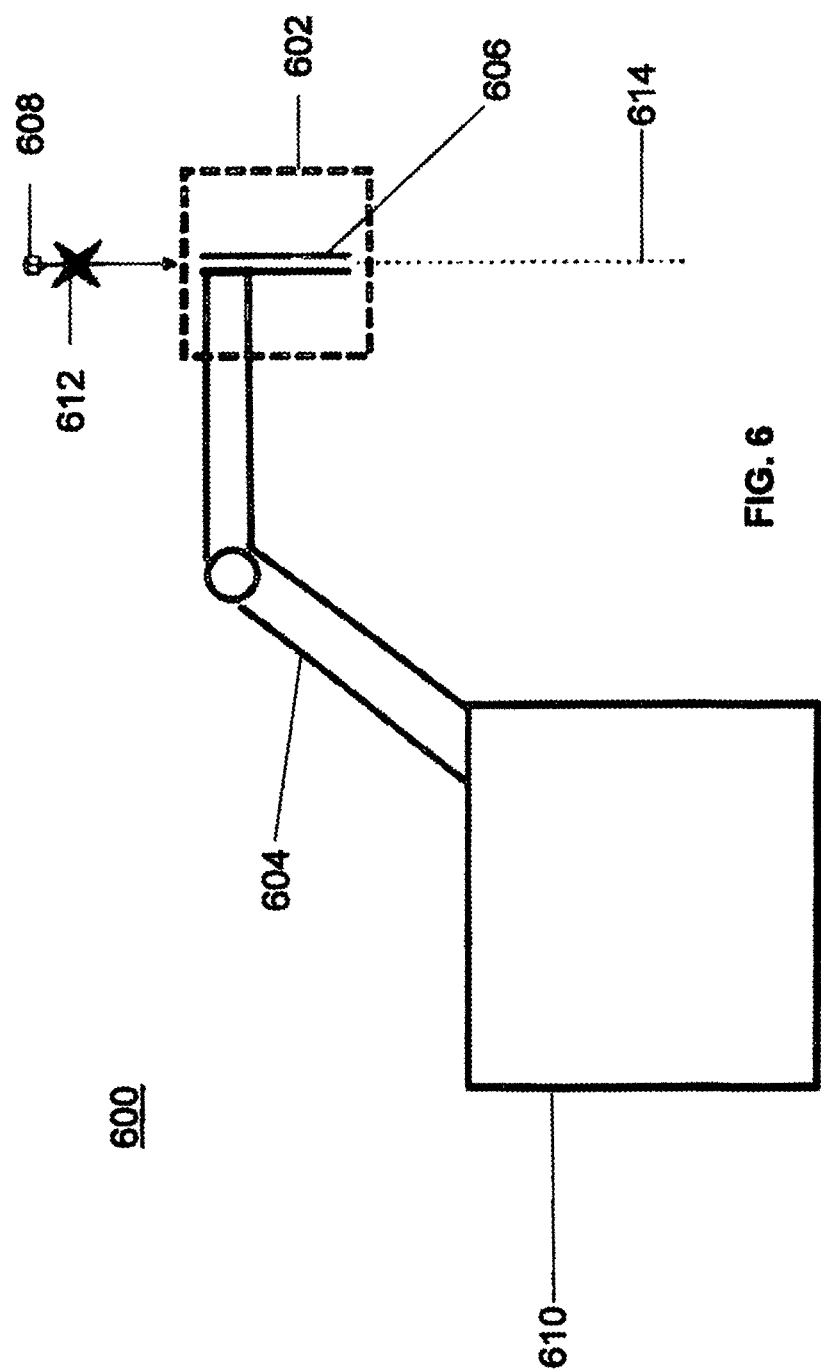

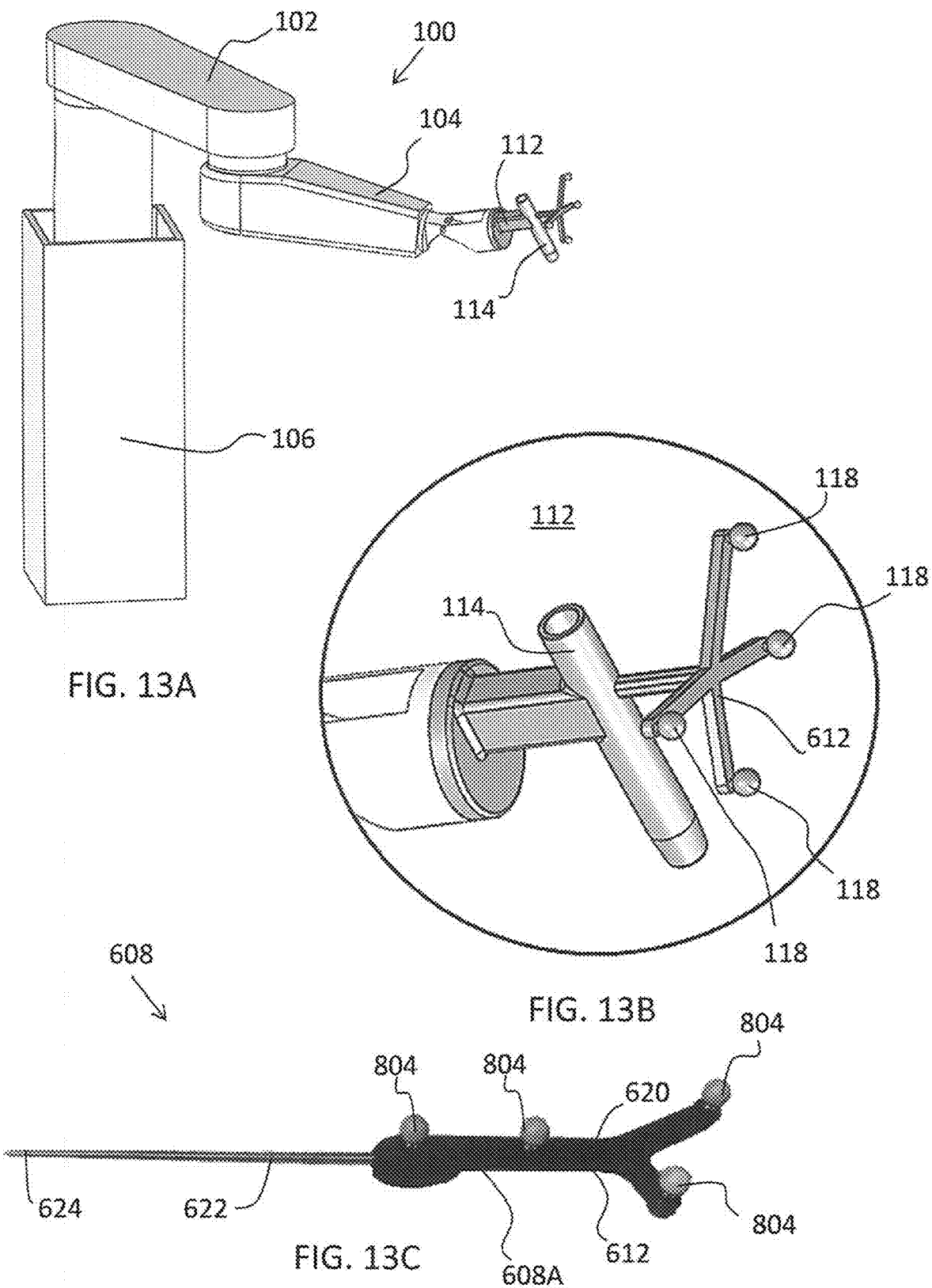

METHODS FOR ROBOTIC ASSISTANCE AND NAVIGATION IN SPINAL SURGERY AND RELATED SYSTEMS

CROSS REFERENCE TO RELATED APPLICATIONS

This application incorporates by reference U.S. patent application Ser. No. 15/157,444, filed May 18, 2016, U.S. patent application Ser. No. 15/095,883, filed Apr. 11, 2016, U.S. patent application Ser. No. 14/062,707, filed on Oct. 24, 2013, U.S. patent application Ser. No. 13/924,505, filed on Jun. 21, 2013, U.S. Provisional Application No. 61/662,702 filed on Jun. 21, 2012 and U.S. Provisional Application No. 61/800,527 filed on Mar. 15, 2013.

FIELD

The present disclosure relates to devices, systems, and methods for defining and implementing data-driven navigation during spinal surgery to correct spinal deformities, and electromechanical control of instruments during such surgery.

BACKGROUND

Typically, a healthy and normal spine is structurally balanced for optimal flexibility and support of body weight. When viewed from the side or laterally, a spine typically has three (3) mild curves. First, the lumbar (a lower portion) spine has an inward curve (relative to the body) called lordosis. Second, the thoracic (a middle portion) spine has an outward curve called normal kyphosis. Third, the cervical spine (the spine at the neck of the body) also has a lordosis curving inward. These curves collectively keep the center of gravity of the body aligned over the hips and pelvis. When viewed from behind, the normal spine is straight. Spinal deformities, by contrast, are deviations from expected or typical spinal formations. Known deformities include, for example, scoliosis (side-to-side curvature of the spine), kyphosis (distinct from normal kyphosis, this spinal deformity involves abnormally excessive convex curvature of the spine as it occurs in the thoracic and sacral regions), and lordosis (a rare spinal deformity wherein the lower back curves inwardly). Typically, spinal deformities are treated with surgical operations aimed at correcting the deformed spine to conform to a normal curvature.

In spinal surgeries, the current state-of-the-art requires surgeons to manually apply corrective forces to the grips or handles of instruments to correct spinal deformities. The corrective forces, displacement, and rotation of the spine are controlled by a surgeon based on tactile feedback and visualization of the posterior anatomical elements. Typically, after the procedure X-ray imaging is obtained and used to confirm that sufficient correction has been achieved. Further, various neurological tests may be performed to ensure that a patient is neurologically stable and that the spinal cord is functionally stable and undamaged. This approach has several significant limitations.

First, because the imaging and tests are completed only after the procedure is performed, surgeons have no access to crucial information until after the procedure. As such, the surgeon relies on tactile feedback and visual perception without the benefit of imaging or diagnostic information that can be obtained through imaging or testing. The consequence is that surgical procedures are often incomplete, performed with inadequate precision, and require further correction.

Second, because surgeons rely upon tactile perception (i.e., the physical response of the surgeon's hands to equipment used in the procedure), the procedure may be imprecise to the degree that the surgeon cannot accurately gauge the progress of the correction during the procedure, or the degree to which the procedure is following an intended course. Further, the surgeon may make judgment calls that are based on prior experience but not relevant to the particular conditions of a patient. Reliance on such prior experience may in fact lead to choices that are undesirable for a patient presenting conditions that vary from prior experiences including, for example, varying bone densities, spinal condition, or spinal form.

Third, because the surgeon manually exerts force on the equipment, the surgeon may be unable to precisely guide equipment to correct spinal deformities.

SUMMARY

As described above, the state-of-the art of spinal surgeries has several deficiencies. These deficiencies are overcome by the systems and methods described herein. The inventions described herein improve the safety, efficacy, reliability, and repeatability of correction maneuvers during deformity surgery. Utilizing technological advancements in robotics, navigation, imaging, diagnostics, and computational analysis and processing allows the systems and methods to provide surgeons with patient specific data that can be used to optimize clinical outcomes, to navigate surgical plans, and to assist directly in surgeries. The data-driven systems also provide surgeons with more information so they can make better decisions during surgery. In some embodiments, such information may also aggregated into a database and utilized to create and improve algorithms for predicting, tracking, and achieving optimal deformity correction. In sum, the systems, methods, and devices described collectively allow surgeons to raise the standard of care for patients.

Robotic technologies described herein have the ability to provide enhanced safety and improved efficiency for surgeons during deformity correction in spinal surgeries. Likewise, the use described herein of imaging and navigation technologies, combined with robotics technologies, receives real time feedback on clinically significant parameters that previously could not be assessed intraoperatively. As such, the present inventions include devices, systems, and methods of integrating robotic, imaging, and navigation technologies into spinal deformity correction procedures.

Described herein are devices, systems and methods of implementing navigation and electromechanical control of instruments for correcting a spinal deformity. These devices, systems, and methods utilize and interact with a screw system which permits transmission of corrective forces to the vertebrae during a surgical operation and, once locked to a rod, rigidly holds the spine in the corrected position as the vertebrae fuse post-operatively. In one embodiment, the screw system utilizes a pedicle-shaped screw. In other embodiments, other screw shapes, screw types, and other devices may be used.

According to one embodiment, a surgical navigation system is provided for defining and implementing a surgical navigation plan to correct a deformed spinal alignment. The surgical navigation system includes at least one imaging device configured to capture image data. The surgical navigation system also includes a surgical navigation computing device in communication with the at least one imaging device. The surgical navigation computing device includes a processor and a memory. The processor is configured to obtain a first set of image data associated with a deformed alignment in a spine of a patient from the at least one imaging device. The processor is also configured to process the first set of image data to identify a set of deformed alignment parameters associated with the deformed alignment. The processor is further configured to identify a set of corrected alignment parameters associated with a preferred alignment of the spine of the patient. The processor is also configured to process the first set of image data, the set of deformed alignment parameters, and the set of corrected alignment parameters to generate a correction plan to surgically manipulate the deformed alignment to the preferred alignment. The processor is additionally configured to provide navigation through the correction plan to facilitate surgical manipulation of a patient spine from the deformed alignment to the preferred alignment.

According to another embodiment, a method for defining and implementing a surgical navigation plan to correct a deformed spinal alignment is provided. The method is performed by a surgical navigation computing device in communication with at least one imaging device. The surgical navigation computing device includes a processor and a memory. The method includes obtaining a first set of image data associated with a deformed alignment in a spine of a patient from the at least one imaging device. The method also includes processing the first set of image data to identify a set of deformed alignment parameters associated with the deformed alignment. The method further includes identifying a set of corrected alignment parameters associated with a preferred alignment of the spine of the patient. The method additionally includes processing the first set of image data, the set of deformed alignment parameters, and the set of corrected alignment parameters to generate a correction plan to surgically manipulate the deformed alignment to the preferred alignment. The method also includes providing navigation through the correction plan to facilitate surgical manipulation of a patient spine from the deformed alignment to the preferred alignment.

A surgical navigation computing device is provided for defining and implementing a surgical navigation plan to correct a deformed spinal alignment. The surgical navigation computing device is in communication with at least one imaging device. The surgical navigation computing device includes a processor and a memory. The processor is configured to obtain a first set of image data associated with a deformed alignment in a spine of a patient from the at least one imaging device. The processor is also configured to process the first set of image data to identify a set of deformed alignment parameters associated with the deformed alignment. The processor is further configured to identify a set of corrected alignment parameters associated with a preferred alignment of the spine of the patient. The processor is also configured to process the first set of image data, the set of deformed alignment parameters, and the set of corrected alignment parameters to generate a correction plan to surgically manipulate the deformed alignment to the preferred alignment. The processor is additionally configured to provide navigation through the correction plan to facilitate surgical manipulation of a patient spine from the deformed alignment to the preferred alignment.

As described herein, in some embodiments, the surgical navigation computing device, the surgical navigation system, and the methods described interact with surgical robots to implement the defined surgical navigation plans to correct a deformed spinal alignment. As such, in some embodiments, the systems and methods described utilize certain surgical robots. According to one embodiment, a surgical robot system includes a robot having a robot base and a display, a robot arm coupled to the robot base, and an end-effector coupled to the robot arm, the end-effector having one or more tracking markers, wherein movement of the end-effector is electronically controlled by the robot. The system further includes a camera stand including at least one camera able to detect the one or more tracking markers, wherein the robot determines a 3-dimensional position of the one or more tracking markers.

According to another embodiment, a surgical robot system includes a robot having a robot base, a robot arm coupled to the robot base, and an end-effector coupled to the robot arm. The end-effector has a first plurality of tracking markers affixed to a base of the end-effector and a second plurality of tracking markers affixed to a guide tube of the end-effector. The second plurality of tracking markers are moveable relative to the first plurality of tracking markers from a first configuration to a second configuration. The system further includes at least one camera able to detect the first and second plurality of tracking markers in the first configuration and the second configuration. The robot determines a 3-dimensional position of the end-effector from at least one template corresponding to the first configuration or the second configuration of the first and second plurality of tracking markers.

According to another embodiment, a surgical robot system includes a robot having a robot base, a robot arm coupled to the robot base, and an end-effector coupled to the robot arm. The end-effector has a guide tube with a central longitudinal axis and a single tracking marker affixed to the guide tube. The single tracking marker is separated from the central longitudinal axis by a fixed distance. The system includes an instrument having a centerline and an array extending from the instrument with a plurality of tracking markers attached thereto. The system further includes at least one camera able to detect the single tracking marker on the guide tube and the plurality of tracking markers on the instrument. The robot determines a detected distance between the centerline of the instrument and the single tracking marker to determine if the detected distance matches the fixed distance. In this manner, the robot may determine if the instrument is positioned within the guide tube.

According to yet another embodiment, a surgical robot system includes a robot having a robot base, a robot arm coupled to the robot base, and an end-effector coupled to the robot arm, the end-effector having a guide tube. The system includes an instrument having an array extending from the instrument with a plurality of fixed tracking markers and a moveable tracking marker, the instrument receivable in the guide tube. The system also includes an implant configured to be inserted in a patient, the implant configured to be detachably coupled to the instrument. The system further includes at least one camera able to detect the plurality of fixed tracking markers and the moveable tracking marker on the instrument, wherein the robot determines a position or movement of the moveable tracking marker to determine a variable of the implant. The implant may be an expandable implant, an articulating implant, or a moveable implant, and the variable may be the height of the expandable implant, the angle of movement of the articulating implant, or the like.

According to another embodiment, a surgical robot system includes a robot having a robot base, a robot arm coupled to the robot base, and an end-effector coupled to the robot arm, wherein the robot is configured to control movement of the end-effector to perform a given surgical procedure, and wherein the end-effector is interchangeable with other end-effectors each configured to perform different surgical procedures.

DESCRIPTION OF THE DRAWINGS

FIG. 6 illustrates a surgical robot in accordance with an exemplary embodiment;

FIG. 13A illustrates a portion of a robot including the robot arm and an end-effector in accordance with an exemplary embodiment;

FIG. 13B is a close-up view of the end-effector, with a plurality of tracking markers rigidly affixed thereon, shown in FIG. 13A;

FIG. 13C is a tool or instrument with a plurality of tracking markers rigidly affixed thereon according to one embodiment;

DETAILED DESCRIPTION

Figure 1:
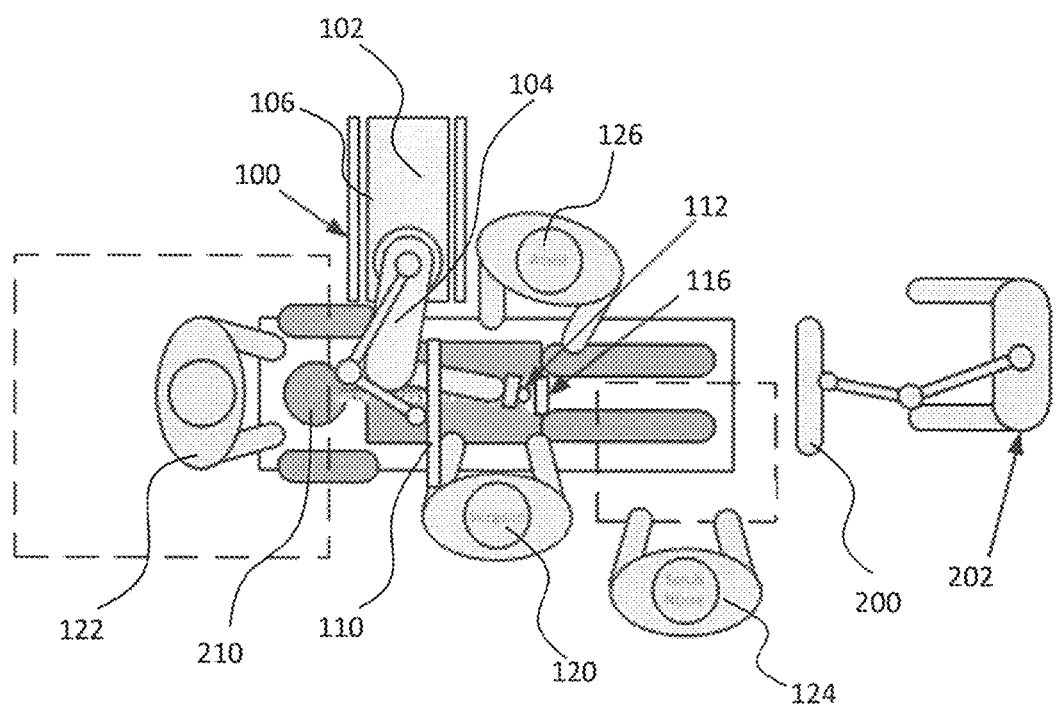
FIG. 1 is an overhead view of a potential arrangement for locations of the robotic system, patient, surgeon, and other medical personnel during a spinal procedure using the surgical navigation system and surgical navigation computing device described.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Robotic technologies described herein have the ability to provide enhanced safety and improved efficiency for surgeons during deformity correction in spinal surgeries. Likewise, the use described herein of imaging and navigation technologies, combined with robotics technologies, receives real time feedback on clinically significant parameters that previously could not be assessed intraoperatively. As such, the present inventions include devices, systems, and methods of integrating robotic, imaging, and navigation technologies into spinal deformity correction procedures.

Described herein are devices, systems and methods of implementing navigation and electromechanical control of instruments for correcting a spinal deformity. These devices, systems, and methods utilize and interact with a screw system which permits transmission of corrective forces to the vertebrae during a surgical operation and, once locked to a rod, rigidly holds the spine in the corrected position as the vertebrae fuse post-operatively. In one embodiment, the screw system utilizes a pedicle-shaped screw. In other embodiments, other screw shapes, screw types, and other devices may be used.

In one aspect, the systems and methods described utilize a surgical navigation computing device to create a data-driven surgical navigation plan for correcting the deformed spinal alignment of a patient to conform to a preferred spinal alignment.

The surgical navigation computing device identifies a mathematical description of the spinal deformity.

The surgical navigation computing device is also configured to create (or describe or plan or otherwise define) a correction plan to resolve the spinal deformity from the deformed spinal alignment to a corrected spinal alignment. The surgical navigation computing device identifies a preferred spinal alignment based on user input, historical image data for the patient, historical image data of other patients, or pre-defined preferred spinal alignments.

Described herein are also devices and equipment that may be used to apply corrective forces. In an example embodiment, the devices include screws and, more specifically, pedicle screws. The surgical navigation computing device is configured to identify recommended placement for such devices to obtain the corrected spinal alignment within the correction plan. In some embodiments, as described herein, the placement of devices including pedicle screws may be provided using a robotic navigation platform. The surgical navigation computing device may therefore communicate with such robotic navigation platforms to navigate, place, insert, and rotate the pedicle screws or other devices.

The surgical navigation computing device is also configured to capture, process, and utilize intra-operative data to ensure adherence to the correction plan. In one example where the surgeon manually performs the surgery based on the correction plan, the surgical navigation computing device obtains information regarding the procedure and verifies that the obtained information corresponds to information expected when adhering to the correction plan. Such information may include intra-operative image data regarding the intra-operative spinal alignment, and information regarding the placement, movement, and rotation of devices including pedicle screws.

Described herein are also surgical instruments including fiducial markers which are rigidly connected to devices such as pedicle screws. The fiducial markers may be used to track and/or manipulate the spinal alignment during the surgical procedure. More specifically, the fiducial markers (and the instruments to which they are connected) are manipulated during surgery and their manipulation is tracked intraoperatively. In some examples, the instruments are directly manipulated by the robotic navigation platform. As such, the fiducial markers may be utilized to ensure compliance to the correction plan, or to identify deviations therefrom. In some examples, the surgical navigation computing device is configured to identify deviations from the correction plan and to a) alert the surgeon to such deviations, b) revise the correction plan, or c) provide multiple options for a revised correction plan for review by a user such as a surgeon. The rigid body motion of the vertebral bodies will be displayed along with the spinal alignment curves to visualize the correction. Real time analysis of the tracked changes in spinal curvature will provide information to the surgeon or feedback to electromechanical control.

The surgical navigation computing device is also configured to facilitate other aspects of the pre-operative surgical procedure including identifying recommended patient positioning, anesthetic recommendations, and spinal exposure. Likewise, the surgical navigation computing device is configured to facilitate aspects of the conclusion of the surgical procedure to, for example, capture and lock rods to screw heads, identify wound closing steps and processes, identify recommended bone graft applications, and obtain post-operative image data to confirm the success of the correction. In many examples, the surgical navigation computing device interacts with a robotic navigation platform to provide some or all such procedures.

In one aspect, a surgical navigation system is provided for defining and implementing a surgical navigation plan to correct a deformed spinal alignment. The surgical navigation system includes at least one imaging device configured to capture image data. The imaging devices may include devices for three-dimensional computerized tomography ("3-D CT") scan, x-ray imaging, magnetic resonance imaging ("MRI"), or any other suitable devices for spinal imaging. In some examples, combinations of scans or imaging may be obtained by the imaging devices. The surgical navigation system also includes a surgical navigation computing device in communication with the imaging devices. The surgical navigation computing device includes a processor and a memory. The processor is configured to described the steps recited herein. Generally, the surgical navigation computing device is configured to (a) obtain and access imaging data including historical imaging data; (b) perform a spinal deformity analysis to identify alignment parameters or other descriptions of the spinal deformity; (c) obtain diagnostic data related to the patient, including bone density and health information; (d) determine spinal correction planning based in part on the imaging data and the spinal deformity analysis; (e) identify pedicle screw placement and planning based on the correction plan; (f) obtain intra-operative imaging and scanning data to monitor the adherence to the correction plan; (g) facilitate intra-operative navigation and screw placement using, for example, a robotic navigation platform; (h) monitor the placement of surgical instruments using fiducial markers etched there-upon; (i) utilize a rod link reducer or a similar device to manipulate the spine from a deformed alignment to a preferred alignment; (j) obtain measurements of devices used to perform the spinal correction from, for example, strain gauges or other electromechanical or mechanical surgical devices; (k) analyze intra-operative imaging and scanning data and surgical instrument data to determine the navigation and the adherence to the correction plan; (l) identify forces and stresses acting upon the spine based on data obtained from surgical instruments; (m) define proposed osteotomies to mitigate excessive forces and stresses acting upon the spine; (n) identify ideal bends of surgical rods that maintain spinal shape in light of the forces and stresses acting upon the spine; (o) facilitate bending a rod to the ideal bend; and (p) provide and facilitate pre-operative and post-operative surgical steps.

The surgical navigation computing device is configured to use the processor to obtain a first set of image data associated with a deformed alignment in a spine of a patient from the at least one imaging device. Image data may include information from any suitable orientation including anterior-posterior, lateral, axial, plane of maximum curvature, lateral bending, and standing. The images may be processed to segment each vertebra into 3D shapes for manipulation. The images may include three-dimensional computerized tomography ("3-D CT") scan, x-ray imaging, and magnetic resonance imaging ("MRI") or any suitable similar approaches to spinal imaging. In some examples, combinations of scans or imaging may be used. Image data may include information from any suitable orientation including anterior-posterior, lateral, lateral bending, and standing.

In some examples, the obtained images or scans may be displayed on user interfaces available to a user (e.g., a surgeon). In one example, the images or scans are displayed on a touchscreen user interface in connection with the surgical navigation system and, more specifically, attached to or associated with a surgical robot included in the surgical navigation system or the surgical navigation computing device. The user interface allows a user to manipulate the images or scans by, for example, rotating, panning, tilting, or zooming the image or scan data (including 3-D image data). The user interface also allows for segmentation of the scanned or imaged spine into segments (e.g., of vertebrae) as individual bodies. Such segmentation allows display of the segment or component shapes that may be reviewed by a surgeon or other user. Likewise, the surgical navigation computing device provides user interfaces to analyze and visualize curves connecting vertebral bodies and thus curves or lines describing the vertebral curvature. For example, lines parallel to transverse processes, spinous processes, and similar anatomical features that are oriented in a manner generally perpendicular to the axial plane may be used by the surgical navigation computing device for analysis and visualization of axial rotation.

The surgical navigation computing device is also configured to process the first set of image data to identify a set of deformed alignment parameters (or a mathematically based description of the shape of the deformed spinal alignment or components thereof) associated with the deformed alignment. In the example embodiment, such a description is one or several alignment parameters describing values of pertinent spinal features or characteristics. Generally, the surgical navigation computing device applies image processing algorithms to the image data to identify the shape of the imaged spine and identifies features in the spine to define the deformed spinal alignment (i.e., the curved shape that the spine takes in the body of the imaged patient). In one example, the spinal alignment is visualized through a curve tracing through each vertebra with segments along the medial-lateral features of the vertebra (e.g., the transverse process) to visualize rotation. In some examples, the surgical navigation computing device may define the deformed spinal alignment based partially or wholly on user input from, for example, a surgeon or other healthcare provider with access (directly or indirectly) to the surgical navigation computing device. For example, the input may include user-inputted line tracing, line selection, point identification, and segment or component identification. In such examples, the surgical navigation computing device further applies image processing software and geometric processing algorithms to the image data and deformed spinal alignment to identify parameters, best-fit lines, equations, factors or other mathematical terms or functions to describe the deformed spinal alignment or sections thereof including angles, arcs, and line segments based partially or wholly on the user-input. Relevant alignment parameters include, but are not limited to, Cobb angle, lumbar lordosis, thoracic kyphosis, cervical lordosis, axial rotation, sagittal vertical axis, sagittal curve size, pelvic tilt, pelvic incidence, T1 pelvic angle, 3D kyphosis, angle of the plane of maximum kyphosis, measurements for upper end vertebrae ("UEV"), measurements for lower end vertebrae ("LEV"), measurements for upper end instrumented vertebrae ("UIV"), and measurements for lower end instrumented vertebrae ("LIV"). In some examples, the parameters measured may include any other measurable alignment characteristics.

In some examples, the surgical navigation computing device also obtains relevant diagnostic information that may describe the health of the patient spine or the health of the patient and may therefore be relevant to defining and planning the surgical navigation to correct a spinal deformity. For example, the surgical navigation computing device may also be in communication with devices or systems that can perform or provide tests for dual energy X-ray absorptiometry ("DEXA"), peripheral dual energy X-ray absorptiometry ("pDXA"), quantitative ultrasound ("QOS"), and peripheral quantitative computer tomography ("pQCT"). By obtaining such data, the surgical navigation computing may refine or improve on a navigation plan to, for example, compensate for a determination that a patient spine is relatively brittle or porous.

The surgical navigation computing device is also configured to identify a set of corrected alignment parameters associated with a preferred alignment of the spine of the patient. In some examples, a preferred alignment (or preferred spinal alignment) may be defined parametrically by adjusting alignment parameters of the deformed alignment (or deformed spinal alignment). In other examples, a preferred alignment may be determined by manipulating images and models (e.g., two-dimensional images and three-dimensional models). In additional examples, a preferred alignment may be determined by the surgical navigation computing device adjusting the alignment parameters (based on patient input or algorithmically) of the deformed alignment to an idealized alignment. The idealized alignment may be identified based on historic patient scans, images, or models (i.e., previous images of the patient spinal alignment when in a healthy condition). The idealized alignment may also be determined by the surgical navigation computing device accessing reference spinal scans or images from other patients or composites thereof. In at least some examples, a user may be presented with models of corrected spinal alignments at a user interface (e.g., a touch screen user interface associated with the surgical navigation computing device or a surgical robotic platform in connection therewith) and the user may select from the model for use in spinal correction. Each such presented model is associated with corrected alignment parameters and therefore a correction goal. The surgeon or other user may also manipulate the alignment parameters (or other mathematical descriptions of the deformed spinal alignment) through the surgical navigation computing device to create corrected alignment parameters (or other mathematical descriptions of the corrected spinal alignment). Thus, in addition to automatically identified correction plans, the surgical navigation computing device may also receive user input to modify a correction plan based on the preference of a surgeon (or other user).

The surgical navigation computing device is also configured to process the first set of image data, the set of deformed alignment parameters, and the set of corrected alignment parameters to generate a correction plan to surgically manipulate the deformed alignment to the preferred alignment. In one example, the surgical navigation computing device processes the alignment parameters (or best-fit lines, equations, factors or other mathematical terms or functions to describe the deformed spinal alignment) along with the image data to identify a correction plan to correct the spinal alignment to conform to a preferred (or healthy or idealized) spinal alignment as the corrected spinal alignment. As described below and herein, the correction plan includes a description of corrective forces to apply to points along the spine to conform the spinal alignment to the corrected spinal alignment. The correction plan includes, for example, (a) placement, orientation, and insertion plans for pedicle screws, rod link reducers, and other surgical devices; (b) recommended forces and speed to apply when manipulating each such pedicle screw, rod link reducer, or other surgical device; (c) placement and depth of recommended osteotomies; (d) identified anticipated corrective loads acting on the spine.

The correction plan may also include definitions for components to use to provide the corrective forces, rates of speed to apply the corrective forces, and patterns of application of corrective forces. As described below, in some examples, the surgical navigation computing device may also utilize the diagnostic information associated with the patient (e.g., bone density and bone health information) to further refine the correction plan. In some examples, the surgical navigation computing device may also receive user input to define the corrected spinal alignment and components of the correction plan. For example, a surgeon (or any other suitable user) may manipulate image data using a user interface (available through the surgical navigation computing device or at a user terminal in connection therewith) to adjust the deformed spinal alignment reflected in the image data to a corrected spinal alignment.

The surgical navigation computing device is also configured to provide navigation through the correction plan to facilitate surgical manipulation of a patient spine from the deformed alignment to the preferred alignment. In one example, the correction is performed manually by a surgeon and information for performing the correction is provided to a user (e.g., the surgeon) through a user interface associated with the surgical navigation computing device. In another example, the surgical navigation computing device is in communication with a surgical robot that is part of the surgical navigation system. In such examples, the surgical navigation computing device is configured to cause the surgical robot to apply the correction plan to surgically manipulate the patient spine from the deformed alignment to the preferred alignment. In a second example, the surgical navigation computing device is configured to obtain feedback from the surgical robot describing the movement of the surgical robot. For example, the surgical navigation system allows the surgical navigation computing device to receive information from the surgical robot regarding the motion of the surgical robot in terms of orientation, timing, and speed, the manipulation of surgical devices, the application of forces by the surgical robot, and the pattern and timing of the motion of the robot. The surgical navigation computing device is also configured to identify a planned movement of the surgical robot based on the correction plan. The planned movement may include expected motion of the surgical robot in terms of orientation, timing, and speed, the expected manipulation of surgical devices, the expected application of forces by the surgical robot, and the expected pattern and timing of the motion of the robot. The surgical navigation computing device is also configured to compare the feedback to the planned movement to identify deviations in the robot movement from the correction plan. The surgical navigation computing device is also configured to transmit an alert when a deviation from the correction plan is identified. In some examples, the surgical navigation computing device revises the correction plan based on a deviation by, for example, re-routing the navigation plan of the correction plan when a deviation occurs.

Described herein are also methods for monitoring the correction or surgical procedure including: (a) obtaining images and scans of the intra-operative spinal alignment and intra-operative spinal movement; (b) obtaining other diagnostic information related to the patient including spinal health information; (c) obtaining information regarding the orientation, movement, and placement of surgical equipment based at least partially on the images and scan information; (d) identifying fiducial markers etched on, attached to, or associated with each surgical equipment to determine the specific position, orientation, and movement of each of the surgical devices; (e) accessing information related to forces acting on the surgical equipment from, for example, strain gauges in communication with the surgical navigation computing device or other mechanical or electromechanical devices; (f) identifying or updating anticipated corrective loads acting on the spine based on the information collected; (g) identifying an ideal rod bend for a surgical rod based partially on information from a strain gauge associated with a rod link reducer; (h) facilitating the ideal rod bend; (i) adjusting pedicle screw placement based on anticipated corrective loads; (j) identifying recommended osteotomies to mitigate the corrective loads acting on the spine; and (k) confirming adherence of the surgical procedure to the correction plan or revised correction plan.

Accordingly, in some examples, the surgical navigation computing device is also configured to obtain a second set of image data associated with an intra-operative spinal alignment in a patient during surgery from the at least one imaging device. In some examples, during intra-operative navigation and correction, the surgical navigation system uses the imaging devices to track and display (on a user interface associated with the surgical navigation system) the location of vertebral bodies. The tracked and displayed vertebral bodies may include anterior-posterior, lateral, axial, plane of maximum curvature, lateral bending, and standing. In some examples, the surgical navigation computing device tracks using motion capture of fiducial markers etched on or associated with instruments rigidly attached to surgical devices (including pedicle screws embedded in the vertebral bodies). Using such methods, the surgical navigation computing device (and associated systems and devices including interactive touchscreens) provides monitoring of intra-operative alignment parameters (i.e., the alignment parameters for a spine during correction) or other mathematically based descriptions of intra-operative spinal alignment in real-time. Thus, intra-operative alignment parameters may be compared to deformed alignment parameters (i.e., alignment parameters for the pre-operative deformed spinal alignment) and to preferred alignment parameters (i.e., alignment parameters for the intended post-operative corrected spinal alignment). Thus, any suitable alignment parameters may be monitored and used to effect such comparison including, Cobb angle, lumbar lordosis, thoracic kyphosis, cervical lordosis, axial rotation, sagittal vertical axis, sagittal curve size, pelvic tilt, pelvic incidence, T1 pelvic angle, 3D kyphosis, angle of the plane of maximum kyphosis, measurements for UEV, measurements for LEV, measurements for UIV, and measurements for LIV. Similarly, descriptions or definitions of intra-operative spinal alignment may be compared to analogous descriptions or definitions for pre-operative deformed spinal alignment and intended post-operative corrected spinal alignment.

As described herein, the surgical navigation computing device is also configured to obtain a third set of image data associated with a post-operative spinal alignment in a patient after surgery from the at least one imaging device. Thus, using the same methods, the post-operative image data may be used to obtain corrected alignment parameters (i.e., alignment parameters for the actual post-operative corrected spinal alignment) which may then be compared to deformed alignment parameters, intra-operative alignment parameters, and preferred alignment parameters to determine whether the desired correction was obtained and, if not, to identify sources of deviation therefrom. Similarly, descriptions or definitions of post-operative spinal alignment may be compared to analogous descriptions, definitions for pre-operative deformed spinal alignment, intended post-operative corrected spinal alignment, and intra-operative spinal alignment. In some examples, the comparisons provided may be shown using suitable user interfaces including tracking alignment parameters (or other definitions) using numerical indicators, graphs, slider bars, or other suitable outputs.

In another example, two-dimensional images or three-dimensional models may be compared as between pre-operative spinal alignment, intra-operative spinal alignment, preferred spinal alignment, and actual post-operative spinal alignment. Thus, such images and models may be compared and/or overlaid (using the user interfaces described) to observe variations and, for example, identify necessary steps required (e.g., translation and rotation) to adjust the spinal alignment (e.g., from the intra-operative spinal alignment to the preferred spinal alignment).

In some examples, particular components of images or scans captured at any phase (e.g., pre-operative spinal alignment, intra-operative spinal alignment, and post-operative spinal alignment) or simulated (e.g., preferred spinal alignment). Such components may be analyzed to identify forces acting on the spine. In one example, the vertebral foramen shape may be analyzed and compared from each phase to identify and estimate the levels of, for example, tension or compression acting on the spinal cord.

For example, positive displacement between centroids of adjacent vertebral foramen result in a net tension on the spinal cord. Thus, the surgical navigation computing device may identify such displacement and estimate resulting tension. In such examples, the user interfaces described may present or depict the forces (e.g., tension or compression) acting on the spinal cord using a suitable interface (e.g., a color map on a spline between vertebral bodies). Such depictions may be used to guide or assist the navigation or act as a warning.

In another embodiment, the surgical navigation computing device is configured to identify a planned intra-operative spinal movement based on the correction plan. Specifically, the correction plan may define the expected movement of the spine and surgical equipment and related components, with respect to location, orientation, and timing. The surgical navigation computing device therefore accesses such definitions for movement to identify anticipated path and pattern of navigation. The surgical navigation computing device processes the second set of image data and the planned intra-operative spinal movement to identify deviations from the correction plan (i.e., manners in which the actual navigation and correction fails to follow the anticipated path and pattern). The surgical navigation computing device transmits an alert when a deviation from the correction plan is identified.

In many embodiments, the surgical navigation system utilizes a rod link reducer to perform the correction plan. In one example, the surgical navigation system utilizes a surgical robot that controls, manipulates, and otherwise uses the rod link reducer. In another example, a surgeon manually controls, manipulates, and otherwise uses the rod link reducer. The systems and methods may utilize any suitable rod link reducer but an example rod link reducer may be one described in U.S. Pat. No. 9,408,641, filed on Feb. 2, 2009. The systems and methods described utilize a method of intra-operative tracking of the progress of deformity correction using the rod link reducer instruments. Notably, in many embodiments fiducial markers are attached to (via etching, affixing a sticker with the marker, or any other suitable method) the rod link reducer instruments, the temporary rods, the pedicle screws, and other surgical devices and then used to track motion of the vertebrae. In one example, the surgical navigation system records, learns, or otherwise obtains information regarding the shape and form of the fiducial marker and the spatial relationship between the fiducial marker and the associated surgical device including, e.g., the relative location of the fiducial marker on the surgical device, the dimensions of the fiducial marker and the surgical device, and the orientation(s) of the surgical device that expose the fiducial marker. The surgical navigation system may thus record, learn, or obtain that information using the surgical navigation computing device, a surgical robot included in the surgical navigation system (and in communication with the surgical navigation computing device), or any other computing device. Notably, in some embodiments, the surgical navigation computing device is integrated into the surgical robot or vice versa. In further embodiments, the surgical navigation computing device is also integrated with the imaging devices and/or the surgical robot. The surgical navigation system thus may use the imaging devices to track the location(s) of fiducial markers during a surgical operation, and determine the relative location of the surgical devices to which the fiducial markers are attached or associated. In some embodiments, the surgical navigation system provides or displays a schematic representing the anatomical shape of the intra-operative spinal alignment in real-time using a touchscreen user interface.

In one embodiment, two fiducial markers are placed on each of the surgical devices (e.g., temporary rods) and one fiducial marker is also placed on the spinous process of the vertebrae at the apex of the deformity (or deformities). The two fiducial markers on each surgical device are tracked using the approach described above in order to create a line segment at the proximal and distal ends of the deformity. The orientation of the line segments with respect to one another may provide a visual representation of the magnitude of the curve in the coronal plane. The line segments may also be used to display measurements of applicable spinal parameters such as coronal Cobb angle. Similarly, the fiducial markers may be used to display a visual representation of the spinal alignment in the sagittal and axial planes.

Figure 24:
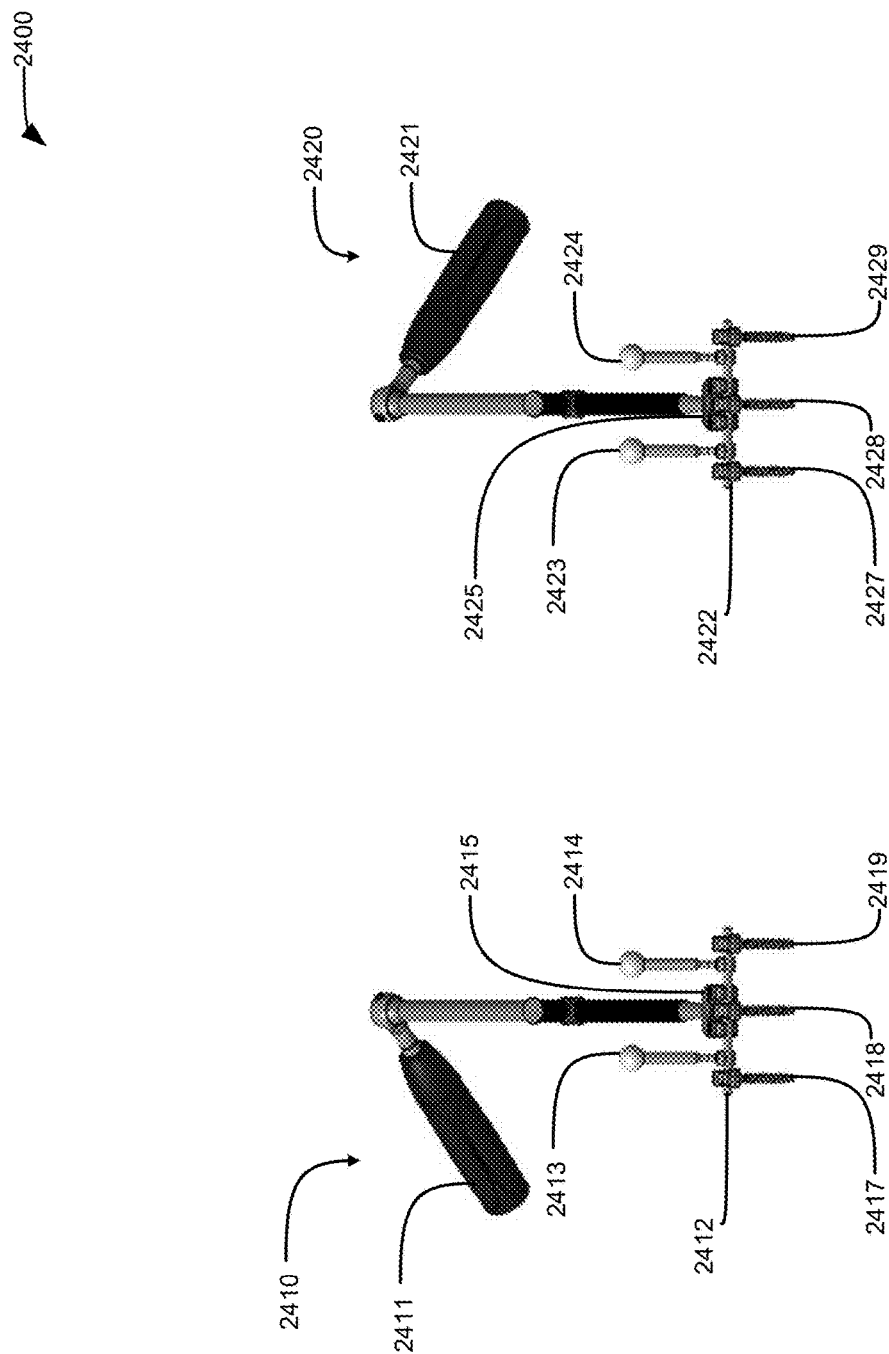
FIG. 24 illustrates rod link reducer instrumentation including temporary rods and fiducial markers placed on the temporary rods according to one embodiment of the invention.
Figure 25:
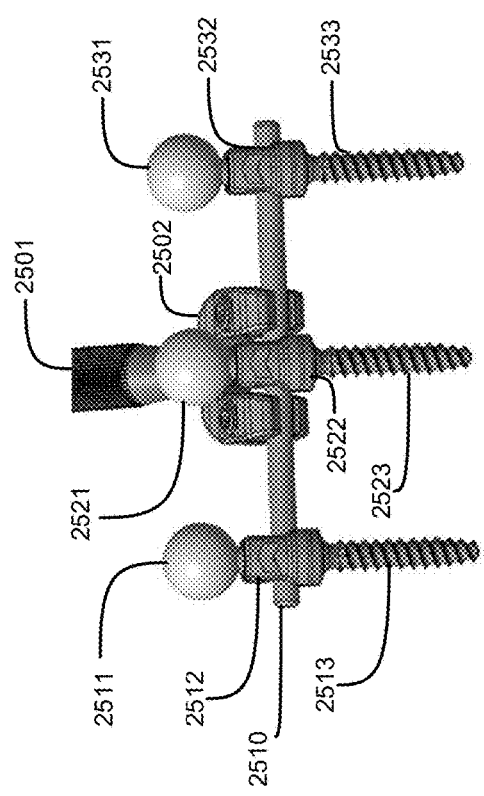
FIG. 25 illustrates a locking cap system with integrated fiducial marker according to one embodiment of the invention.

The fiducial markers may also be attached to (via etching, affixing a sticker with the marker, or any other suitable method) the surgical device with a unique clamping instrument as shown in FIGS. 24 and 25. Other embodiments may include fiducial markers which are integrated with or engage with the locking caps used to secure the temporary rods. Alternatively, the fiducial markers may be attached to the manipulating arms or the coupling rod.

Additional fiducial markers may be placed on the vertebral segments at the apex of the deformity (or deformities) in order to track motion of the entire spine during the procedure. Such fiducial markers may be secured directly to the anatomy via specialized clamping mechanisms or indirectly by attaching to pedicle screws.

Thus, in one embodiment, the surgical navigation computing device is configured to identify an associated fiducial marker attached to each of a plurality of surgical devices used to manipulate the patient spine from the deformed alignment to the preferred alignment, wherein each associated fiducial marker has a fixed spatial relationship to the respective surgical device. As described above, such identification may be provided by inventorying or imaging each surgical device, algorithmically identifying fiducial markers in such processes, and/or receiving user input to identify the fiducial marker in the image. In other examples, the identification may be provided by receiving definitional files or data describing the shape, form, dimensions, and layout of the fiducial markers. Such definitional files or data may also include a description or definition of the relative orientation, scale, and size of the fiducial marker with respect to the associated surgical device (and further including size and scale information for each surgical device).

The surgical navigation computing device is also configured to obtain a second set of image data associated with an intra-operative spinal alignment in a patient during surgery from the at least one imaging device in order to provide the tracking steps described above. As such, the surgical navigation computing device also processes the second set of image data to identify a set of position information for each of the plurality of surgical devices based at least in part on the associated fiducial marker. In an example embodiment, each of the set position information includes location information and orientation information.

In further embodiments, the surgical navigation computing device is configured to identify an expected navigation plan for each of the plurality of surgical devices from the correction plan. The navigation plan represents the intended path and pattern of each surgical device during the course of the performance of the correction plan. (The navigation plan may also include the changes to the spinal alignment during the course of the performance of the correction plan.)

The surgical navigation computing device is also configured to process the expected navigation plans and the set of position information to identify deviations from the navigation plans. The surgical navigation computing device is further configured to transmit an alert when a deviation from each of the navigation plans is identified. Alternately, the surgical navigation computing device may revise the correction plan based on the deviation. In at least some examples, the surgical navigation computing device may determine an anticipated intra-operative spinal alignment based on the navigation plan (i.e., identifying the relative spinal orientation and shape based on the anticipated location of the surgical devices) and identify a path and pattern of the spinal alignment. Thus, in some embodiments, the surgical navigation computing device may obtain image data regarding the intra-operative spinal alignment and compare such image data to the determined path and pattern of spinal alignment to identify deviations. If such intra-operative deviations are found, the surgical navigation computing device may transmit an alert or revise the correction plan based on the deviation.

In some examples, sensors are included on the surgical devices to identify forces or stresses acting on the spine to which the surgical devices are attached. Thus, in addition to tracking the location and orientation of the spine and anatomy using fiducial markers, these sensors allow the surgical navigation computing device to monitor the forces exerted on the spine during correction maneuvers. Real-time data regarding corrective forces may identify when surgical equipment (e.g., pedicle screws) are at risk of pulling out or plowing or otherwise failing due to the corrective forces. Such data may be used to provide safe and stable correction maneuvers during surgery.

In one embodiment, strain gauge sensors are placed on the manipulating arms of a rod link reducer. Deflection of the manipulating arms during correction may be sensed by the strain gauge and sent to the surgical navigation computing device, the surgical robot, or the surgical navigation system. Generally, increased corrective forces on the spine (or the anatomy to which the surgical device is attached or connected) causes an increased reading from the strain gauge or other sensor. The surgical navigation system may record, monitor, and display the force or strain readings (via a touchscreen) to a surgeon and provide alerts or warnings when the strain is increased to unsafe levels exceeding a predefined maximum threshold. (Such thresholds may be determined based on known properties of the surgical equipment to resist forces or tension and information regarding the spine and spinal health of the patient.) The surgeon may use such data to adjust correction maneuvers accordingly. In some examples, a surgical robot provides or facilitates the surgical operation and the surgical robot may receive data from the surgical navigation computing device (or the surgical navigation system) indicating that the strain or forces exceed the threshold. The surgical robot may alter the correction plan based on a pre-defined alternative method or request input from a user to address the problem posed by the excess forces.

In other embodiments, the sensors (e.g., strain gauge sensors) may be placed on the coupling rod, handles, coupling clamps, or temporary rods. Alternatively, such sensors may be placed on the pedicle screws themselves to directly measure stress at the bone/screw interface. Based on such information, the surgical navigation computing device may monitor more force and stress information and determine when stress is at or nearing a level where the surgical device may fail (e.g., the pedicle screw may pullout or plow).

In some examples, the surgical navigation system therefore also includes a strain gauge sensor attached to a rod link reducer (or other suitable sensor). The rod link reducer is applied to manipulate the patient spine from the deformed alignment to the preferred alignment. The strain gauge sensor is in communication with the surgical navigation computing device and provides strain information to the surgical navigation computing device, the surgical navigation system, and any devices in communication therewith (including the surgical robot).

Further, in some examples, the surgical navigation computing device obtains feedback from the strain gauge sensor and processes the correction plan to identify an acceptable range (e.g., defined by thresholds) of strain on the rod link reducer. The surgical navigation computing device transmits an alert when the feedback exceeds the acceptable range of strain. In some examples, the surgical navigation computing device adjusts the correction plan when the feedback exceeds the acceptable range of strain.

As described herein, surgical instruments like the rod link reducer instruments are typically used to manipulate the deformed spine into a corrected state using anchoring points on the convex side of the spine. After the correction is achieved and locked into place, a permanent rod is typically bent to the appropriate shape and placed on the contralateral side to hold the correction. The rod link reducer instruments are typically then removed and a second permanent rod is inserted. Described herein is an approach to define the shape and bend of the permanent rod to hold the spine in a corrected position after surgery (while the vertebrae fuse). During this period, the bent rod experiences the same forces which caused the deformity. For a successful surgery, the bent rod must resist such forces. Without the approach described herein, these forces often cause the permanent rods to flatten or bend resulting in loss of correction. Without the approaches described herein, in order to counteract the loss of correction, surgeons often over-bend the permanent rod before inserting it so that the final shape of the rod after being acted upon by the forces in the spine is closer to the desired shape. This method is called differential rod bending and is often imprecise and dependent on the judgment and prior experience of surgeons. Therefore, it would be advantageous to provide surgeons relevant data that they can use to make more accurate judgments when it comes to differential rod bending. Furthermore, it would be more advantageous if the relevant data could be used to automatically bend a rod to the appropriate shape that would achieve the desired correction post-operatively.

Therefore, the surgical navigation system and methods described include a method of collecting and analyzing relevant pre-operative and intra-operative data to define the shape of a permanent rod with the ideal shape ("ideal bend" or "preferred bend") for maintaining the desired deformity correction. As described above, the surgical navigation computing device may obtain pre-operative imaging data to determine measurements (e.g., alignment parameters) of clinically relevant variables such as upper instrumented vertebrae (UIV), lower instrumented vertebrae (LIV), thoracic kyphosis, standing coronal Cobb angle, bending coronal Cobb angle, and sagittal vertical axis (SVA). Thus, the imaging devices described above may capture relevant pre-operative and intra-operative image and scan data to determine such measurements (e.g., alignment parameters).

Navigation methods such as those described above are used to monitor the spinal alignment during surgery and to track changes to the alignment parameters (and other relevant definitions) measured pre-operatively. Further, sensors placed on surgical devices (e.g., rod link reducers or implants) are used to measure the forces exerted on the spine during the correction. The intra-operative data collected may be recorded and analyzed by the surgical navigation computing device (or surgical robot) to identify forces that are anticipated to act on the spine in post-operative alignment. Further, after the procedure completes and the corrected alignment is achieved and locked into place using the rod link reducer instruments, the position of the contralateral pedicle screws and image data for the spinal alignment may be collected by the surgical navigation computing device (or surgical robot). The surgical navigation computing device processes the pre-operative measurements, intra-operative measurements, intra-operative correction forces, pedicle screw locations, and image model or profile (i.e., two-dimensional image or three-dimensional model) with a rod shape algorithm to determine preferred, ideal, or optimal rod shapes. In some examples, the surgical navigation computing device is configured to provide the preferred rod shapes to a user via the touchscreen interface. In other examples, the surgical navigation system includes or is in communication with a rod bender machine and the preferred rod shapes are submitted or sent to the rod bender machine. The rod bender machine applies the received preferred rod shapes to automatically bend surgical rods to conform to the preferred rod shape. In some examples, the surgeon may place the appropriate pre-bent rod on the contralateral side and lock it into place. The rod link reducer instrumentation may be removed and the second pre-bent rod is inserted and locked into place.

In some examples, the rod shape algorithm functions as follows. The surgical navigation computing device uses the pre-operative and intra-operative image and scan data (and the alignment parameters or definition data derived therefrom) to determine the amount of deflection that will occur to the permanent rod when it is inserted. The algorithm also receives information regarding the size, shape, material composition, and properties of the rod. (Such information may be provided by a manufacturer definition file or a user.) The data regarding the amount of deflection and the rod are used to determine the optimal, ideal, or preferred rod shape will take into consideration the size and material properties of the rod. In some examples, the algorithm also incorporates other variables that may influence preferred rod bend including spinal balance, and patient height, patient weight, and patient bone density.

As described above and herein, the surgical navigation computing device may also collect post-operative image and scan data and obtain post-operative measurements and clinical outcome data. In some examples, the rod shape algorithm is iteratively updated based on such post-operative outcome data. In some examples, the rod shape algorithm applies a machine learning algorithm to train the rod shape algorithm to improve its performance based on new training data (i.e., a combination of historic preferred rod shapes, expected clinical outcomes, and actual clinical outcomes).

Based on the above, in some examples, the surgical navigation computing device is configured to obtain feedback from the strain gauge sensor identifying strain forces acting on the spine. The surgical navigation computing device also processes the feedback and the correction plan to identify a preferred bend of a permanent rod. As described, a permanent rod with the preferred bend is configured to maintain a form resistant to the identified strain forces.

In other embodiments, the surgical navigation system includes a rod bending machine in communication with the surgical navigation computing device. In such examples, the surgical navigation computing device (or the processor thereof) is further configured to instruct the rod bending device to bend a first permanent rod to the shape of the preferred bend.

As described above, the systems and methods provided may also provide recommended placement and definition for osteotomies to mitigate the impact of excessive stress or force on the spine post-surgery. An osteotomy is a procedure in which a portion of bone is removed or otherwise altered. Typically, osteotomies are often needed during spinal deformity surgery in order to make the spine flexible enough to move into a corrected state. If the spine is not flexible enough to move (absent an osteotomy), then spinal correction may be difficult and could place excessive stress on the surgical devices (e.g., implants or rods). Excessive stress on the implants could result in screw plowing or pullout or rod fracture.

As described above, pre-operative and intra-operative data are used by the surgical navigation computing device to determine a preferred rod shape capable of resisting forces and holding the corrected shape. The surgical navigation computing device also uses pre-operative and intra-operative data to define the placement and nature of recommended osteotomies. The sensors (e.g., strain gauges) described above may be used to identify when the pedicle screws are at risk of pulling out or plowing. Thus, the surgical navigation computing device obtains information from the sensors (e.g., strain gauges) to determine if excessive force is placed on the pedicle screws during correction. The surgical navigation computing device tracks the orientation and location of the spine during correction. The surgical navigation computing device processes such orientation and location data along with force data from sensors and applies an osteotomy algorithm. The osteotomy algorithm processes such information to determine preferred locations and extents (or sizes) of osteotomies. In some examples, the touchscreen user interface presents proposed osteotomies identified by the osteotomy algorithm. In other examples, the surgical robot may implement osteotomies identified by the osteotomy algorithm.

In some embodiments, the surgical navigation computing device obtains feedback from the strain gauge sensor identifying forces acting on the spine. The surgical navigation computing device also analyzes the feedback and the correction plan to anticipated forces acting on a pedicle screw used in the surgical manipulation of the patient spine. The surgical navigation computing device further determines that the anticipated forces exceed a threshold defining a risk of pull out or plowing by the pedicle screw. The surgical navigation computing device also identifies at least one osteotomy plan to mitigate the anticipated forces to below the threshold, wherein the osteotomy plan includes at least an osteotomy location and an osteotomy depth. The surgical navigation computing device further updates the correction plan with the at least one osteotomy plan.

In many embodiments, the surgical navigation computing device is in communication with a surgical robot (or integrated therewith) and controls the surgical robot to manipulate and navigate surgical devices such as the rod link reducer. In one example, the serial arm manipulator of the surgical robot is used to manipulate the navigated rod link reducer described above or a standard non-navigated rod link reducer. In some examples, the surgical navigation computing device paths displacement of the vertebral bodies attached to the manipulating arms. In some examples, the surgical navigation computing device plans for gradual and/or controlled correction between the deformed and corrected alignments. In other examples, the end effector of the surgical robot attaches rigidly to the manipulating arm. In further examples, the surgical navigation computing device causes vision targets on the manipulating arm used to align and attach the manipulating arm. In other examples, the end effector may be guided manually to engagement by the surgeon. In some examples, in place of fiducial markers located on manipulating arms of the surgical robot, active markers on end effectors may be used to track motion of the manipulating arm when engaged. In further examples, two serial arm manipulators of the surgical robot may be used to simultaneously control both manipulating arms. (Both manipulating arms communicate and coordinate with the surgical navigation system to avoid collisions and provide efficient and consistent motion.) In some examples, one serial arm manipulator is used with the other arm anchored to a table attachment or held or controlled by the surgeon. In most embodiments, the manipulating arms are articulated gradually by the surgical robot to correct deformity without risking damage. In some examples, the surgical robot may be caused to initiate the correction by a user (e.g., a surgeon) pressing or depressing a pedal or foot pedal, and paused by releasing the pedal. In some examples, the surgical robot may use a load cell in a "wrist" in addition to or in place of strain gauges to monitor corrective forces and moments. In some examples, force-displacement data may be used to provide real-time feedback regarding the correction procedure and adherence to the correction plan. Similarly, such force-displacement data may be used for adjustment of correction planning or pathing. In some examples, a force threshold or a drop in linear force-displacement curves may be used to identify potential pullout of surgical devices (e.g., pedicle screws) or loosening of interfaces. It such a pullout or loosening is detected, the surgical robot may be instructed by the surgical navigation computing device to halt, pause, or relax motion. In such cases, if the force-displacement data indicates that the force has dropped below a threshold level indicating pullout or loosening, correction may continue. In such examples, the surgical navigation computing device may adjust the correction to reduce corrective forces, or the amount of correction can be adjusted. In some examples, the spine may be manipulated to pivot about a center of rotation level with the spinal cord, minimizing stretch or buckling of the cord. Rigid body motion of the vertebral bodies can be tracked to prevent impingement of the cord. An angular displacement can be applied to achieve a specific angle of correction.

In such examples, the surgical navigation system therefore includes a surgical robot in communication with the surgical navigation computing device. The processor is further configured to instruct the surgical robot to the apply the correction plan by controlling and manipulating the rod link reducer to manipulate the patient spine from the deformed alignment to the preferred alignment.

In some examples, the surgical navigation system is configured to provide navigated reduction, derotation, and utilize screw extender instruments. In the example embodiment, a screw extender instrument (similar to a navigated screw driver) has unique fiducial markers built into, etched onto, or added to the instrument. The instrument rigidly attaches to the screw head and aligns with the drive feature of the screw shank to be rigidly coupled to the vertebral body. Fiducial markers attached to reduction, derotation, and screw extender instruments can be used to track rigid body motion of vertebral bodies during reduction and derotation procedures. Screw extender instruments attached to screws on the contralateral side from reduction and derotation instruments can be used to rigidly track the vertebral bodies. Reflective markers/rings mounted to threaded reduction instruments may be used to measure the amount of reduction. Strain gauges attached to the instruments may be used to monitor reduction and derotation loads.

In some examples, the serial arm manipulator of the surgical robot is used to manipulate the navigated reduction and derotation instruments described above or a standard non-navigated instrument. In such examples, displacement pathing may be used to control the center of rotation of the derotation maneuver. This may be used to rotate about a rod, the center of the vertebral body, the center of the canal, or prevent loss of kyphosis during correction. Motion of vertebral bodies may be tracked via the active markers on the end effector if it is rigidly attached to an instrument. Forces and moments may be monitored by the load cell in the wrist to prevent pedicle blowout or loosening of the bone-screw interface.

As described above, the systems and methods utilize fiducial markers to track the motion, orientation, and location of surgical equipment, and to track the movement of the spinal alignment during the procedure. Fiducial markers may be built into or added to extended tabs of MIS tulips, screw extender, or other reduction or derotation instrument. In an alternative embodiment, the fiducial markers may be active marker arrays with infra-red LEDs with variations in position, wavelength, and/or pulse pattern to allow unique identification of the array. In such examples, the fiducial markers may be a single-use, sterile-packed instrument that is activating a pull-tab that connects the battery. Each tulip/instrument may have a unique set of locations so that navigation can distinguish between each screw (e.g., T10, Right) so that each screw can be simultaneously tracked. In some examples, the fiducial markers can be used with a screwdriver array or screw extender for navigation.

In further examples, correction planning may be used to estimate the degree of forces required to correct the spine. For example, the trajectory, diameter, and length of a pedicle screw may be adjusted to improve resistance to loosening of the bone-screw interface in a specific loading condition. In such an example, a screw anticipated to undergo more sagittal reduction than coronal reduction may be placed to improve its pullout strength in the posterior direction over loosening in the lateral direction. A finite element model could be used with varying loading conditions, screw trajectories, and dimensions in an optimization study.

Further, in some examples, the surgical navigation computing device may be configured to obtain a second set of image data associated with an intra-operative spinal alignment in a patient during surgery from the at least one imaging device. Further, the surgical navigation computing device may be configured to identify a set of pedicle screw placement definitions from the correction plan, the set of pedicle screw placement definitions identifying a preliminary location and orientation for each of an associated set of pedicle screws. The surgical navigation computing device may also be configured to process the second set of image data and the correction plan to identify anticipated corrective loads on each of the associated set of pedicle screws. The surgical navigation computing device may additionally be configured to revise the set of pedicle screw placement definitions for each of the associated set of pedicle screws, based in part on the anticipated corrective loads. The surgical navigation computing device is also configured to update the correction plan with the revised set of pedicle screw placement definitions.

Generally, the systems and methods described herein are configured to perform at least the following steps: obtain a first set of image data associated with a deformed alignment in a spine of a patient from the at least one imaging device; process the first set of image data to identify a set of deformed alignment parameters associated with the deformed alignment; identify a set of corrected alignment parameters associated with a preferred alignment of the spine of the patient; process the first set of image data, the set of deformed alignment parameters, and the set of corrected alignment parameters to generate a correction plan to surgically manipulate the deformed alignment to the preferred alignment; provide navigation through the correction plan to facilitate surgical manipulation of a patient spine from the deformed alignment to the preferred alignment; cause a surgical robot in communication with the surgical navigation computing device to apply the correction plan to surgically manipulate the patient spine from the deformed alignment to the preferred alignment; obtain feedback from the surgical robot describing the movement of the surgical robot; identify a planned movement of the surgical robot based on the correction plan; compare the feedback to the planned movement to identify deviations in the robot movement from the correction plan; transmit an alert when a deviation from the correction plan is identified; obtain a second set of image data associated with an intra-operative spinal alignment in a patient during surgery from the at least one imaging device; identify a planned intra-operative spinal movement based on the correction plan; process the second set of image data and the planned intra-operative spinal movement to identify deviations from the correction plan; transmit an alert when a deviation from the correction plan is identified; obtain feedback from a strain gauge sensor attached to a rod link reducer, wherein the rod link reducer is applied to manipulate the patient spine from the deformed alignment to the preferred alignment, wherein the strain gauge sensor is in communication with the surgical navigation computing device; process the correction plan to identify an acceptable range of strain on the rod link reducer; transmit an alert when the feedback exceeds the acceptable range of strain; obtain feedback from the strain gauge sensor identifying strain forces acting on the spine; process the feedback and the correction plan to identify a preferred bend of a permanent rod, wherein a permanent rod with the preferred bend is configured to maintain a form resistant to the identified strain forces; instruct a rod bending device in communication with the surgical navigation computing device to bend a first permanent rod to the shape of the preferred bend; obtain feedback from the strain gauge sensor identifying forces acting on the spine; analyze the feedback and the correction plan to anticipated forces acting on a pedicle screw used in the surgical manipulation of the patient spine; determine that the anticipated forces exceed a threshold defining a risk of pull out or plowing by the pedicle screw; identify at least one osteotomy plan to mitigate the anticipated forces to below the threshold, wherein the osteotomy plan includes at least an osteotomy location and an osteotomy depth; update the correction plan with the at least one osteotomy plan; instruct a surgical robot to the apply the correction plan by controlling and manipulating the rod link reducer to manipulate the patient spine from the deformed alignment to the preferred alignment; obtain a second set of image data associated with an intra-operative spinal alignment in a patient during surgery from the at least one imaging device; identify a set of pedicle screw placement definitions from the correction plan, the set of pedicle screw placement definitions identifying a preliminary location and orientation for each of an associated set of pedicle screws; process the second set of image data and the correction plan to identify anticipated corrective loads on each of the associated set of pedicle screws; revise the set of pedicle screw placement definitions for each of the associated set of pedicle screws, based in part on the anticipated corrective loads; update the correction plan with the revised set of pedicle screw placement definitions; identify an associated fiducial marker attached to each of a plurality of surgical devices used to manipulate the patient spine from the deformed alignment to the preferred alignment, wherein each associated fiducial marker has a fixed spatial relationship to the respective surgical device; obtain a second set of image data associated with an intra-operative spinal alignment in a patient during surgery from the at least one imaging device; process the second set of image data to identify a set of position information for each of the plurality of surgical devices based at least in part on the associated fiducial marker, wherein each of the set position information includes location information and orientation information; identify an expected navigation plan for each of the plurality of surgical devices from the correction plan; process the expected navigation plans and the set of position information to identify deviations from the navigation plans; and transmit an alert when a deviation from each of the navigation plans is identified.

Figure 2:
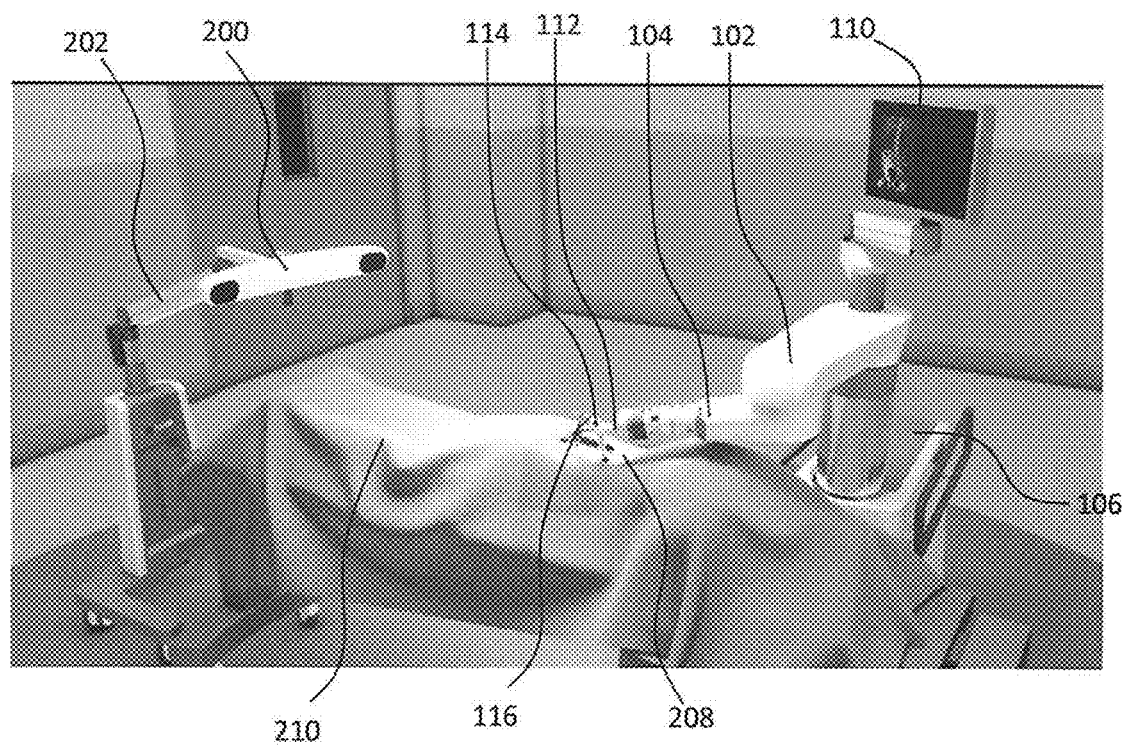
FIG. 2 illustrates the robotic system including positioning of the surgical robot and the camera relative to the patient according to one embodiment.

Described below are exemplary surgical robot systems that may be used with the surgical navigation system described herein. Turning now to the drawing, FIGS. 1 and 2 illustrate a surgical robot system 100 in accordance with an exemplary embodiment. Surgical robot system 100 may include, for example, a surgical robot 102, one or more robot arms 104, a base 106, a display 110, an end-effector 112, for example, including a guide tube 114, and one or more tracking markers 118. The surgical robot system 100 may include a patient tracking device 116 also including one or more tracking markers 118, which is adapted to be secured directly to the patient 210 (e.g., to the bone of the patient 210). The surgical robot system 100 may also utilize a camera 200, for example, positioned on a camera stand 202. The camera stand 202 can have any suitable configuration to move, orient, and support the camera 200 in a desired position. The camera 200 may include any suitable camera or cameras, such as one or more infrared cameras (e.g., bifocal or stereophotogrammetric cameras), able to identify, for example, active and passive tracking markers 118 in a given measurement volume viewable from the perspective of the camera 200. The camera 200 may scan the given measurement volume and detect the light that comes from the markers 118 in order to identify and determine the position of the markers 118 in three-dimensions. For example, active markers 118 may include infrared-emitting markers that are activated by an electrical signal (e.g., infrared light emitting diodes (LEDs)), and passive markers 118 may include retro-reflective markers that reflect infrared light (e.g., they reflect incoming IR radiation into the direction of the incoming light), for example, emitted by illuminators on the camera 200 or other suitable device.

FIGS. 1 and 2 illustrate a potential configuration for the placement of the surgical robot system 100 in an operating room environment. For example, the robot 102 may be positioned near or next to patient 210. Although depicted near the head of the patient 210, it will be appreciated that the robot 102 can be positioned at any suitable location near the patient 210 depending on the area of the patient 210 undergoing the operation. The camera 200 may be separated from the robot system 100 and positioned at the foot of patient 210. This location allows the camera 200 to have a direct visual line of sight to the surgical field 208. Again, it is contemplated that the camera 200 may be located at any suitable position having line of sight to the surgical field 208. In the configuration shown, the surgeon 120 may be positioned across from the robot 102, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. The traditional areas for the anesthesiologist 122 and the nurse or scrub tech 124 remain unimpeded by the locations of the robot 102 and camera 200.

With respect to the other components of the robot 102, the display 110 can be attached to the surgical robot 102 and in other exemplary embodiments, display 110 can be detached from surgical robot 102, either within a surgical room with the surgical robot 102, or in a remote location. End-effector 112 may be coupled to the robot arm 104 and controlled by at least one motor. In exemplary embodiments, end-effector 112 can comprise a guide tube 114, which is able to receive and orient a surgical instrument 608 (described further herein) used to perform surgery on the patient 210. As used herein, the term "end-effector" is used interchangeably with the terms "end-effectuator" and "effectuator element." Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument 608 in a desired manner.

The surgical robot 102 is able to control the translation and orientation of the end-effector 112. The robot 102 is able to move end-effector 112 along x-, y-, and z-axes, for example. The end-effector 112 can be configured for selective rotation about one or more of the x-, y-, and z-axis, and a Z Frame axis (such that one or more of the Euler Angles (e.g., roll, pitch, and/or yaw) associated with end-effector 112 can be selectively controlled). In some exemplary embodiments, selective control of the translation and orientation of end-effector 112 can permit performance of medical procedures with significantly improved accuracy compared to conventional robots that utilize, for example, a six degree of freedom robot arm comprising only rotational axes. For example, the surgical robot system 100 may be used to operate on patient 210, and robot arm 104 can be positioned above the body of patient 210, with end-effector 112 selectively angled relative to the z-axis toward the body of patient 210.

In some exemplary embodiments, the position of the surgical instrument 608 can be dynamically updated so that surgical robot 102 can be aware of the location of the surgical instrument 608 at all times during the procedure. Consequently, in some exemplary embodiments, surgical robot 102 can move the surgical instrument 608 to the desired position quickly without any further assistance from a physician (unless the physician so desires). In some further embodiments, surgical robot 102 can be configured to correct the path of the surgical instrument 608 if the surgical instrument 608 strays from the selected, preplanned trajectory. In some exemplary embodiments, surgical robot 102 can be configured to permit stoppage, modification, and/or manual control of the movement of end-effector 112 and/or the surgical instrument 608. Thus, in use, in exemplary embodiments, a physician or other user can operate the system 100, and has the option to stop, modify, or manually control the autonomous movement of end-effector 112 and/or or the surgical instrument 608. Further details of surgical robot system 100 including the control and movement of a surgical instrument 608 by surgical robot 102 can be found in co-pending U.S. patent application Ser. No. 13/924,505, which is incorporated herein by reference in its entirety.

The robotic surgical system 100 can comprise one or more tracking markers 118 configured to track the movement of robot arm 104, end-effector 112, patient 210, and/or the surgical instrument 608 in three dimensions. In exemplary embodiments, a plurality of tracking markers 118 can be mounted (or otherwise secured) thereon to an outer surface of the robot 102, such as, for example and without limitation, on base 106 of robot 102, on robot arm 104, or on the end-effector 112. In exemplary embodiments, at least one tracking marker 118 of the plurality of tracking markers 118 can be mounted or otherwise secured to the end-effector 112. One or more tracking markers 118 can further be mounted (or otherwise secured) to the patient 210. In exemplary embodiments, the plurality of tracking markers 118 can be positioned on the patient 210 spaced apart from the surgical field 208 to reduce the likelihood of being obscured by the surgeon, surgical tools, or other parts of the robot 102. Further, one or more tracking markers 118 can be further mounted (or otherwise secured) to the surgical tools 608 (e.g., a screw driver, dilator, implant inserter, or the like). Thus, the tracking markers 118 enable each of the marked objects (e.g., the end-effector 112, the patient 210, and the surgical tools 608) to be tracked by the robot 102. In exemplary embodiments, system 100 can use tracking information collected from each of the marked objects to calculate the orientation and location, for example, of the end-effector 112, the surgical instrument 608 (e.g., positioned in the tube 114 of the end-effector 112), and the relative position of the patient 210.

The markers 118 may include radiopaque or optical markers. The markers 118 may be suitably shaped include spherical, spheroid, cylindrical, cube, cuboid, or the like. In exemplary embodiments, one or more of markers 118 may be optical markers. In some embodiments, the positioning of one or more tracking markers 118 on end-effector 112 can maximize the accuracy of the positional measurements by serving to check or verify the position of end-effector 112. Further details of surgical robot system 100 including the control, movement and tracking of surgical robot 102 and of a surgical instrument 608 can be found in co-pending U.S. patent application Ser. No. 13/924,505, which is incorporated herein by reference in its entirety.

Exemplary embodiments include one or more markers 118 coupled to the surgical instrument 608. In exemplary embodiments, these markers 118, for example, coupled to the patient 210 and surgical instruments 608, as well as markers 118 coupled to the end-effector 112 of the robot 102 can comprise conventional infrared light-emitting diodes (LEDs) or an Optotrak® diode capable of being tracked using a commercially available infrared optical tracking system such as Optotrak®. Optotrak® is a registered trademark of Northern Digital Inc., Waterloo, Ontario, Canada. In other embodiments, markers 118 can comprise conventional reflective spheres capable of being tracked using a commercially available optical tracking system such as Polaris Spectra. Polaris Spectra is also a registered trademark of Northern Digital, Inc. In an exemplary embodiment, the markers 118 coupled to the end-effector 112 are active markers which comprise infrared light-emitting diodes which may be turned on and off, and the markers 118 coupled to the patient 210 and the surgical instruments 608 comprise passive reflective spheres.

In exemplary embodiments, light emitted from and/or reflected by markers 118 can be detected by camera 200 and can be used to monitor the location and movement of the marked objects. In alternative embodiments, markers 118 can comprise a radio-frequency and/or electromagnetic reflector or transceiver and the camera 200 can include or be replaced by a radio-frequency and/or electromagnetic transceiver.

Figure 3:
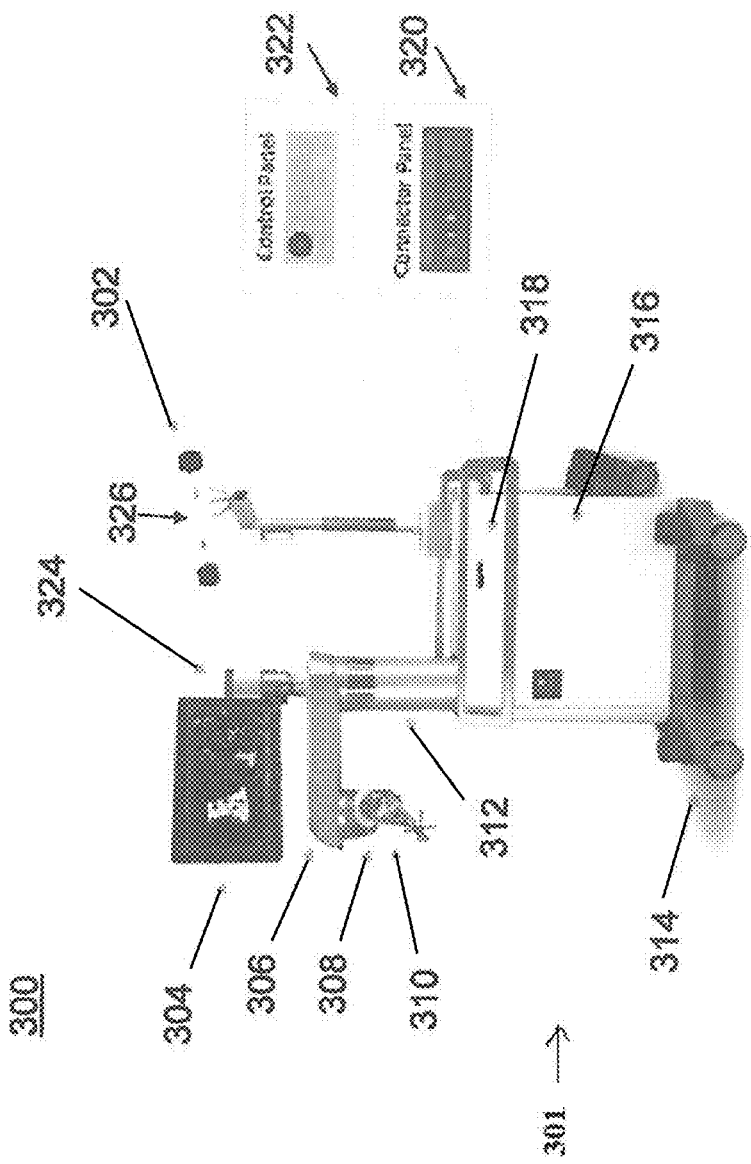
FIG. 3 illustrates a surgical robotic system in accordance with an exemplary embodiment.

Similar to surgical robot system 100, FIG. 3 illustrates a surgical robot system 300 and camera stand 302, in a docked configuration, consistent with an exemplary embodiment of the present disclosure. Surgical robot system 300 may comprise a robot 301 including a display 304, upper arm 306, lower arm 308, end-effector 310, vertical column 312, casters 314, cabinet 316, tablet drawer 318, connector panel 320, control panel 322, and ring of information 324. Camera stand 302 may comprise camera 326. These components are described in greater with respect to FIG. 5. FIG. 3 illustrates the surgical robot system 300 in a docked configuration where the camera stand 302 is nested with the robot 301, for example, when not in use. It will be appreciated by those skilled in the art that the camera 326 and robot 301 may be separated from one another and positioned at any appropriate location during the surgical procedure, for example, as shown in FIGS. 1 and 2.

Figure 4:
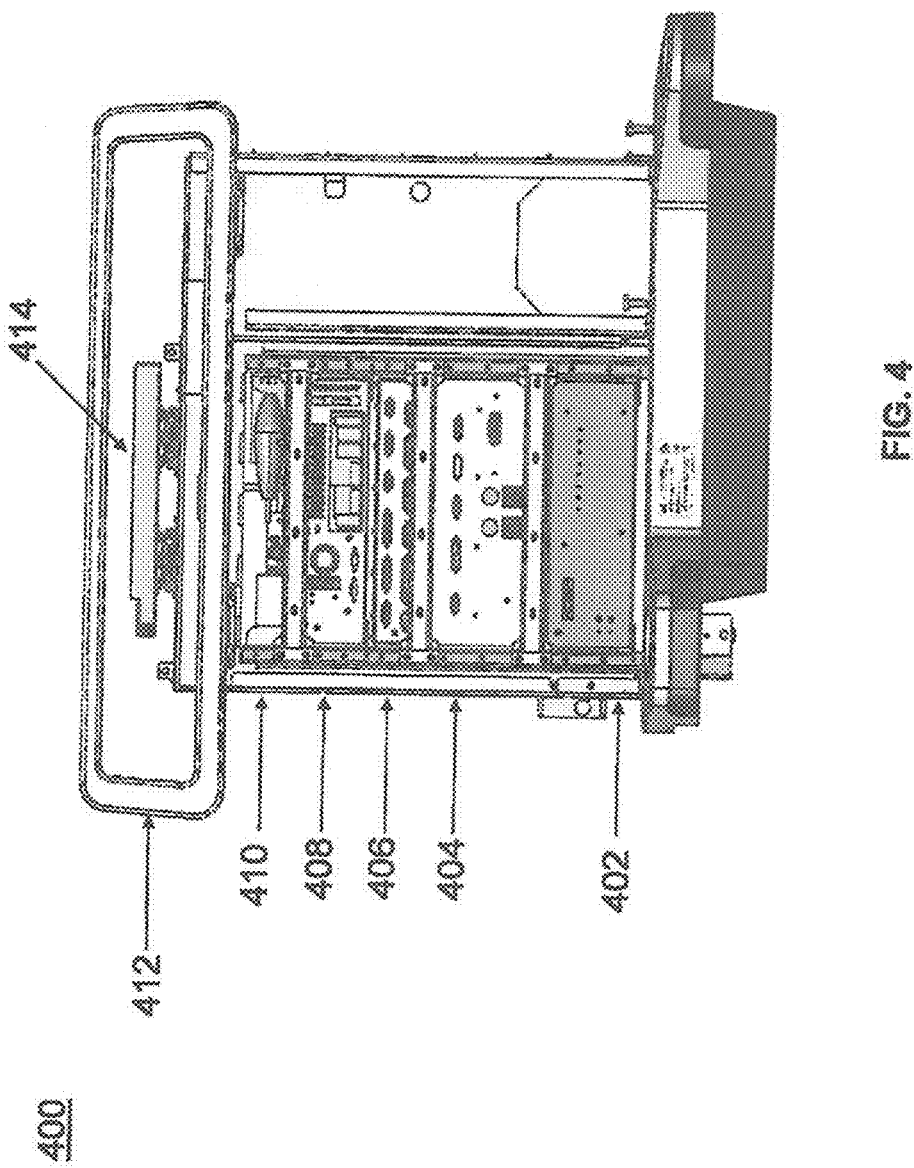
FIG. 4 illustrates a portion of a surgical robot in accordance with an exemplary embodiment.

FIG. 4 illustrates a base 400 consistent with an exemplary embodiment of the present disclosure. Base 400 may be a portion of surgical robot system 300 and comprise cabinet 316. Cabinet 316 may house certain components of surgical robot system 300 including but not limited to a battery 402, a power distribution module 404, a platform interface board module 406, a computer 408, a handle 412, and a tablet drawer 414. The connections and relationship between these components is described in greater detail with respect to FIG. 5.

Figure 5:
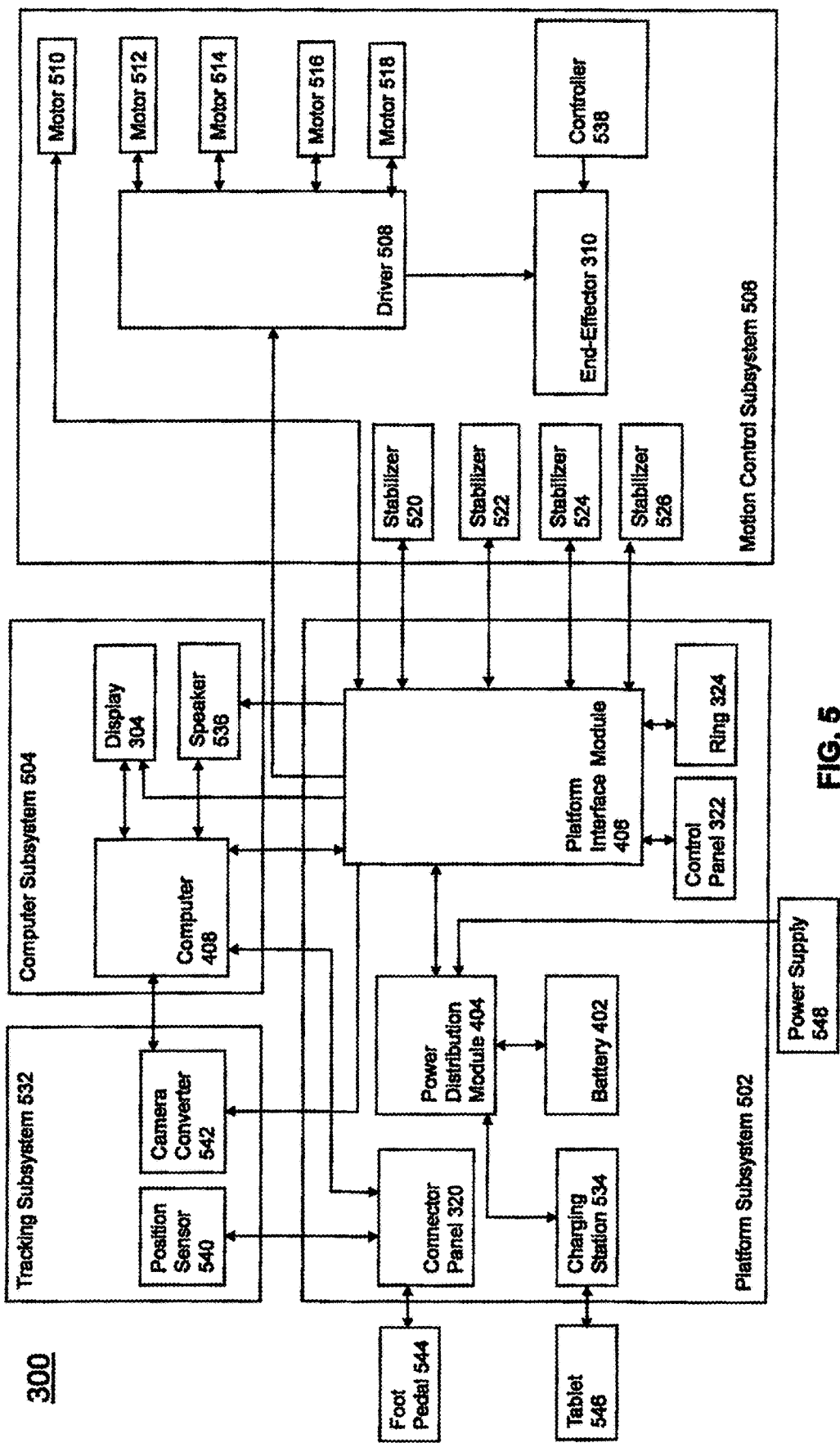
FIG. 5 illustrates a block diagram of a surgical robot in accordance with an exemplary embodiment.

FIG. 5 illustrates a block diagram of certain components of an exemplary embodiment of surgical robot system 300. Surgical robot system 300 may comprise platform subsystem 502, computer subsystem 504, motion control subsystem 506, and tracking subsystem 532. Platform subsystem 502 may further comprise battery 402, power distribution module 404, platform interface board module 406, and tablet charging station 534. Computer subsystem 504 may further comprise computer 408, display 304, and speaker 536. Motion control subsystem 506 may further comprise driver circuit 508, motors 510, 512, 514, 516, 518, stabilizers 520, 522, 524, 526, end-effector 310, and controller 538. Tracking subsystem 532 may further comprise position sensor 540 and camera converter 542. System 300 may also comprise a foot pedal 544 and tablet 546.

Input power is supplied to system 300 via a power source 548 which may be provided to power distribution module 404. Power distribution module 404 receives input power and is configured to generate different power supply voltages that are provided to other modules, components, and subsystems of system 300. Power distribution module 404 may be configured to provide different voltage supplies to platform interface module 406, which may be provided to other components such as computer 408, display 304, speaker 536, driver 508 to, for example, power motors 512, 514, 516, 518 and end-effector 310, motor 510, ring 324, camera converter 542, and other components for system 300 for example, fans for cooling the electrical components within cabinet 316.

Power distribution module 404 may also provide power to other components such as tablet charging station 534 that may be located within tablet drawer 318. Tablet charging station 534 may be in wireless or wired communication with tablet 546 for charging table 546. Tablet 546 may be used by a surgeon consistent with the present disclosure and described herein.

Power distribution module 404 may also be connected to battery 402, which serves as temporary power source in the event that power distribution module 404 does not receive power from input power 548. At other times, power distribution module 404 may serve to charge battery 402 if necessary.

Other components of platform subsystem 502 may also include connector panel 320, control panel 322, and ring 324. Connector panel 320 may serve to connect different devices and components to system 300 and/or associated components and modules. Connector panel 320 may contain one or more ports that receive lines or connections from different components. For example, connector panel 320 may have a ground terminal port that may ground system 300 to other equipment, a port to connect foot pedal 544 to system 300, a port to connect to tracking subsystem 532, which may comprise position sensor 540, camera converter 542, and cameras 326 associated with camera stand 302. Connector panel 320 may also include other ports to allow USB, Ethernet, HDMI communications to other components, such as computer 408.

Control panel 322 may provide various buttons or indicators that control operation of system 300 and/or provide information regarding system 300. For example, control panel 322 may include buttons to power on or off system 300, lift or lower vertical column 312, and lift or lower stabilizers 520-526 that may be designed to engage casters 314 to lock system 300 from physically moving. Other buttons may stop system 300 in the event of an emergency, which may remove all motor power and apply mechanical brakes to stop all motion from occurring. Control panel 322 may also have indicators notifying the user of certain system conditions such as a line power indicator or status of charge for battery 402.

Ring 324 may be a visual indicator to notify the user of system 300 of different modes that system 300 is operating under and certain warnings to the user.

Computer subsystem 504 includes computer 408, display 304, and speaker 536. Computer 504 includes an operating system and software to operate system 300. Computer 504 may receive and process information from other components (for example, tracking subsystem 532, platform subsystem 502, and/or motion control subsystem 506) in order to display information to the user. Further, computer subsystem 504 may also include speaker 536 to provide audio to the user.

Tracking subsystem 532 may include position sensor 504 and converter 542. Tracking subsystem 532 may correspond to camera stand 302 including camera 326 as described with respect to FIG. 3. Position sensor 504 may be camera 326. Tracking subsystem may track the location of certain markers that are located on the different components of system 300 and/or instruments used by a user during a surgical procedure. This tracking may be conducted in a manner consistent with the present disclosure including the use of infrared technology that tracks the location of active or passive elements, such as LEDs or reflective markers, respectively. The location, orientation, and position of structures having these types of markers may be provided to computer 408 which may be shown to a user on display 304. For example, a surgical instrument 608 having these types of markers and tracked in this manner (which may be referred to as a navigational space) may be shown to a user in relation to a three dimensional image of a patient's anatomical structure.

Motion control subsystem 506 may be configured to physically move vertical column 312, upper arm 306, lower arm 308, or rotate end-effector 310. The physical movement may be conducted through the use of one or more motors 510-518. For example, motor 510 may be configured to vertically lift or lower vertical column 312. Motor 512 may be configured to laterally move upper arm 308 around a point of engagement with vertical column 312 as shown in FIG. 3. Motor 514 may be configured to laterally move lower arm 308 around a point of engagement with upper arm 308 as shown in FIG. 3. Motors 516 and 518 may be configured to move end-effector 310 in a manner such that one may control the roll and one may control the tilt, thereby providing multiple angles that end-effector 310 may be moved. These movements may be achieved by controller 538 which may control these movements through load cells disposed on end-effector 310 and activated by a user engaging these load cells to move system 300 in a desired manner.

Moreover, system 300 may provide for automatic movement of vertical column 312, upper arm 306, and lower arm 308 through a user indicating on display 304 (which may be a touchscreen input device) the location of a surgical instrument or component on three dimensional image of the patient's anatomy on display 304. The user may initiate this automatic movement by stepping on foot pedal 544 or some other input means.

FIG. 6 illustrates a surgical robot system 600 consistent with an exemplary embodiment. Surgical robot system 600 may comprise end-effector 602, robot arm 604, guide tube 606, instrument 608, and robot base 610. Instrument tool 608 may be attached to a tracking array 612 including one or more tracking markers (such as markers 118) and have an associated trajectory 614. Trajectory 614 may represent a path of movement that instrument tool 608 is configured to travel once it is positioned through or secured in guide tube 606, for example, a path of insertion of instrument tool 608 into a patient. In an exemplary operation, robot base 610 may be configured to be in electronic communication with robot arm 604 and end-effector 602 so that surgical robot system 600 may assist a user (for example, a surgeon) in operating on the patient 210. Surgical robot system 600 may be consistent with previously described surgical robot system 100 and 300.

Figure 8:
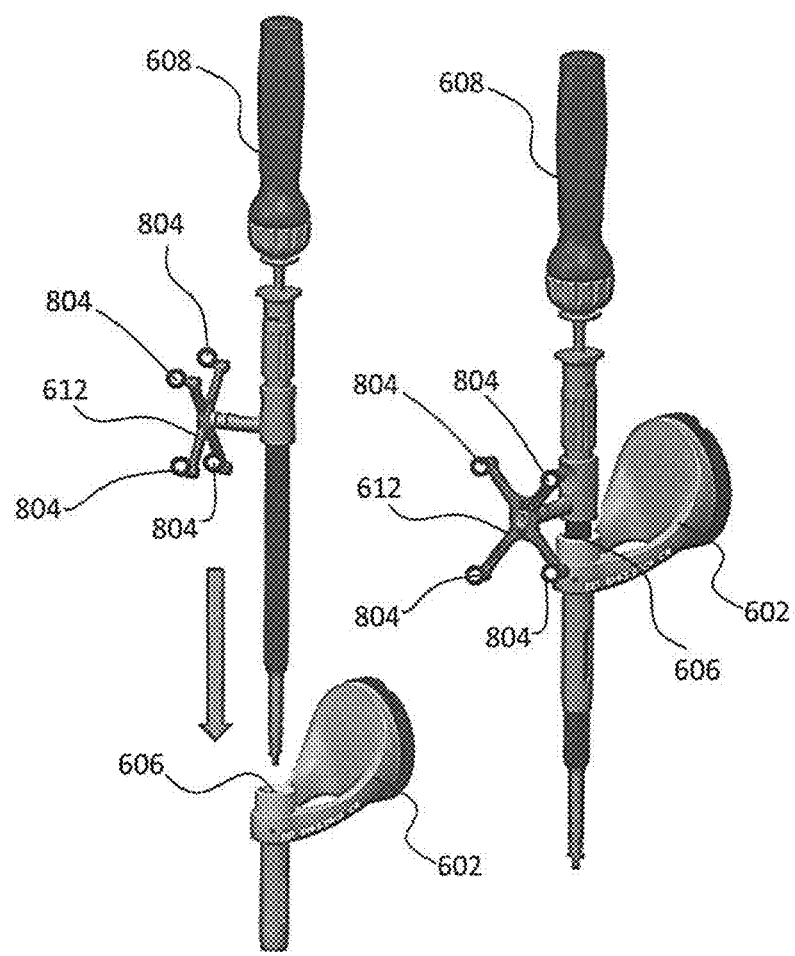
FIG. 8 illustrates a surgical instrument and the end-effector, before and after, inserting the surgical instrument into the guide tube of the end-effector according to one embodiment.

A tracking array 612 may be mounted on instrument 608 to monitor the location and orientation of instrument tool 608. The tracking array 612 may be attached to an instrument 608 and may comprise tracking markers 804. As best seen in FIG. 8, tracking markers 804 may be, for example, light emitting diodes and/or other types of reflective markers (e.g., markers 118 as described elsewhere herein). The tracking devices may be one or more line of sight devices associated with the surgical robot system. As an example, the tracking devices may be one or more cameras 200, 326 associated with the surgical robot system 100, 300 and may also track tracking array 612 for a defined domain or relative orientations of the instrument 608 in relation to the robot arm 604, the robot base 610, end-effector 602, and/or the patient 210. The tracking devices may be consistent with those structures described in connection with camera stand 302 and tracking subsystem 532.

Figure 7A:
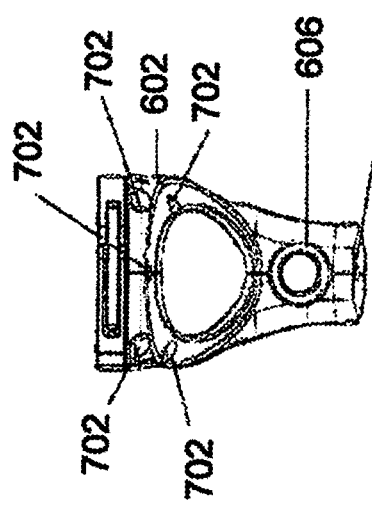
FIGS. 7A-7C illustrate an end-effector in accordance with an exemplary embodiment.
Figure 7B:
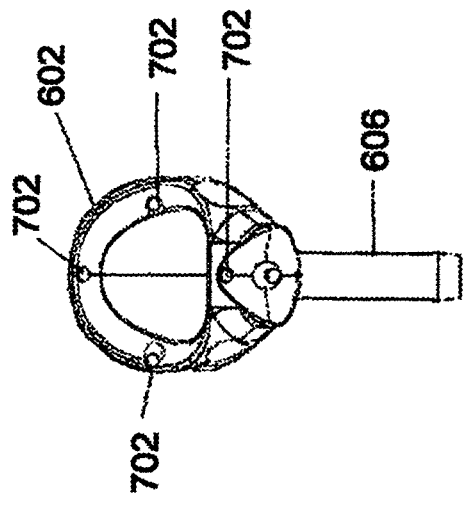
Figure 7C:
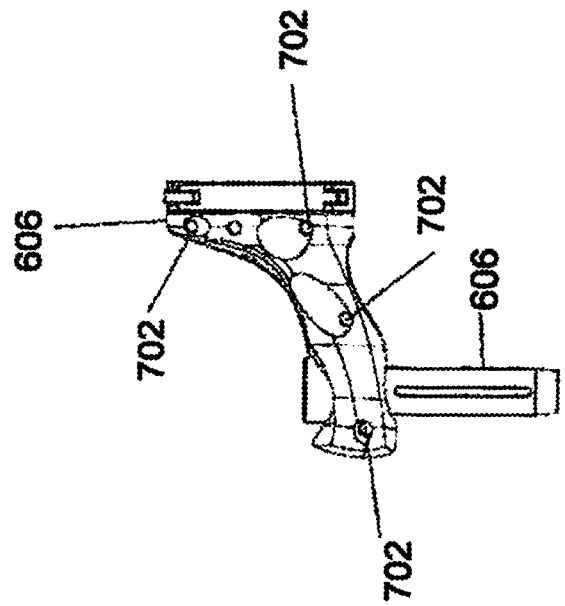

FIGS. 7A, 7B, and 7C illustrate a top view, front view, and side view, respectively, of end-effector 602 consistent with an exemplary embodiment. End-effector 602 may comprise one or more tracking markers 702. Tracking markers 702 may be light emitting diodes or other types of active and passive markers, such as tracking markers 118 that have been previously described. In an exemplary embodiment, the tracking markers 702 are active infrared-emitting markers that are activated by an electrical signal (e.g., infrared light emitting diodes (LEDs)). Thus, tracking markers 702 may be activated such that the infrared markers 702 are visible to the camera 200, 326 or may be deactivated such that the infrared markers 702 are not visible to the camera 200, 326. Thus, when the markers 702 are active, the end-effector 602 may be controlled by the system 100, 300, 600, and when the markers 702 are deactivated, the end-effector 602 may be locked in position and unable to be moved by the system 100, 300, 600.

Markers 702 may be disposed on or within end-effector 602 in a manner such that the markers 702 are visible by one or more cameras 200, 326 or other tracking devices associated with the surgical robot system 100, 300, 600. The camera 200, 326 or other tracking devices may track end-effector 602 as it moves to different positions and viewing angles by following the movement of tracking markers 702. The location of markers 702 and/or end-effector 602 may be shown on a display 110, 304 associated with the surgical robot system 100, 300, 600, for example, display 110 as shown in FIG. 2 and/or display 304 shown in FIG. 3. This display 110, 304 may allow a user to ensure that end-effector 602 is in a desirable position in relation to robot arm 604, robot base 610, the patient 210, and/or the user.

For example, as shown in FIG. 7A, markers 702 may be placed around the surface of end-effector 602 so that a tracking device placed away from the surgical field 208 and facing toward the robot 102, 301 and the camera 200, 326 is able to view at least 3 of the markers 702 through a range of common orientations of the end-effector 602 relative to the tracking device 100, 300, 600. For example, distribution of markers 702 in this way allows end-effector 602 to be monitored by the tracking devices when end-effector 602 is translated and rotated in the surgical field 208.

In addition, in exemplary embodiments, end-effector 602 may be equipped with infrared (IR) receivers that can detect when an external camera 200, 326 is getting ready to read markers 702. Upon this detection, end-effector 602 may then illuminate markers 702. The detection by the IR receivers that the external camera 200, 326 is ready to read markers 702 may signal the need to synchronize a duty cycle of markers 702, which may be light emitting diodes, to an external camera 200, 326. This may also allow for lower power consumption by the robotic system as a whole, whereby markers 702 would only be illuminated at the appropriate time instead of being illuminated continuously. Further, in exemplary embodiments, markers 702 may be powered off to prevent interference with other navigation tools, such as different types of surgical instruments 608.

FIG. 8 depicts one type of surgical instrument 608 including a tracking array 612 and tracking markers 804. Tracking markers 804 may be of any type described herein including but not limited to light emitting diodes or reflective spheres. Markers 804 are monitored by tracking devices associated with the surgical robot system 100, 300, 600 and may be one or more of the line of sight cameras 200, 326. The cameras 200, 326 may track the location of instrument 608 based on the position and orientation of tracking array 612 and markers 804. A user, such as a surgeon 120, may orient instrument 608 in a manner so that tracking array 612 and markers 804 are sufficiently recognized by the tracking device or camera 200, 326 to display instrument 608 and markers 804 on, for example, display 110 of the exemplary surgical robot system.

The manner in which a surgeon 120 may place instrument 608 into guide tube 606 of the end-effector 602 and adjust the instrument 608 is evident in FIG. 8. The hollow tube or guide tube 114, 606 of the end-effector 112, 310, 602 is sized and configured to receive at least a portion of the surgical instrument 608. The guide tube 114, 606 is configured to be oriented by the robot arm 104 such that insertion and trajectory for the surgical instrument 608 is able to reach a desired anatomical target within or upon the body of the patient 210. The surgical instrument 608 may include at least a portion of a generally cylindrical instrument. Although a screw driver is exemplified as the surgical tool 608, it will be appreciated that any suitable surgical tool 608 may be positioned by the end-effector 602. By way of example, the surgical instrument 608 may include one or more of a guide wire, cannula, a retractor, a drill, a reamer, a screw driver, an insertion tool, a removal tool, or the like. Although the hollow tube 114, 606 is generally shown as having a cylindrical configuration, it will be appreciated by those of skill in the art that the guide tube 114, 606 may have any suitable shape, size and configuration desired to accommodate the surgical instrument 608 and access the surgical site.

Figure 9:
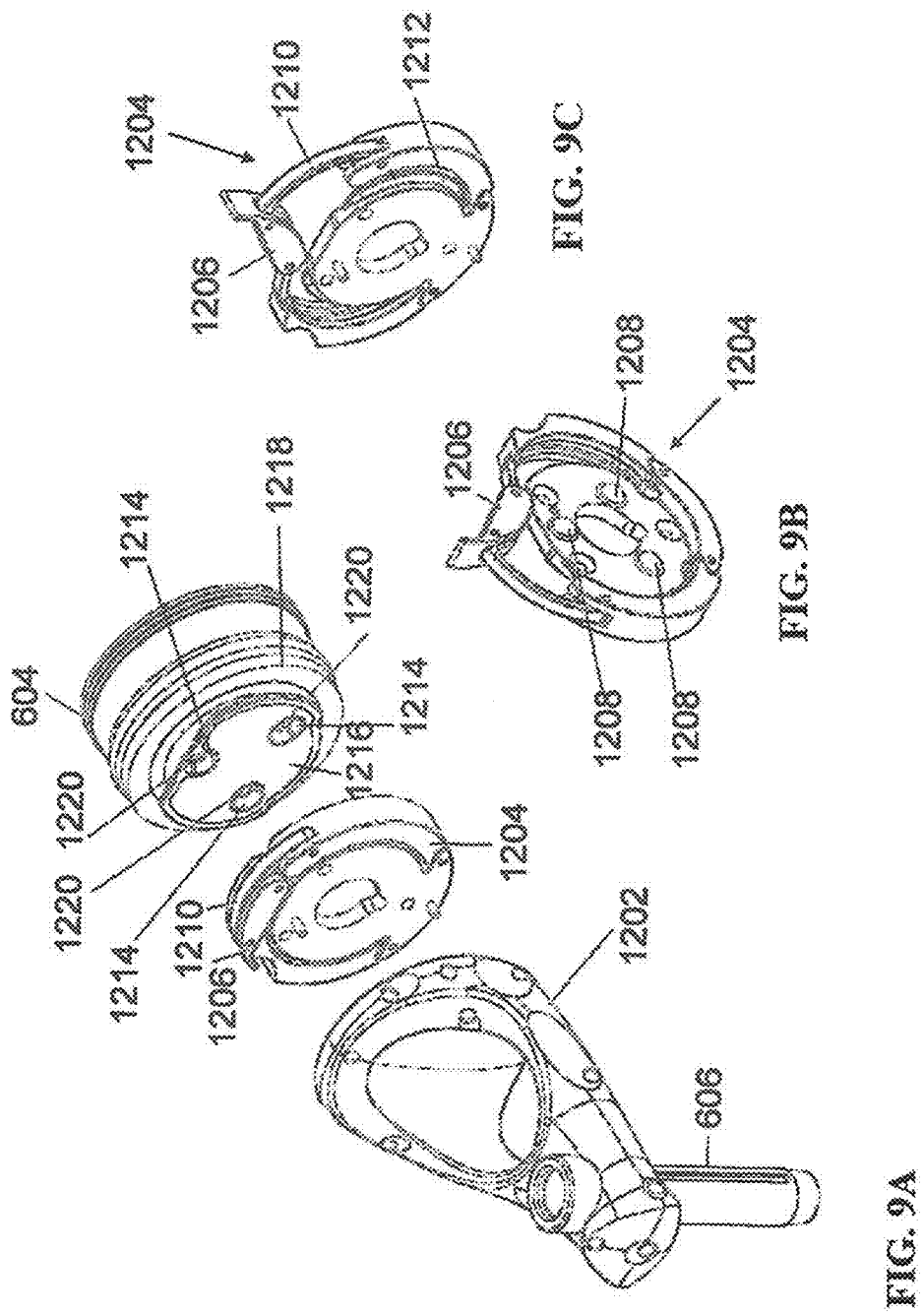
FIGS. 9A-9C illustrate portions of an end-effector and robot arm in accordance with an exemplary embodiment.

FIGS. 9A-9C illustrate end-effector 602 and a portion of robot arm 604 consistent with an exemplary embodiment. End-effector 602 may further comprise body 1202 and clamp 1204. Clamp 1204 may comprise handle 1206, balls 1208, spring 1210, and lip 1212. Robot arm 604 may further comprise depressions 1214, mounting plate 1216, lip 1218, and magnets 1220.

End-effector 602 may mechanically interface and/or engage with the surgical robot system and robot arm 604 through one or more couplings. For example, end-effector 602 may engage with robot arm 604 through a locating coupling and/or a reinforcing coupling. Through these couplings, end-effector 602 may fasten with robot arm 604 outside a flexible and sterile barrier. In an exemplary embodiment, the locating coupling may be a magnetically kinematic mount and the reinforcing coupling may be a five bar over center clamping linkage.

With respect to the locating coupling, robot arm 604 may comprise mounting plate 1216, which may be non-magnetic material, one or more depressions 1214, lip 1218, and magnets 1220. Magnet 1220 is mounted below each of depressions 1214. Portions of clamp 1204 may comprise magnetic material and be attracted by one or more magnets 1220. Through the magnetic attraction of clamp 1204 and robot arm 604, balls 1208 become seated into respective depressions 1214. For example, balls 1208 as shown in FIG. 9B would be seated in depressions 1214 as shown in FIG. 9A. This seating may be considered a magnetically-assisted kinematic coupling. Magnets 1220 may be configured to be strong enough to support the entire weight of end-effector 602 regardless of the orientation of end-effector 602. The locating coupling may be any style of kinematic mount that uniquely restrains six degrees of freedom.

With respect to the reinforcing coupling, portions of clamp 1204 may be configured to be a fixed ground link and as such clamp 1204 may serve as a five bar linkage. Closing clamp handle 1206 may fasten end-effector 602 to robot arm 604 as lip 1212 and lip 1218 engage clamp 1204 in a manner to secure end-effector 602 and robot arm 604. When clamp handle 1206 is closed, spring 1210 may be stretched or stressed while clamp 1204 is in a locked position. The locked position may be a position that provides for linkage past center. Because of a closed position that is past center, the linkage will not open absent a force applied to clamp handle 1206 to release clamp 1204. Thus, in a locked position end-effector 602 may be robustly secured to robot arm 604.

Spring 1210 may be a curved beam in tension. Spring 1210 may be comprised of a material that exhibits high stiffness and high yield strain such as virgin PEEK (polyether-ether-ketone). The linkage between end-effector 602 and robot arm 604 may provide for a sterile barrier between end-effector 602 and robot arm 604 without impeding fastening of the two couplings.

The reinforcing coupling may be a linkage with multiple spring members. The reinforcing coupling may latch with a cam or friction based mechanism. The reinforcing coupling may also be a sufficiently powerful electromagnet that will support fastening end-effector 102 to robot arm 604. The reinforcing coupling may be a multi-piece collar completely separate from either end-effector 602 and/or robot arm 604 that slips over an interface between end-effector 602 and robot arm 604 and tightens with a screw mechanism, an over center linkage, or a cam mechanism.

Figure 10:
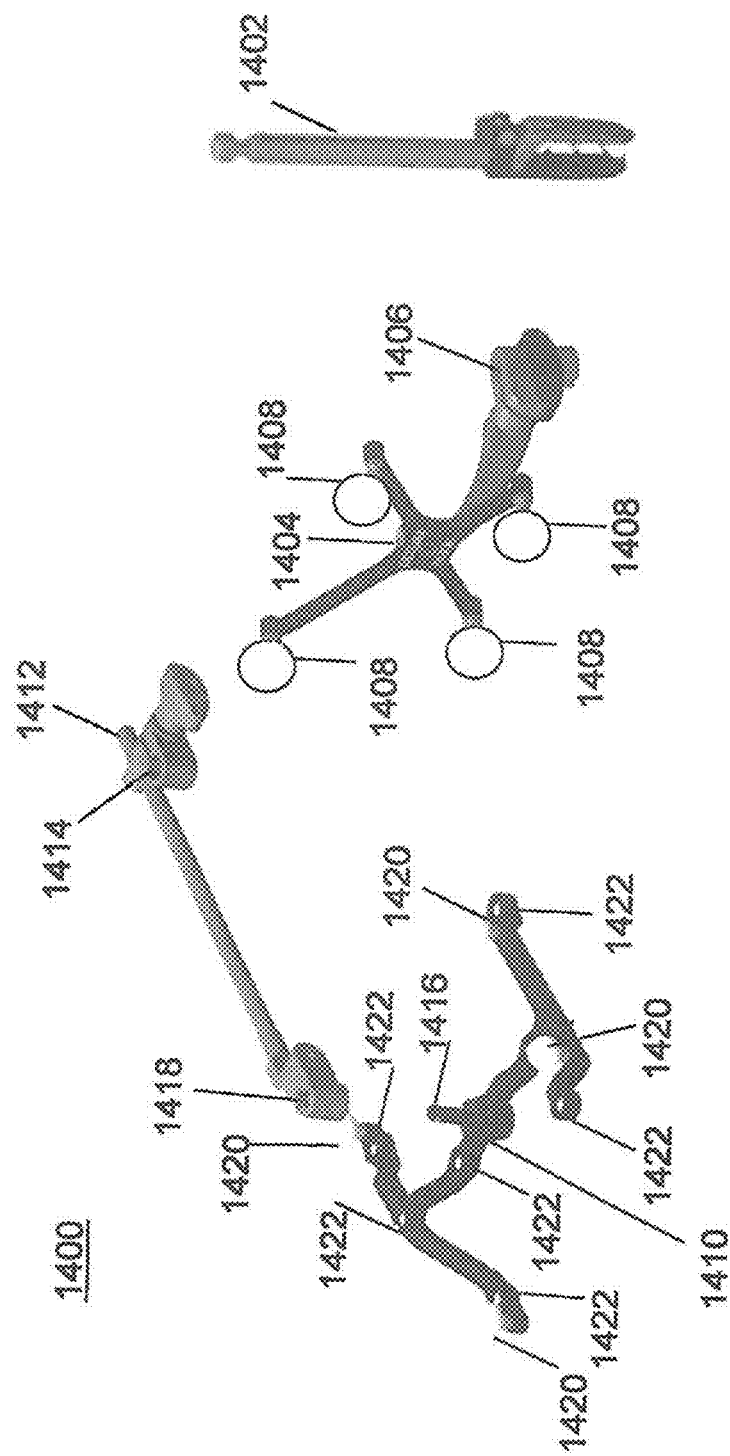
FIG. 10 illustrates a dynamic reference array, an imaging array, and other components in accordance with an exemplary embodiment.
Figure 11:
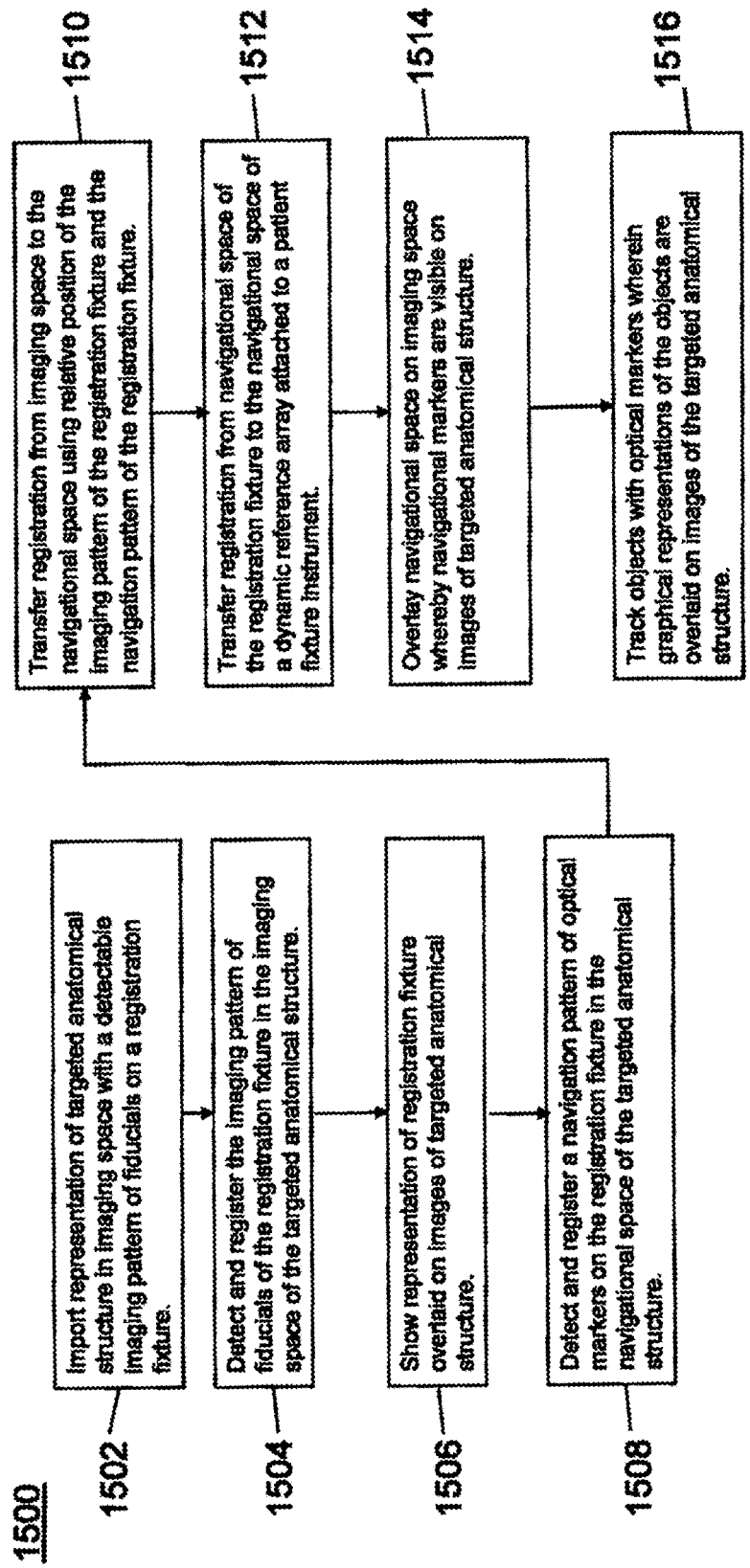
FIG. 11 illustrates a method of registration in accordance with an exemplary embodiment.

Referring to FIGS. 10 and 11, prior to or during a surgical procedure, certain registration procedures may be conducted in order to track objects and a target anatomical structure of the patient 210 both in a navigation space and an image space. In order to conduct such registration, a registration system 1400 may be used as illustrated in FIG. 10.

In order to track the position of the patient 210, a patient tracking device 116 may include a patient fixation instrument 1402 to be secured to a rigid anatomical structure of the patient 210 and a dynamic reference base (DRB) 1404 may be securely attached to the patient fixation instrument 1402. For example, patient fixation instrument 1402 may be inserted into opening 1406 of dynamic reference base 1404. Dynamic reference base 1404 may contain markers 1408 that are visible to tracking devices, such as tracking subsystem 532. These markers 1408 may be optical markers or reflective spheres, such as tracking markers 118, as previously discussed herein.

Patient fixation instrument 1402 is attached to a rigid anatomy of the patient 210 and may remain attached throughout the surgical procedure. In an exemplary embodiment, patient fixation instrument 1402 is attached to a rigid area of the patient 210, for example, a bone that is located away from the targeted anatomical structure subject to the surgical procedure. In order to track the targeted anatomical structure, dynamic reference base 1404 is associated with the targeted anatomical structure through the use of a registration fixture that is temporarily placed on or near the targeted anatomical structure in order to register the dynamic reference base 1404 with the location of the targeted anatomical structure.

A registration fixture 1410 is attached to patient fixation instrument 1402 through the use of a pivot arm 1412. Pivot arm 1412 is attached to patient fixation instrument 1402 by inserting patient fixation instrument 1402 through an opening 1414 of registration fixture 1410. Pivot arm 1412 is attached to registration fixture 1410 by, for example, inserting a knob 1416 through an opening 1418 of pivot arm 1412.

Using pivot arm 1412, registration fixture 1410 may be placed over the targeted anatomical structure and its location may be determined in an image space and navigation space using tracking markers 1420 and/or fiducials 1422 on registration fixture 1410. Registration fixture 1410 may contain a collection of markers 1420 that are visible in a navigational space (for example, markers 1420 may be detectable by tracking subsystem 532). Tracking markers 1420 may be optical markers visible in infrared light as previously described herein. Registration fixture 1410 may also contain a collection of fiducials 1422, for example, such as bearing balls, that are visible in an imaging space (for example, a three dimension CT image). As described in greater detail with respect to FIG. 11, using registration fixture 1410, the targeted anatomical structure may be associated with dynamic reference base 1404 thereby allowing depictions of objects in the navigational space to be overlaid on images of the anatomical structure. Dynamic reference base 1404, located at a position away from the targeted anatomical structure, may become a reference point thereby allowing removal of registration fixture 1410 and/or pivot arm 1412 from the surgical area.

FIG. 11 provides an exemplary method 1500 for registration consistent with the present disclosure. Method 1500 begins at step 1502 wherein a graphical representation (or image(s)) of the targeted anatomical structure may be imported into system 100, 300 600, for example computer 408. The graphical representation may be three dimensional CT or a fluoroscope scan of the targeted anatomical structure of the patient 210 which includes registration fixture 1410 and a detectable imaging pattern of fiducials 1420.

At step 1504, an imaging pattern of fiducials 1420 is detected and registered in the imaging space and stored in computer 408. Optionally, at this time at step 1506, a graphical representation of the registration fixture 1410 may be overlaid on the images of the targeted anatomical structure.

At step 1508, a navigational pattern of registration fixture 1410 is detected and registered by recognizing markers 1420. Markers 1420 may be optical markers that are recognized in the navigation space through infrared light by tracking subsystem 532 via position sensor 540. Thus, the location, orientation, and other information of the targeted anatomical structure is registered in the navigation space. Therefore, registration fixture 1410 may be recognized in both the image space through the use of fiducials 1422 and the navigation space through the use of markers 1420. At step 1510, the registration of registration fixture 1410 in the image space is transferred to the navigation space. This transferal is done, for example, by using the relative position of the imaging pattern of fiducials 1422 compared to the position of the navigation pattern of markers 1420.

At step 1512, registration of the navigation space of registration fixture 1410 (having been registered with the image space) is further transferred to the navigation space of dynamic registration array 1404 attached to patient fixture instrument 1402. Thus, registration fixture 1410 may be removed and dynamic reference base 1404 may be used to track the targeted anatomical structure in both the navigation and image space because the navigation space is associated with the image space.

At steps 1514 and 1516, the navigation space may be overlaid on the image space and objects with markers visible in the navigation space (for example, surgical instruments 608 with optical markers 804). The objects may be tracked through graphical representations of the surgical instrument 608 on the images of the targeted anatomical structure.

Figure 12A:
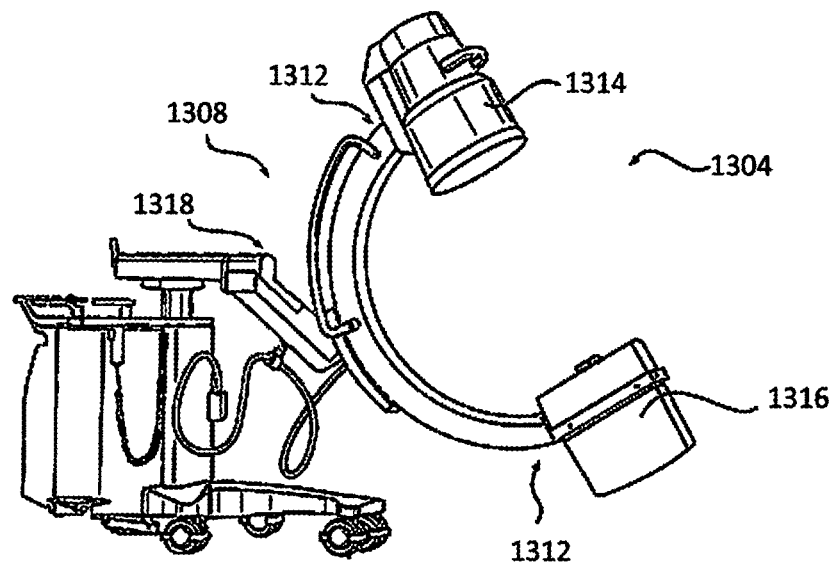
FIG. 12A-12B illustrate embodiments of imaging devices according to exemplary embodiments.
Figure 12B:
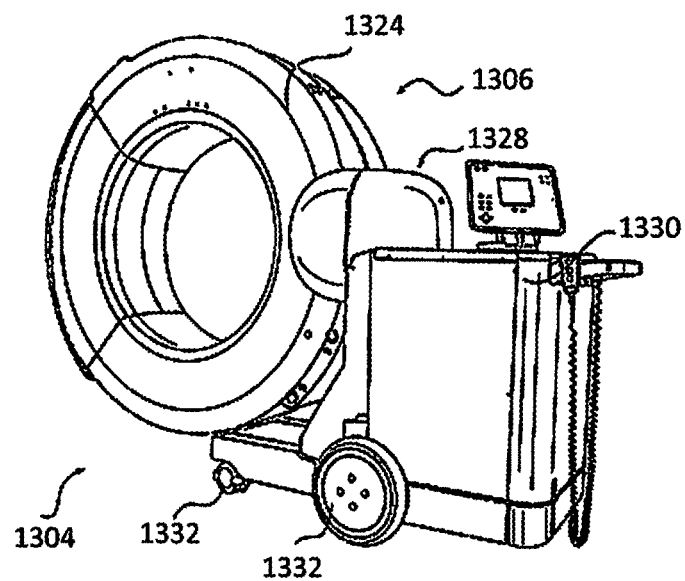

FIGS. 12A-12B illustrate imaging devices 1304 that may be used in conjunction with robot systems 100, 300, 600 to acquire pre-operative, intra-operative, post-operative, and/or real-time image data of patient 210. Any appropriate subject matter may be imaged for any appropriate procedure using the imaging system 1304. The imaging system 1304 may be any imaging device such as imaging device 1306 and/or a C-arm 1308 device. It may be desirable to take x-rays of patient 210 from a number of different positions, without the need for frequent manual repositioning of patient 210 which may be required in an x-ray system. As illustrated in FIG. 12A, the imaging system 1304 may be in the form of a C-arm 1308 that includes an elongated C-shaped member terminating in opposing distal ends 1312 of the "C" shape. C-shaped member 1130 may further comprise an x-ray source 1314 and an image receptor 1316. The space within C-arm 1308 of the arm may provide room for the physician to attend to the patient substantially free of interference from x-ray support structure 1318. As illustrated in FIG. 12B, the imaging system may include imaging device 1306 having a gantry housing 1324 attached to a support structure imaging device support structure 1328, such as a wheeled mobile cart 1330 with wheels 1332, which may enclose an image capturing portion, not illustrated. The image capturing portion may include an x-ray source and/or emission portion and an x-ray receiving and/or image receiving portion, which may be disposed about one hundred and eighty degrees from each other and mounted on a rotor (not illustrated) relative to a track of the image capturing portion. The image capturing portion may be operable to rotate three hundred and sixty degrees during image acquisition. The image capturing portion may rotate around a central point and/or axis, allowing image data of patient 210 to be acquired from multiple directions or in multiple planes. Although certain imaging systems 1304 are exemplified herein, it will be appreciated that any suitable imaging system may be selected by one of ordinary skill in the art.

Turning now to FIGS. 13A-13C, the surgical robot system 100, 300, 600 relies on accurate positioning of the end-effector 112, 602, surgical instruments 608, and/or the patient 210 (e.g., patient tracking device 116) relative to the desired surgical area. In the embodiments shown in FIGS. 13A-13C, the tracking markers 118, 804 are rigidly attached to a portion of the instrument 608 and/or end-effector 112.

FIG. 13A depicts part of the surgical robot system 100 with the robot 102 including base 106, robot arm 104, and end-effector 112. The other elements, not illustrated, such as the display, cameras, etc. may also be present as described herein. FIG. 13B depicts a close-up view of the end-effector 112 with guide tube 114 and a plurality of tracking markers 118 rigidly affixed to the end-effector 112. In this embodiment, the plurality of tracking markers 118 are attached to the guide tube 112. FIG. 13C depicts an instrument 608 (in this case, a probe 608A) with a plurality of tracking markers 804 rigidly affixed to the instrument 608. As described elsewhere herein, the instrument 608 could include any suitable surgical instrument, such as, but not limited to, guide wire, cannula, a retractor, a drill, a reamer, a screw driver, an insertion tool, a removal tool, or the like.

When tracking an instrument 608, end-effector 112, or other object to be tracked in 3D, an array of tracking markers 118, 804 may be rigidly attached to a portion of the tool 608 or end-effector 112. Preferably, the tracking markers 118, 804 are attached such that the markers 118, 804 are out of the way (e.g., not impeding the surgical operation, visibility, etc.). The markers 118, 804 may be affixed to the instrument 608, end-effector 112, or other object to be tracked, for example, with an array 612. Usually three or four markers 118, 804 are used with an array 612. The array 612 may include a linear section, a cross piece, and may be asymmetric such that the markers 118, 804 are at different relative positions and locations with respect to one another. For example, as shown in FIG. 13C, a probe 608A with a 4-marker tracking array 612 is shown, and FIG. 13B depicts the end-effector 112 with a different 4-marker tracking array 612.

In FIG. 13C, the tracking array 612 functions as the handle 620 of the probe 608A. Thus, the four markers 804 are attached to the handle 620 of the probe 608A, which is out of the way of the shaft 622 and tip 624. Stereophotogrammetric tracking of these four markers 804 allows the instrument 608 to be tracked as a rigid body and for the tracking system 100, 300, 600 to precisely determine the position of the tip 624 and the orientation of the shaft 622 while the probe 608A is moved around in front of tracking cameras 200, 326.

To enable automatic tracking of one or more tools 608, end-effector 112, or other object to be tracked in 3D (e.g., multiple rigid bodies), the markers 118, 804 on each tool 608, end-effector 112, or the like, are arranged asymmetrically with a known inter-marker spacing. The reason for asymmetric alignment is so that it is unambiguous which marker 118, 804 corresponds to a particular location on the rigid body and whether markers 118, 804 are being viewed from the front or back, i.e., mirrored. For example, if the markers 118, 804 were arranged in a square on the tool 608 or end-effector 112, it would be unclear to the system 100, 300, 600 which marker 118, 804 corresponded to which corner of the square. For example, for the probe 608A, it would be unclear which marker 804 was closest to the shaft 622. Thus, it would be unknown which way the shaft 622 was extending from the array 612. Accordingly, each array 612 and thus each tool 608, end-effector 112, or other object to be tracked should have a unique marker pattern to allow it to be distinguished from other tools 608 or other objects being tracked. Asymmetry and unique marker patterns allow the system 100, 300, 600 to detect individual markers 118, 804 then to check the marker spacing against a stored template to determine which tool 608, end effector 112, or other object they represent. Detected markers 118, 804 can then be sorted automatically and assigned to each tracked object in the correct order. Without this information, rigid body calculations could not then be performed to extract key geometric information, for example, such as tool tip 624 and alignment of the shaft 622, unless the user manually specified which detected marker 118, 804 corresponded to which position on each rigid body. These concepts are commonly known to those skilled in the methods of 3D optical tracking.

Figures 14A, 14B:
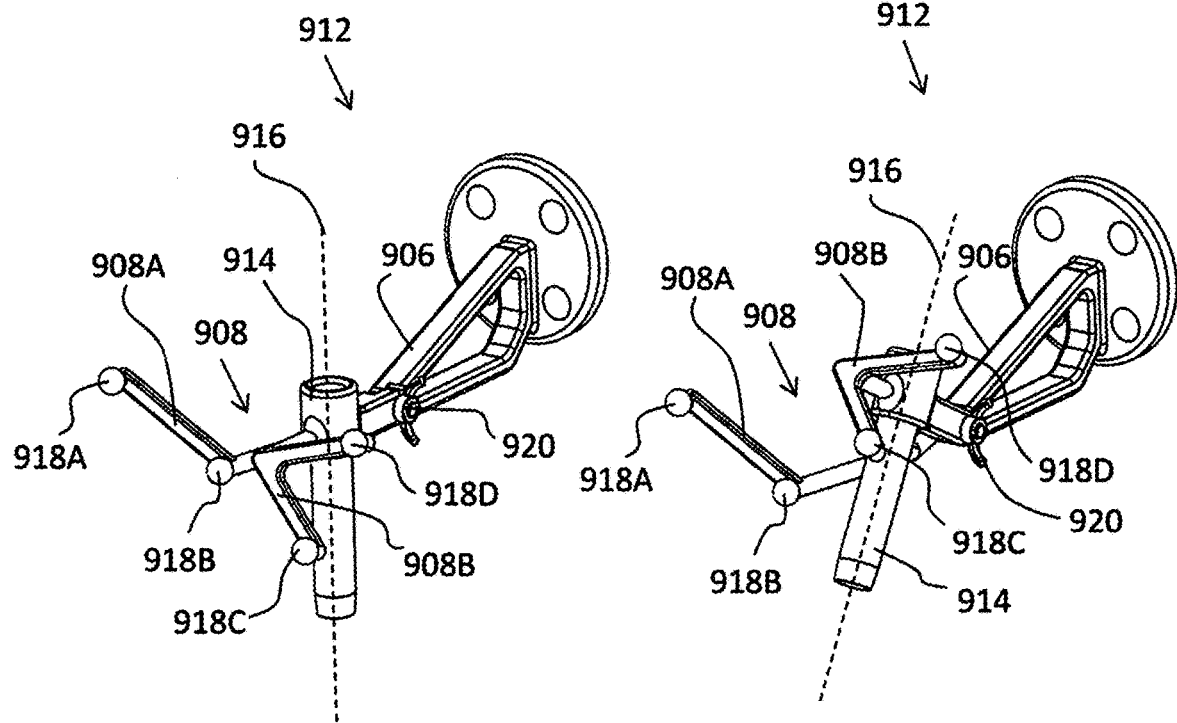
FIG. 14A is an alternative version of an end-effector with moveable tracking markers in a first configuration.
FIG. 14B is the end-effector shown in FIG. 14A with the moveable tracking markers in a second configuration.
Figure 14C:
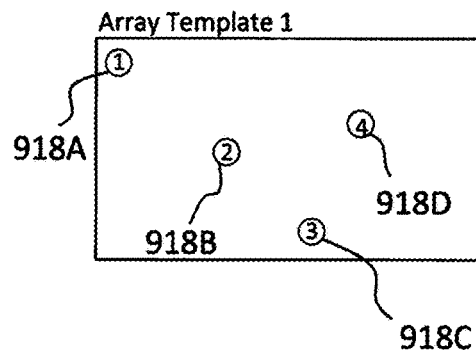
FIG. 14C shows the template of tracking markers in the first configuration from FIG. 14A.
Figure 14D:
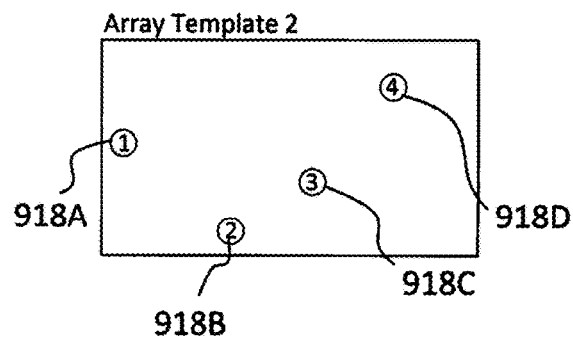
FIG. 14D shows the template of tracking markers in the second configuration from FIG. 14B.

Turning now to FIGS. 14A-14D, an alternative version of an end-effector 912 with moveable tracking markers 918A-918D is shown. In FIG. 14A, an array with moveable tracking markers 918A-918D are shown in a first configuration, and in FIG. 14B the moveable tracking markers 918A-918D are shown in a second configuration, which is angled relative to the first configuration. FIG. 14C shows the template of the tracking markers 918A-918D, for example, as seen by the cameras 200, 326 in the first configuration of FIG. 14A; and FIG. 14D shows the template of tracking markers 918A-918D, for example, as seen by the cameras 200, 326 in the second configuration of FIG. 14B.

In this embodiment, 4-marker array tracking is contemplated wherein the markers 918A-918D are not all in fixed position relative to the rigid body and instead, one or more of the array markers 918A-918D can be adjusted, for example, during testing, to give updated information about the rigid body that is being tracked without disrupting the process for automatic detection and sorting of the tracked markers 918A-918D.

When tracking any tool, such as a guide tube 914 connected to the end effector 912 of a robot system 100, 300, 600, the tracking array's primary purpose is to update the position of the end effector 912 in the camera coordinate system. When using the rigid system, for example, as shown in FIG. 13B, the array 612 of reflective markers 118 rigidly extend from the guide tube 114. Because the tracking markers 118 are rigidly connected, knowledge of the marker locations in the camera coordinate system also provides exact location of the centerline, tip, and tail of the guide tube 114 in the camera coordinate system. Typically, information about the position of the end effector 112 from such an array 612 and information about the location of a target trajectory from another tracked source are used to calculate the required moves that must be input for each axis of the robot 102 that will move the guide tube 114 into alignment with the trajectory and move the tip to a particular location along the trajectory vector.

Sometimes, the desired trajectory is in an awkward or unreachable location, but if the guide tube 114 could be swiveled, it could be reached. For example, a very steep trajectory pointing away from the base 106 of the robot 102 might be reachable if the guide tube 114 could be swiveled upward beyond the limit of the pitch (wrist up-down angle) axis, but might not be reachable if the guide tube 114 is attached parallel to the plate connecting it to the end of the wrist. To reach such a trajectory, the base 106 of the robot 102 might be moved or a different end effector 112 with a different guide tube attachment might be exchanged with the working end effector. Both of these solutions may be time consuming and cumbersome.

As best seen in FIGS. 14A and 14B, if the array 908 is configured such that one or more of the markers 918A-918D are not in a fixed position and instead, one or more of the markers 918A-918D can be adjusted, swiveled, pivoted, or moved, the robot 102 can provide updated information about the object being tracked without disrupting the detection and tracking process. For example, one of the markers 918A-918D may be fixed in position and the other markers 918A-918D may be moveable; two of the markers 918A-918D may be fixed in position and the other markers 918A-918D may be moveable; three of the markers 918A-918D may be fixed in position and the other marker 918A-918D may be moveable; or all of the markers 918A-918D may be moveable.

In the embodiment shown in FIGS. 14A and 14B, markers 918A, 918 B are rigidly connected directly to a base 906 of the end-effector 912, and markers 918C, 918D are rigidly connected to the tube 914. Similar to array 612, array 908 may be provided to attach the markers 918A-918D to the end-effector 912, instrument 608, or other object to be tracked. In this case, however, the array 908 is comprised of a plurality of separate components. For example, markers 918A, 918B may be connected to the base 906 with a first array 908A, and markers 918C, 918D may be connected to the guide tube 914 with a second array 908B. Marker 918A may be affixed to a first end of the first array 908A and marker 918B may be separated a linear distance and affixed to a second end of the first array 908A. While first array 908 is substantially linear, second array 908B has a bent or V-shaped configuration, with respective root ends, connected to the guide tube 914, and diverging therefrom to distal ends in a V-shape with marker 918C at one distal end and marker 918D at the other distal end. Although specific configurations are exemplified herein, it will be appreciated that other asymmetric designs including different numbers and types of arrays 908A, 908B and different arrangements, numbers, and types of markers 918A-918D are contemplated.

The guide tube 914 may be moveable, swivelable, or pivotable relative to the base 906, for example, across a hinge 920 or other connector to the base 906. Thus, markers 918C, 918D are moveable such that when the guide tube 914 pivots, swivels, or moves, markers 918C, 918D also pivot, swivel, or move. As best seen in FIG. 14A, guide tube 914 has a longitudinal axis 916 which is aligned in a substantially normal or vertical orientation such that markers 918A-918D have a first configuration. Turning now to FIG. 14B, the guide tube 914 is pivoted, swiveled, or moved such that the longitudinal axis 916 is now angled relative to the vertical orientation such that markers 918A-918D have a second configuration, different from the first configuration.

In contrast to the embodiment described for FIGS. 14A-14D, if a swivel existed between the guide tube 914 and the arm 104 (e.g., the wrist attachment) with all four markers 918A-918D remaining attached rigidly to the guide tube 914 and this swivel was adjusted by the user, the robotic system 100, 300, 600 would not be able to automatically detect that the guide tube 914 orientation had changed. The robotic system 100, 300, 600 would track the positions of the marker array 908 and would calculate incorrect robot axis moves assuming the guide tube 914 was attached to the wrist (the robot arm 104) in the previous orientation. By keeping one or more markers 918A-918D (e.g., two markers 918C, 918D) rigidly on the tube 914 and one or more markers 918A-918D (e.g., two markers 918A, 918B) across the swivel, automatic detection of the new position becomes possible and correct robot moves are calculated based on the detection of a new tool or end-effector 112, 912 on the end of the robot arm 104.

One or more of the markers 918A-918D are configured to be moved, pivoted, swiveled, or the like according to any suitable means. For example, the markers 918A-918D may be moved by a hinge 920, such as a clamp, spring, lever, slide, toggle, or the like, or any other suitable mechanism for moving the markers 918A-918D individually or in combination, moving the arrays 908A, 908B individually or in combination, moving any portion of the end-effector 912 relative to another portion, or moving any portion of the tool 608 relative to another portion.

As shown in FIGS. 14A and 14B, the array 908 and guide tube 914 may become reconfigurable by simply loosening the clamp or hinge 920, moving part of the array 908A, 908B relative to the other part 908A, 908B, and retightening the hinge 920 such that the guide tube 914 is oriented in a different position. For example, two markers 918C, 918D may be rigidly interconnected with the tube 914 and two markers 918A, 918B may be rigidly interconnected across the hinge 920 to the base 906 of the end-effector 912 that attaches to the robot arm 104. The hinge 920 may be in the form of a clamp, such as a wing nut or the like, which can be loosened and retightened to allow the user to quickly switch between the first configuration (FIG. 14A) and the second configuration (FIG. 14B).

The cameras 200, 326 detect the markers 918A-918D, for example, in one of the templates identified in FIGS. 14C and 14D. If the array 908 is in the first configuration (FIG. 14A) and tracking cameras 200, 326 detect the markers 918A-918D, then the tracked markers match Array Template 1 as shown in FIG. 14C. If the array 908 is the second configuration (FIG. 14B) and tracking cameras 200, 326 detect the same markers 918A-918D, then the tracked markers match Array Template 2 as shown in FIG. 14D. Array Template 1 and Array Template 2 are recognized by the system 100, 300, 600 as two distinct tools, each with its own uniquely defined spatial relationship between guide tube 914, markers 918A-918D, and robot attachment. The user could therefore adjust the position of the end-effector 912 between the first and second configurations without notifying the system 100, 300, 600 of the change and the system 100, 300, 600 would appropriately adjust the movements of the robot 102 to stay on trajectory.

In this embodiment, there are two assembly positions in which the marker array matches unique templates that allow the system 100, 300, 600 to recognize the assembly as two different tools or two different end effectors. In any position of the swivel between or outside of these two positions (namely, Array Template 1 and Array Template 2 shown in FIGS. 14C and 14D, respectively), the markers 918A-918D would not match any template and the system 100, 300, 600 would not detect any array present despite individual markers 918A-918D being detected by cameras 200, 326, with the result being the same as if the markers 918A-918D were temporarily blocked from view of the cameras 200, 326. It will be appreciated that other array templates may exist for other configurations, for example, identifying different instruments 608 or other end-effectors 112, 912, etc.

In the embodiment described, two discrete assembly positions are shown in FIGS. 14A and 14B. It will be appreciated, however, that there could be multiple discrete positions on a swivel joint, linear joint, combination of swivel and linear joints, pegboard, or other assembly where unique marker templates may be created by adjusting the position of one or more markers 918A-918D of the array relative to the others, with each discrete position matching a particular template and defining a unique tool 608 or end-effector 112, 912 with different known attributes. In addition, although exemplified for end effector 912, it will be appreciated that moveable and fixed markers 918A-918D may be used with any suitable instrument 608 or other object to be tracked.

When using an external 3D tracking system 100, 300, 600 to track a full rigid body array of three or more markers attached to a robot's end effector 112 (for example, as depicted in FIGS. 13A and 13B), it is possible to directly track or to calculate the 3D position of every section of the robot 102 in the coordinate system of the cameras 200, 326. The geometric orientations of joints relative to the tracker are known by design, and the linear or angular positions of joints are known from encoders for each motor of the robot 102, fully defining the 3D positions of all of the moving parts from the end effector 112 to the base 116. Similarly, if a tracker were mounted on the base 106 of the robot 102 (not shown), it is likewise possible to track or calculate the 3D position of every section of the robot 102 from base 106 to end effector 112 based on known joint geometry and joint positions from each motor's encoder.

In some situations, it may be desirable to track the positions of all segments of the robot 102 from fewer than three markers 118 rigidly attached to the end effector 112. Specifically, if a tool 608 is introduced into the guide tube 114, it may be desirable to track full rigid body motion of the robot 902 with only one additional marker 118 being tracked.

Turning now to FIGS. 15A-15E, an alternative version of an end-effector 1012 having only a single tracking marker 1018 is shown. End-effector 1012 may be similar to the other end-effectors described herein, and may include a guide tube 1014 extending along a longitudinal axis 1016. A single tracking marker 1018, similar to the other tracking markers described herein, may be rigidly affixed to the guide tube 1014. This single marker 1018 can serve the purpose of adding missing degrees of freedom to allow full rigid body tracking and/or can serve the purpose of acting as a surveillance marker to ensure that assumptions about robot and camera positioning are valid.

The single tracking marker 1018 may be attached to the robotic end effector 1012 as a rigid extension to the end effector 1012 that protrudes in any convenient direction and does not obstruct the surgeon's view. The tracking marker 1018 may be affixed to the guide tube 1014 or any other suitable location of on the end-effector 1012. When affixed to the guide tube 1014, the tracking marker 1018 may be positioned at a location between first and second ends of the guide tube 1014. For example, in FIG. 15A, the single tracking marker 1018 is shown as a reflective sphere mounted on the end of a narrow shaft 1017 that extends forward from the guide tube 1014 and is positioned longitudinally above a mid-point of the guide tube 1014 and below the entry of the guide tube 1014. This position allows the marker 1018 to be generally visible by cameras 200, 326 but also would not obstruct vision of the surgeon 120 or collide with other tools or objects in the vicinity of surgery. In addition, the guide tube 1014 with the marker 1018 in this position is designed for the marker array on any tool 608 introduced into the guide tube 1014 to be visible at the same time as the single marker 1018 on the guide tube 1014 is visible.

Figure 15A:
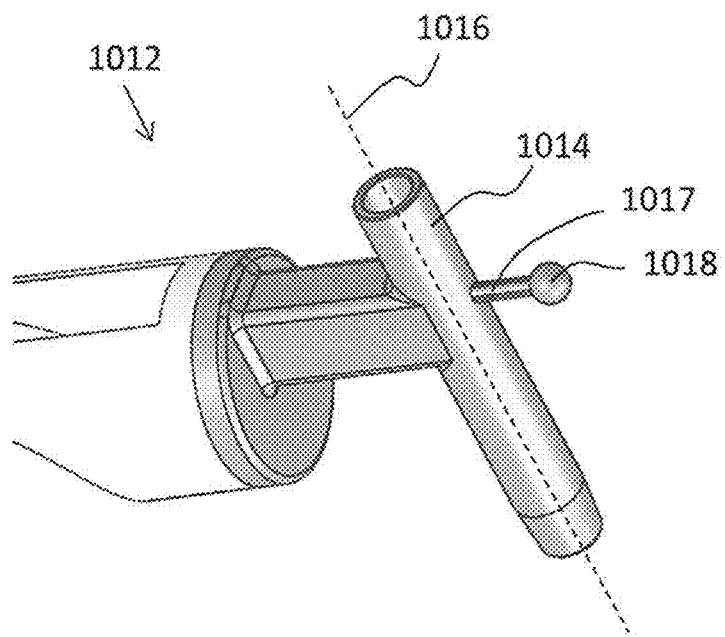
FIG. 15A shows an alternative version of the end-effector having only a single tracking marker affixed thereto.
Figure 15B:
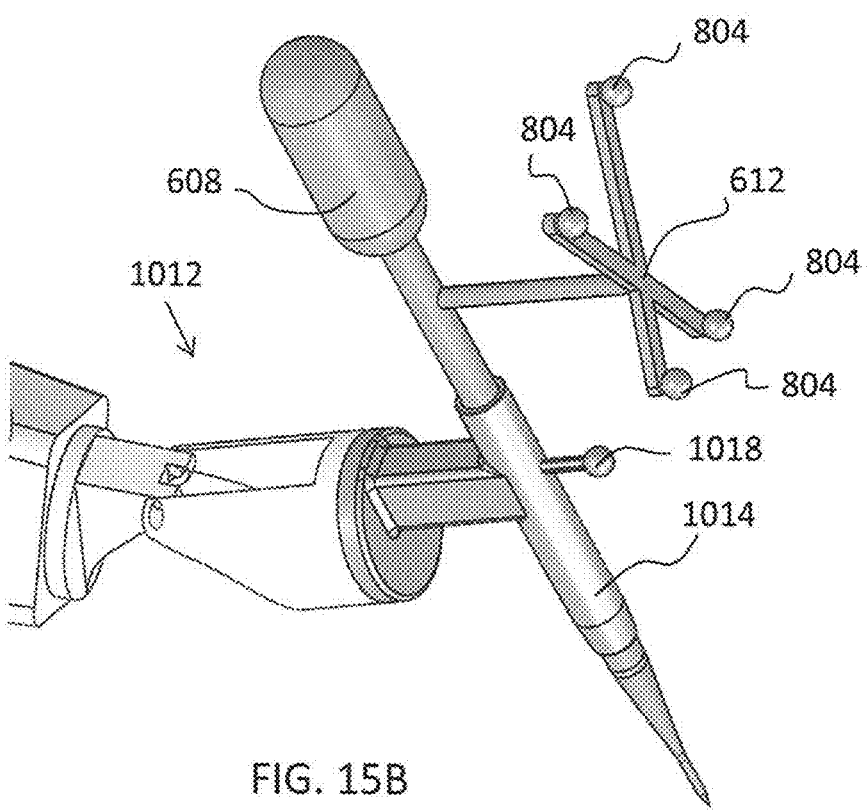
FIG. 15B shows the end-effector of FIG. 15A with an instrument disposed through the guide tube.

As shown in FIG. 15B, when a snugly fitting tool or instrument 608 is placed within the guide tube 1014, the instrument 608 becomes mechanically constrained in 4 of 6 degrees of freedom. That is, the instrument 608 cannot be rotated in any direction except about the longitudinal axis 1016 of the guide tube 1014 and the instrument 608 cannot be translated in any direction except along the longitudinal axis 1016 of the guide tube 1014. In other words, the instrument 608 can only be translated along and rotated about the centerline of the guide tube 1014. If two more parameters are known, such as (1) an angle of rotation about the longitudinal axis 1016 of the guide tube 1014; and (2) a position along the guide tube 1014, then the position of the end effector 1012 in the camera coordinate system becomes fully defined.

Figure 15C:
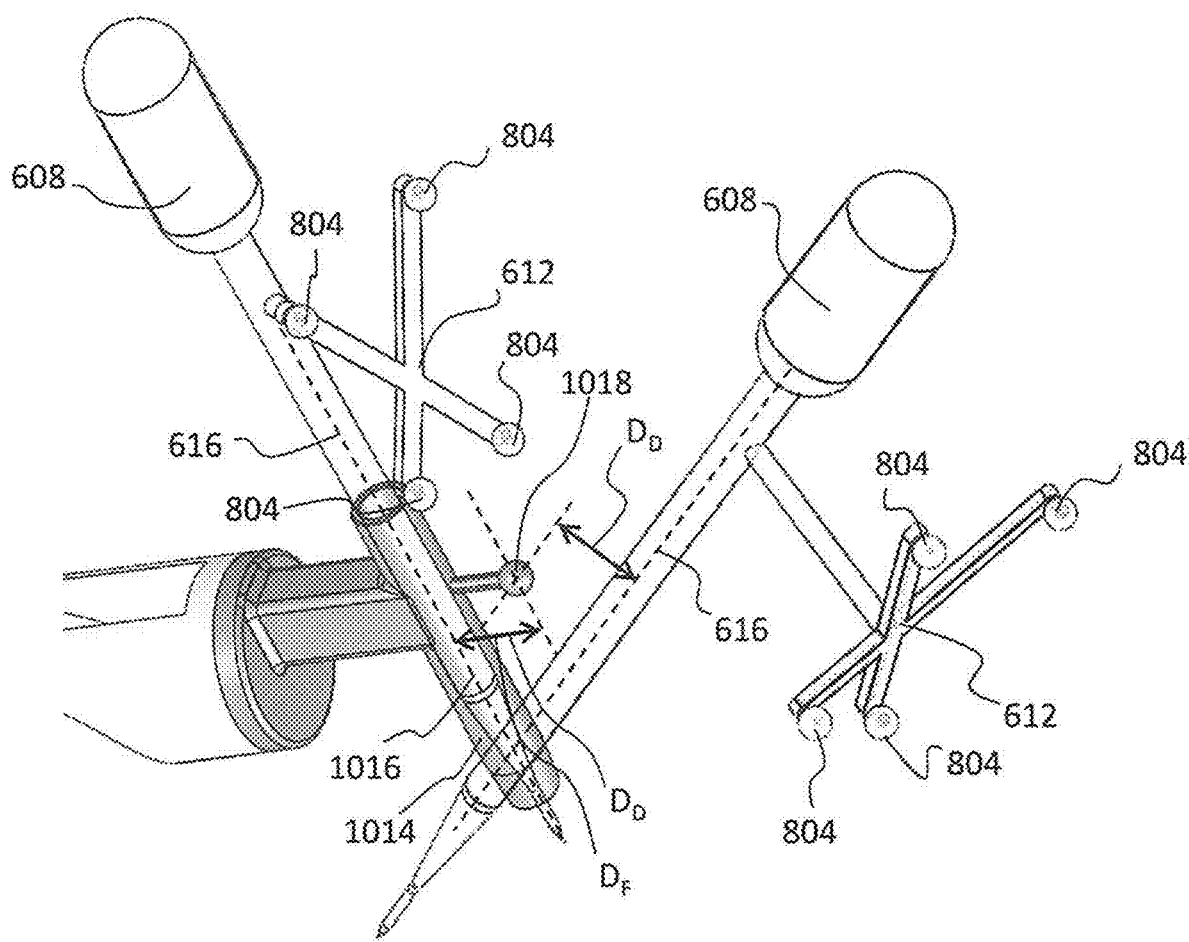
FIG. 15C shows the end-effector of FIG. 15A with the instrument in two different positions, and the resulting logic to determine if the instrument is positioned within the guide tube or outside of the guide tube.

Referring now to FIG. 15C, the system 100, 300, 600 should be able to know when a tool 608 is actually positioned inside of the guide tube 1014 and is not instead outside of the guide tube 1014 and just somewhere in view of the cameras 200, 326. The tool 608 has a longitudinal axis or centerline 616 and an array 612 with a plurality of tracked markers 804. The rigid body calculations may be used to determine where the centerline 616 of the tool 608 is located in the camera coordinate system based on the tracked position of the array 612 on the tool 608.

The fixed normal (perpendicular) distance DF from the single marker 1018 to the centerline or longitudinal axis 1016 of the guide tube 1014 is fixed and is known geometrically, and the position of the single marker 1018 can be tracked. Therefore, when a detected distance DD from tool centerline 616 to single marker 1018 matches the known fixed distance DF from the guide tube centerline 1016 to the single marker 1018, it can be determined that the tool 608 is either within the guide tube 1014 (centerlines 616, 1016 of tool 608 and guide tube 1014 coincident) or happens to be at some point in the locus of possible positions where this distance DD matches the fixed distance DF. For example, in FIG. 15C, the normal detected distance DD from tool centerline 616 to the single marker 1018 matches the fixed distance DF from guide tube centerline 1016 to the single marker 1018 in both frames of data (tracked marker coordinates) represented by the transparent tool 608 in two positions, and thus, additional considerations may be needed to determine when the tool 608 is located in the guide tube 1014.

Figure 15D:
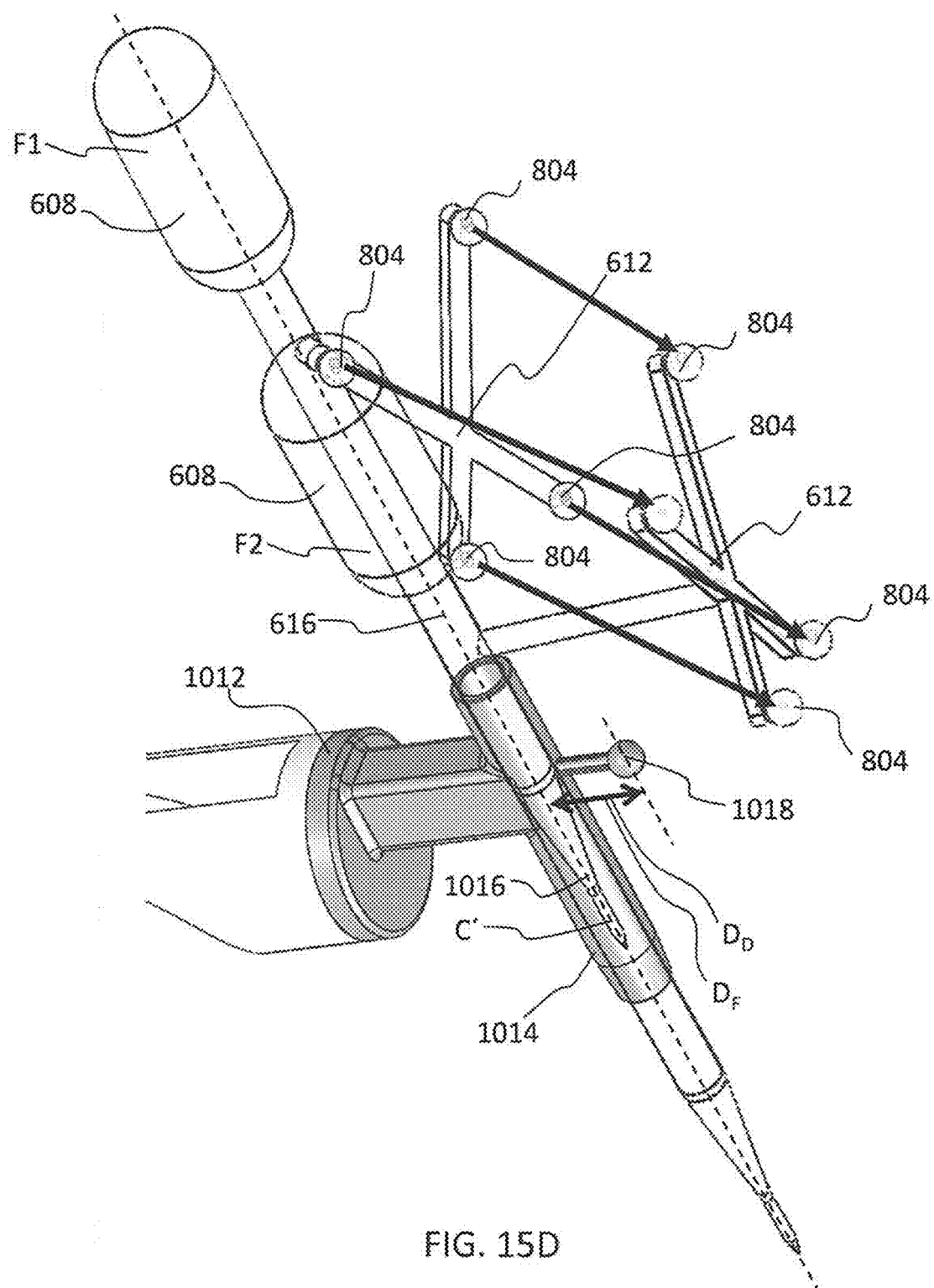
FIG. 15D shows the end-effector of FIG. 15A with the instrument in the guide tube at two different frames and its relative distance to the single tracking marker on the guide tube.

Turning now to FIG. 15D, programmed logic can be used to look for frames of tracking data in which the detected distance DD from tool centerline 616 to single marker 1018 remains fixed at the correct length despite the tool 608 moving in space by more than some minimum distance relative to the single sphere 1018 to satisfy the condition that the tool 608 is moving within the guide tube 1014. For example, a first frame F1 may be detected with the tool 608 in a first position and a second frame F2 may be detected with the tool 608 in a second position (namely, moved linearly with respect to the first position). The markers 804 on the tool array 612 may move by more than a given amount (e.g., more than 5 mm total) from the first frame F1 to the second frame F2. Even with this movement, the detected distance DD from the tool centerline vector C' to the single marker 1018 is substantially identical in both the first frame F1 and the second frame F2.

Logistically, the surgeon 120 or user could place the tool 608 within the guide tube 1014 and slightly rotate it or slide it down into the guide tube 1014 and the system 100, 300, 600 would be able to detect that the tool 608 is within the guide tube 1014 from tracking of the five markers (four markers 804 on tool 608 plus single marker 1018 on guide tube 1014). Knowing that the tool 608 is within the guide tube 1014, all 6 degrees of freedom may be calculated that define the position and orientation of the robotic end effector 1012 in space. Without the single marker 1018, even if it is known with certainty that the tool 608 is within the guide tube 1014, it is unknown where the guide tube 1014 is located along the tool's centerline vector C' and how the guide tube 1014 is rotated relative to the centerline vector C'.

Figure 15E:
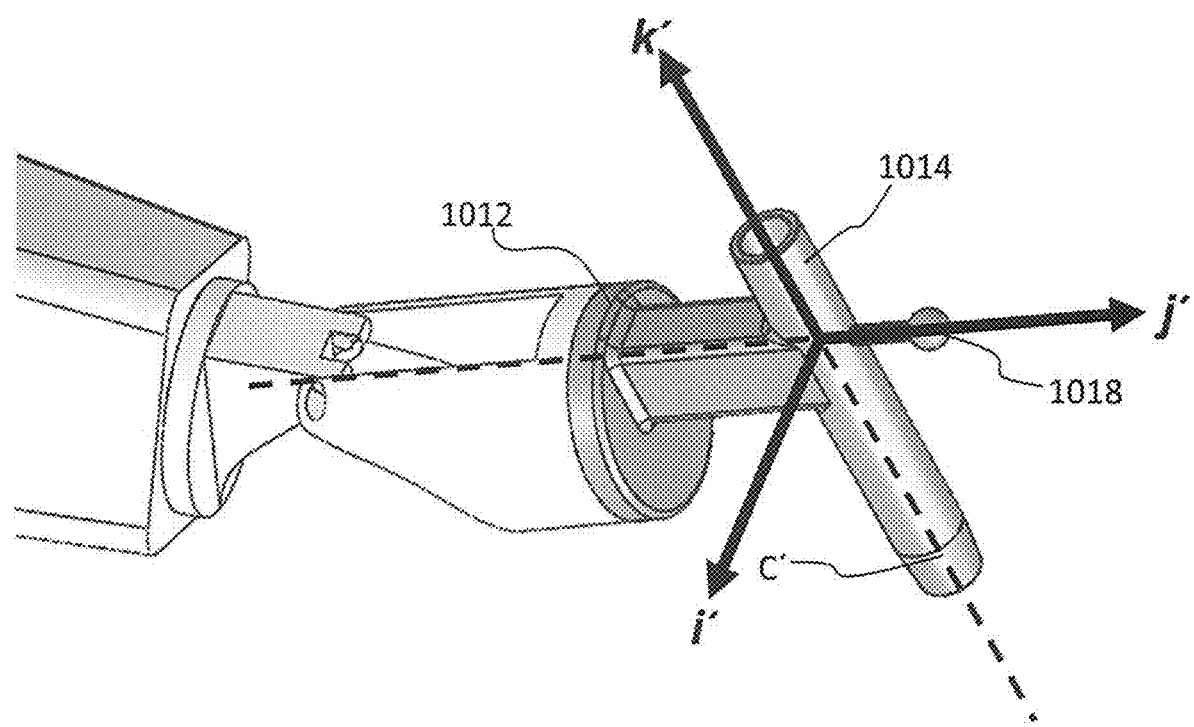
FIG. 15E shows the end-effector of FIG. 15A relative to a coordinate system.

With emphasis on FIG. 15E, the presence of the single marker 1018 being tracked as well as the four markers 804 on the tool 608, it is possible to construct the centerline vector C' of the guide tube 1014 and tool 608 and the normal vector through the single marker 1018 and through the centerline vector C'. This normal vector has an orientation that is in a known orientation relative to the forearm of the robot distal to the wrist (in this example, oriented parallel to that segment) and intersects the centerline vector C' at a specific fixed position. For convenience, three mutually orthogonal vectors k', j', i' can be constructed, as shown in FIG. 15E, defining rigid body position and orientation of the guide tube 1014. One of the three mutually orthogonal vectors k' is constructed from the centerline vector C', the second vector j' is constructed from the normal vector through the single marker 1018, and the third vector i' is the vector cross product of the first and second vectors k', j'. The robot's joint positions relative to these vectors k', j', i' are known and fixed when all joints are at zero, and therefore rigid body calculations can be used to determine the location of any section of the robot relative to these vectors k', j', i' when the robot is at a home position. During robot movement, if the positions of the tool markers 804 (while the tool 608 is in the guide tube 1014) and the position of the single marker 1018 are detected from the tracking system, and angles/linear positions of each joint are known from encoders, then position and orientation of any section of the robot can be determined.

In some embodiments, it may be useful to fix the orientation of the tool 608 relative to the guide tube 1014. For example, the end effector guide tube 1014 may be oriented in a particular position about its axis 1016 to allow machining or implant positioning. Although the orientation of anything attached to the tool 608 inserted into the guide tube 1014 is known from the tracked markers 804 on the tool 608, the rotational orientation of the guide tube 1014 itself in the camera coordinate system is unknown without the additional tracking marker 1018 (or multiple tracking markers in other embodiments) on the guide tube 1014. This marker 1018 provides essentially a "clock position" from −180° to +180° based on the orientation of the marker 1018 relative to the centerline vector C'. Thus, the single marker 1018 can provide additional degrees of freedom to allow full rigid body tracking and/or can act as a surveillance marker to ensure that assumptions about the robot and camera positioning are valid.

Figure 16:
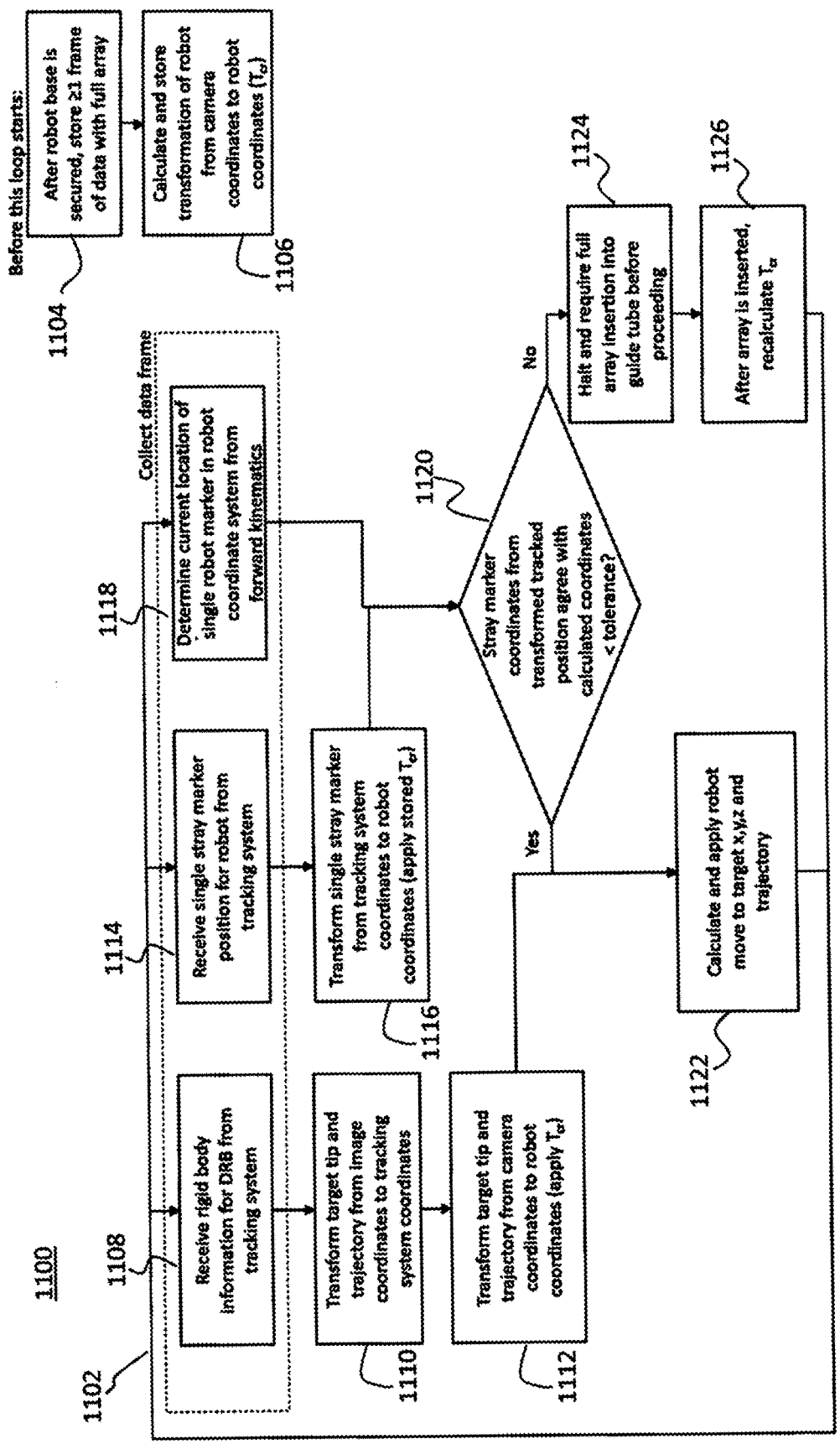
FIG. 16 is a block diagram of a method for navigating and moving the end-effector of the robot to a desired target trajectory.

FIG. 16 is a block diagram of a method 1100 for navigating and moving the end-effector 1012 (or any other end-effector described herein) of the robot 102 to a desired target trajectory. Another use of the single marker 1018 on the robotic end effector 1012 or guide tube 1014 is as part of the method 1100 enabling the automated safe movement of the robot 102 without a full tracking array attached to the robot 102. This method 1100 functions when the tracking cameras 200, 326 do not move relative to the robot 102 (i.e., they are in a fixed position), the tracking system's coordinate system and robot's coordinate system are co-registered, and the robot 102 is calibrated such that the position and orientation of the guide tube 1014 can be accurately determined in the robot's Cartesian coordinate system based only on the encoded positions of each robotic axis.

For this method 1100, the coordinate systems of the tracker and the robot must be co-registered, meaning that the coordinate transformation from the tracking system's Cartesian coordinate system to the robot's Cartesian coordinate system is needed. For convenience, this coordinate transformation can be a 4×4 matrix of translations and rotations that is well known in the field of robotics. This transformation will be termed Tcr to refer to "transformation—camera to robot". Once this transformation is known, any new frame of tracking data, which is received as x,y,z coordinates in vector form for each tracked marker, can be multiplied by the 4×4 matrix and the resulting x,y,z coordinates will be in the robot's coordinate system. To obtain Tcr, a full tracking array on the robot is tracked while it is rigidly attached to the robot at a location that is known in the robot's coordinate system, then known rigid body methods are used to calculate the transformation of coordinates. It should be evident that any tool 608 inserted into the guide tube 1014 of the robot 102 can provide the same rigid body information as a rigidly attached array when the additional marker 1018 is also read. That is, the tool 608 need only be inserted to any position within the guide tube 1014 and at any rotation within the guide tube 1014, not to a fixed position and orientation. Thus, it is possible to determine Tcr by inserting any tool 608 with a tracking array 612 into the guide tube 1014 and reading the tool's array 612 plus the single marker 1018 of the guide tube 1014 while at the same time determining from the encoders on each axis the current location of the guide tube 1014 in the robot's coordinate system.

Logic for navigating and moving the robot 102 to a target trajectory is provided in the method 1100 of FIG. 16. Before entering the loop 1102, it is assumed that the transformation Tcr was previously stored. Thus, before entering loop 1102, in step 1104, after the robot base 106 is secured, greater than or equal to one frame of tracking data of a tool inserted in the guide tube while the robot is static is stored; and in step 1106, the transformation of robot guide tube position from camera coordinates to robot coordinates Tcr is calculated from this static data and previous calibration data. Tcr should remain valid as long as the cameras 200, 326 do not move relative to the robot 102. If the cameras 200, 326 move relative to the robot 102, and Tcr needs to be re-obtained, the system 100, 300, 600 can be made to prompt the user to insert a tool 608 into the guide tube 1014 and then automatically perform the necessary calculations.

In the flowchart of method 1100, each frame of data collected consists of the tracked position of the DRB 1404 on the patient 210, the tracked position of the single marker 1018 on the end effector 1014, and a snapshot of the positions of each robotic axis. From the positions of the robot's axes, the location of the single marker 1018 on the end effector 1012 is calculated. This calculated position is compared to the actual position of the marker 1018 as recorded from the tracking system. If the values agree, it can be assured that the robot 102 is in a known location. The transformation Tcr is applied to the tracked position of the DRB 1404 so that the target for the robot 102 can be provided in terms of the robot's coordinate system. The robot 102 can then be commanded to move to reach the target.

After steps 1104, 1106, loop 1102 includes step 1108 receiving rigid body information for DRB 1404 from the tracking system; step 1110 transforming target tip and trajectory from image coordinates to tracking system coordinates; and step 1112 transforming target tip and trajectory from camera coordinates to robot coordinates (apply Tcr). Loop 1102 further includes step 1114 receiving a single stray marker position for robot from tracking system; and step 1116 transforming the single stray marker from tracking system coordinates to robot coordinates (apply stored Tcr). Loop 1102 also includes step 1118 determining current location of the single robot marker 1018 in the robot coordinate system from forward kinematics. The information from steps 1116 and 1118 is used to determine step 1120 whether the stray marker coordinates from transformed tracked position agree with the calculated coordinates being less than a given tolerance. If yes, proceed to step 1122, calculate and apply robot move to target x, y, z and trajectory. If no, proceed to step 1124, halt and require full array insertion into guide tube 1014 before proceeding; step 1126 after array is inserted, recalculate Tcr; and then proceed to repeat steps 1108, 1114, and 1118.

This method 1100 has advantages over a method in which the continuous monitoring of the single marker 1018 to verify the location is omitted. Without the single marker 1018, it would still be possible to determine the position of the end effector 1012 using Tcr and to send the end-effector 1012 to a target location but it would not be possible to verify that the robot 102 was actually in the expected location. For example, if the cameras 200, 326 had been bumped and Tcr was no longer valid, the robot 102 would move to an erroneous location. For this reason, the single marker 1018 provides value with regard to safety.

For a given fixed position of the robot 102, it is theoretically possible to move the tracking cameras 200, 326 to a new location in which the single tracked marker 1018 remains unmoved since it is a single point, not an array. In such a case, the system 100, 300, 600 would not detect any error since there would be agreement in the calculated and tracked locations of the single marker 1018. However, once the robot's axes caused the guide tube 1012 to move to a new location, the calculated and tracked positions would disagree and the safety check would be effective.

The term "surveillance marker" may be used, for example, in reference to a single marker that is in a fixed location relative to the DRB 1404. In this instance, if the DRB 1404 is bumped or otherwise dislodged, the relative location of the surveillance marker changes and the surgeon 120 can be alerted that there may be a problem with navigation. Similarly, in the embodiments described herein, with a single marker 1018 on the robot's guide tube 1014, the system 100, 300, 600 can continuously check whether the cameras 200, 326 have moved relative to the robot 102. If registration of the tracking system's coordinate system to the robot's coordinate system is lost, such as by cameras 200, 326 being bumped or malfunctioning or by the robot malfunctioning, the system 100, 300, 600 can alert the user and corrections can be made. Thus, this single marker 1018 can also be thought of as a surveillance marker for the robot 102.

It should be clear that with a full array permanently mounted on the robot 102 (e.g., the plurality of tracking markers 702 on end-effector 602 shown in FIGS. 7A-7C) such functionality of a single marker 1018 as a robot surveillance marker is not needed because it is not required that the cameras 200, 326 be in a fixed position relative to the robot 102, and Tcr is updated at each frame based on the tracked position of the robot 102. Reasons to use a single marker 1018 instead of a full array are that the full array is more bulky and obtrusive, thereby blocking the surgeon's view and access to the surgical field 208 more than a single marker 1018, and line of sight to a full array is more easily blocked than line of sight to a single marker 1018.

Turning now to FIGS. 17A-17B and 18A-18B, instruments 608, such as implant holders 608B, 608C, are depicted which include both fixed and moveable tracking markers 804, 806. The implant holders 608B, 608C may have a handle 620 and an outer shaft 622 extending from the handle 620. The shaft 622 may be positioned substantially perpendicular to the handle 620, as shown, or in any other suitable orientation. An inner shaft 626 may extend through the outer shaft 622 with a knob 628 at one end. Implant 10, 12 connects to the shaft 622, at the other end, at tip 624 of the implant holder 608B, 608C using typical connection mechanisms known to those of skill in the art. The knob 628 may be rotated, for example, to expand or articulate the implant 10, 12. U.S. Pat. Nos. 8,709,086 and 8,491,659, which are incorporated by reference herein, describe expandable fusion devices and methods of installation.

When tracking the tool 608, such as implant holder 608B, 608C, the tracking array 612 may contain a combination of fixed markers 804 and one or more moveable markers 806 which make up the array 612 or is otherwise attached to the implant holder 608B, 608C. The navigation array 612 may include at least one or more (e.g., at least two) fixed position markers 804, which are positioned with a known location relative to the implant holder instrument 608B, 608C. These fixed markers 804 would not be able to move in any orientation relative to the instrument geometry and would be useful in defining where the instrument 608 is in space. In addition, at least one marker 806 is present which can be attached to the array 612 or the instrument itself which is capable of moving within a pre-determined boundary (e.g., sliding, rotating, etc.) relative to the fixed markers 804. The system 100, 300, 600 (e.g., the software) correlates the position of the moveable marker 806 to a particular position, orientation, or other attribute of the implant 10 (such as height of an expandable interbody spacer shown in FIGS. 17A-17B or angle of an articulating interbody spacer shown in FIGS. 18A-18B). Thus, the system and/or the user can determine the height or angle of the implant 10, 12 based on the location of the moveable marker 806.

Figure 17A:
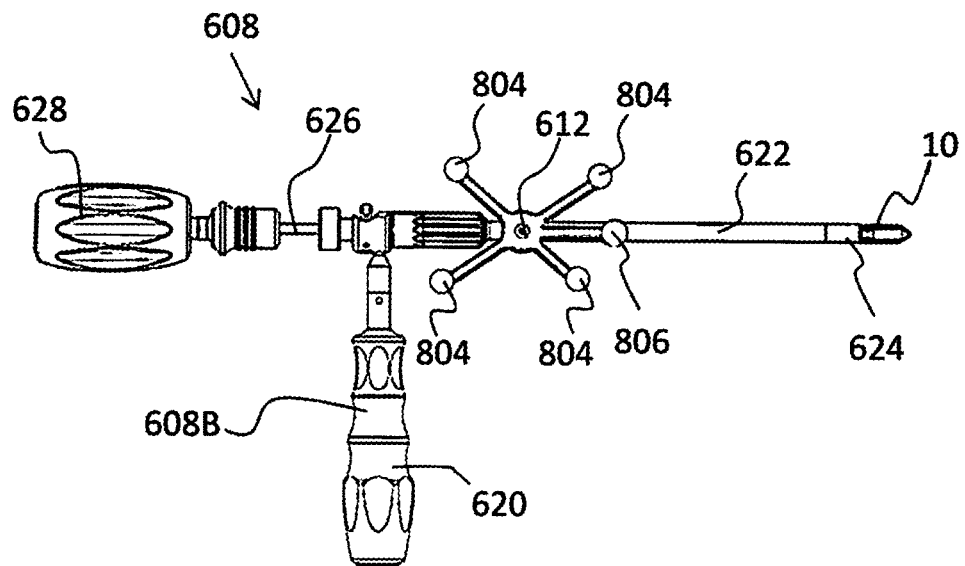
FIGS. 17A-17B depict an instrument for inserting an expandable implant having fixed and moveable tracking markers in contracted and expanded positions, respectively.
Figure 17B:
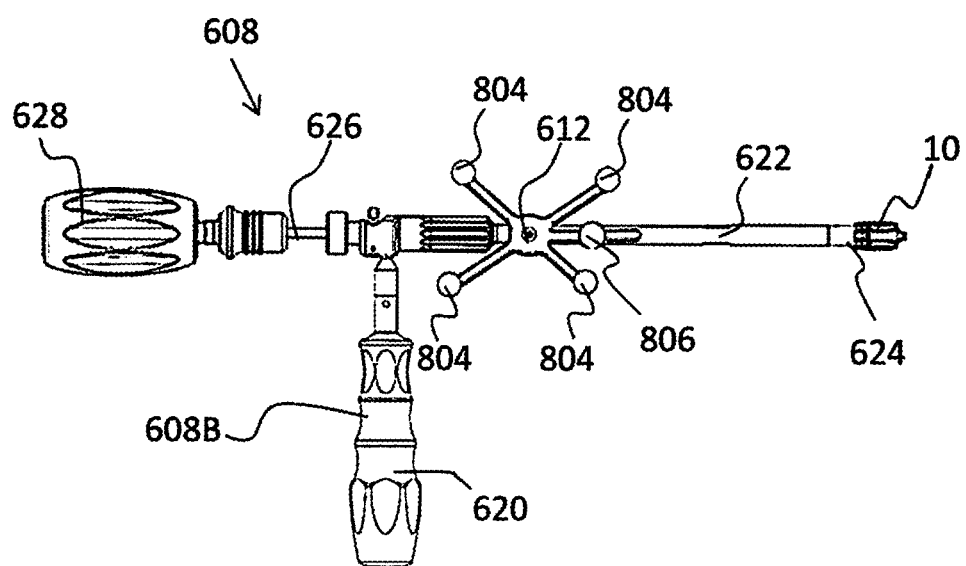

In the embodiment shown in FIGS. 17A-17B, four fixed markers 804 are used to define the implant holder 608B and a fifth moveable marker 806 is able to slide within a pre-determined path to provide feedback on the implant height (e.g., a contracted position or an expanded position). FIG. 17A shows the expandable spacer 10 at its initial height, and FIG. 17B shows the spacer 10 in the expanded state with the moveable marker 806 translated to a different position. In this case, the moveable marker 806 moves closer to the fixed markers 804 when the implant 10 is expanded, although it is contemplated that this movement may be reversed or otherwise different. The amount of linear translation of the marker 806 would correspond to the height of the implant 10. Although only two positions are shown, it would be possible to have this as a continuous function whereby any given expansion height could be correlated to a specific position of the moveable marker 806.

Figure 18A:
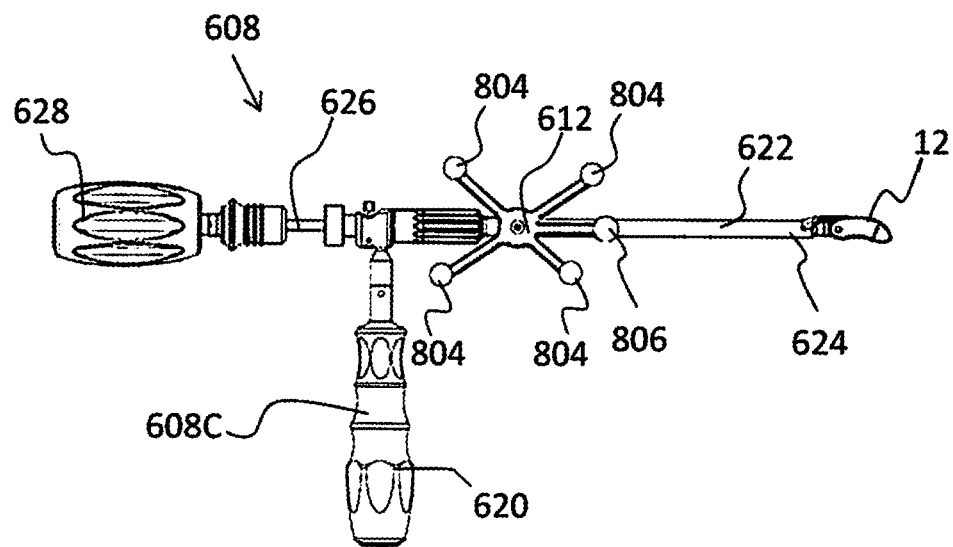
FIGS. 18A-18B depict an instrument for inserting an articulating implant having fixed and moveable tracking markers in insertion and angled positions, respectively.
Figure 18B:
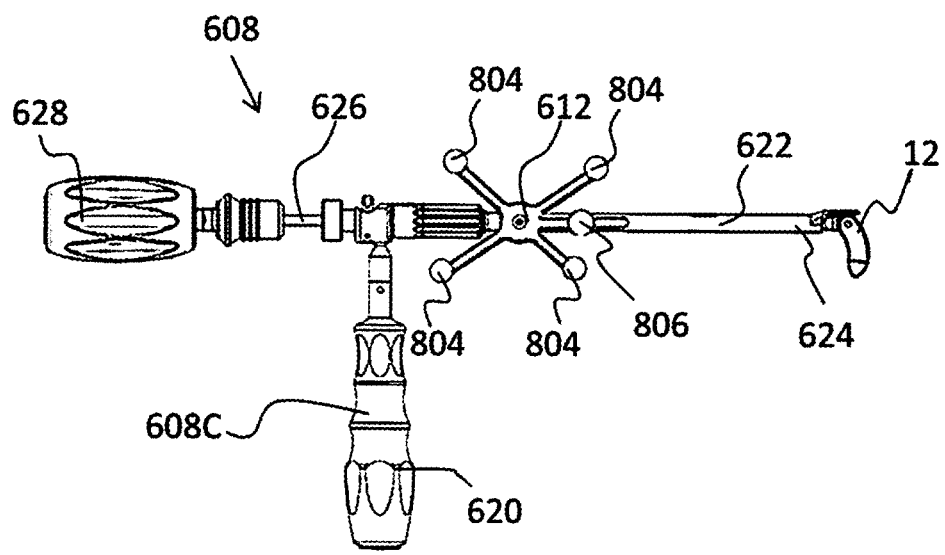

Turning now to FIGS. 18A-18B, four fixed markers 804 are used to define the implant holder 608C and a fifth, moveable marker 806 is configured to slide within a predetermined path to provide feedback on the implant articulation angle. FIG. 18A shows the articulating spacer 12 at its initial linear state, and FIG. 18B shows the spacer 12 in an articulated state at some offset angle with the moveable marker 806 translated to a different position. The amount of linear translation of the marker 806 would correspond to the articulation angle of the implant 12. Although only two positions are shown, it would be possible to have this as a continuous function whereby any given articulation angle could be correlated to a specific position of the moveable marker 806.

In these embodiments, the moveable marker 806 slides continuously to provide feedback about an attribute of the implant 10, 12 based on position. It is also contemplated that there may be discreet positions that the moveable marker 806 must be in which would also be able to provide further information about an implant attribute. In this case, each discreet configuration of all markers 804, 806 correlates to a specific geometry of the implant holder 608B, 608C and the implant 10, 12 in a specific orientation or at a specific height. In addition, any motion of the moveable marker 806 could be used for other variable attributes of any other type of navigated implant.

Although depicted and described with respect to linear movement of the moveable marker 806, the moveable marker 806 should not be limited to just sliding as there may be applications where rotation of the marker 806 or other movements could be useful to provide information about the implant 10, 12. Any relative change in position between the set of fixed markers 804 and the moveable marker 806 could be relevant information for the implant 10, 12 or other device. In addition, although expandable and articulating implants 10, 12 are exemplified, the instrument 608 could work with other medical devices and materials, such as spacers, cages, plates, fasteners, nails, screws, rods, pins, wire structures, sutures, anchor clips, staples, stents, bone grafts, biologics, cements, or the like.

Figure 19A:
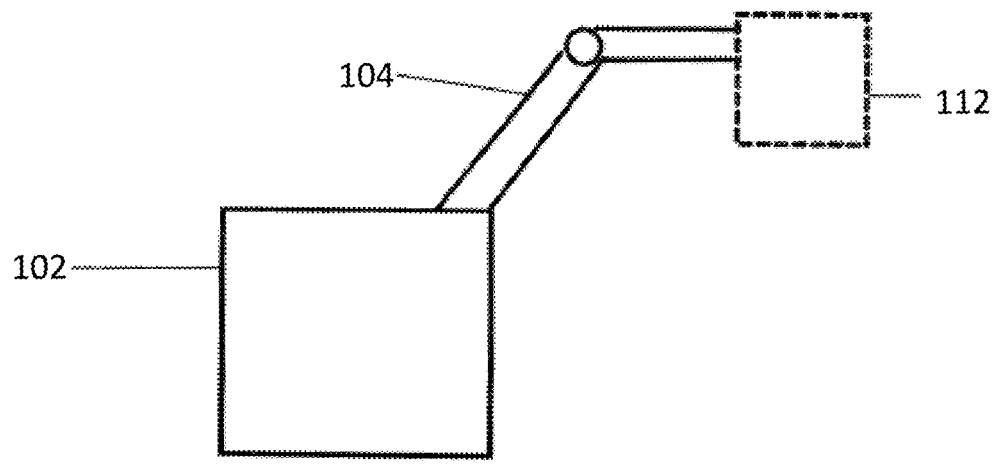
FIG. 19A depicts an embodiment of a robot with interchangeable or alternative end-effectors.

Turning now to FIG. 19A, it is envisioned that the robot end-effector 112 is interchangeable with other types of end-effectors 112. Moreover, it is contemplated that each end-effector 112 may be able to perform one or more functions based on a desired surgical procedure. For example, the end-effector 112 having a guide tube 114 may be used for guiding an instrument 608 as described herein. In addition, end-effector 112 may be replaced with a different or alternative end-effector 112 that controls a surgical device, instrument, or implant, for example.

The alternative end-effector 112 may include one or more devices or instruments coupled to and controllable by the robot. By way of non-limiting example, the end-effector 112, as depicted in FIG. 19A, may comprise a retractor (for example, one or more retractors disclosed in U.S. Pat. Nos. 8,992,425 and 8,968,363) or one or more mechanisms for inserting or installing surgical devices such as expandable intervertebral fusion devices (such as expandable implants exemplified in U.S. Pat. Nos. 8,845,734; 9,510,954; and 9,456,903), stand-alone intervertebral fusion devices (such as implants exemplified in U.S. Pat. Nos. 9,364,343 and 9,480,579), expandable corpectomy devices (such as corpectomy implants exemplified in U.S. Pat. Nos. 9,393,128 and 9,173,747), articulating spacers (such as implants exemplified in U.S. Pat. No. 9,259,327), facet prostheses (such as devices exemplified in U.S. Pat. No. 9,539,031), laminoplasty devices (such as devices exemplified in U.S. Pat. No. 9,486,253), spinous process spacers (such as implants exemplified in U.S. Pat. No. 9,592,082), inflatables, fasteners including polyaxial screws, uniplanar screws, pedicle screws, posted screws, and the like, bone fixation plates, rod constructs and revision devices (such as devices exemplified in U.S. Pat. No. 8,882,803), artificial and natural discs, motion preserving devices and implants, spinal cord stimulators (such as devices exemplified in U.S. Pat. No. 9,440,076), and other surgical devices. The end-effector 112 may include one or instruments directly or indirectly coupled to the robot for providing bone cement, bone grafts, living cells, pharmaceuticals, or other deliverable to a surgical target. The end-effector 112 may also include one or more instruments designed for performing a discectomy, kyphoplasty, vertebrostenting, dilation, or other surgical procedure.

The end-effector itself and/or the implant, device, or instrument may include one or more markers 118 such that the location and position of the markers 118 may be identified in three-dimensions. It is contemplated that the markers 118 may include active or passive markers 118, as described herein, that may be directly or indirectly visible to the cameras 200. Thus, one or more markers 118 located on an implant 10, for example, may provide for tracking of the implant 10 before, during, and after implantation.

Figure 19B:
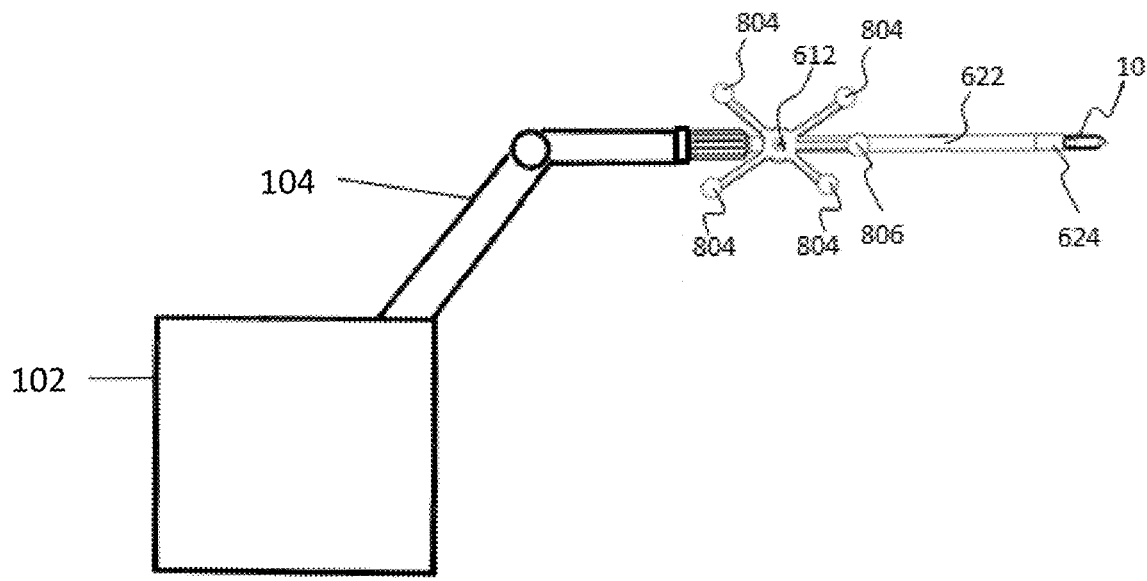
FIG. 19B depicts an embodiment of a robot with an instrument style end-effector coupled thereto.

As shown in FIG. 19B, the end-effector 112 may include an instrument 608 or portion thereof that is coupled to the robot arm 104 (for example, the instrument 608 may be coupled to the robot arm 104 by the coupling mechanism shown in FIGS. 9A-9C) and is controllable by the robot system 100. Thus, in the embodiment shown in FIG. 19B, the robot system 100 is able to insert implant 10 into a patient and expand or contract the expandable implant 10. Accordingly, the robot system 100 may be configured to assist a surgeon or to operate partially or completely independently thereof. Thus, it is envisioned that the robot system 100 may be capable of controlling each alternative end-effector 112 for its specified function or surgical procedure.

Although the robot and associated systems described herein are generally described with reference to spine applications, it is also contemplated that the robot system is configured for use in other surgical applications, including but not limited to, surgeries in trauma or other orthopedic applications (such as the placement of intramedullary nails, plates, and the like), cranial, neuro, cardiothoracic, vascular, colorectal, oncological, dental, and other surgical operations and procedures.

Figure 20:
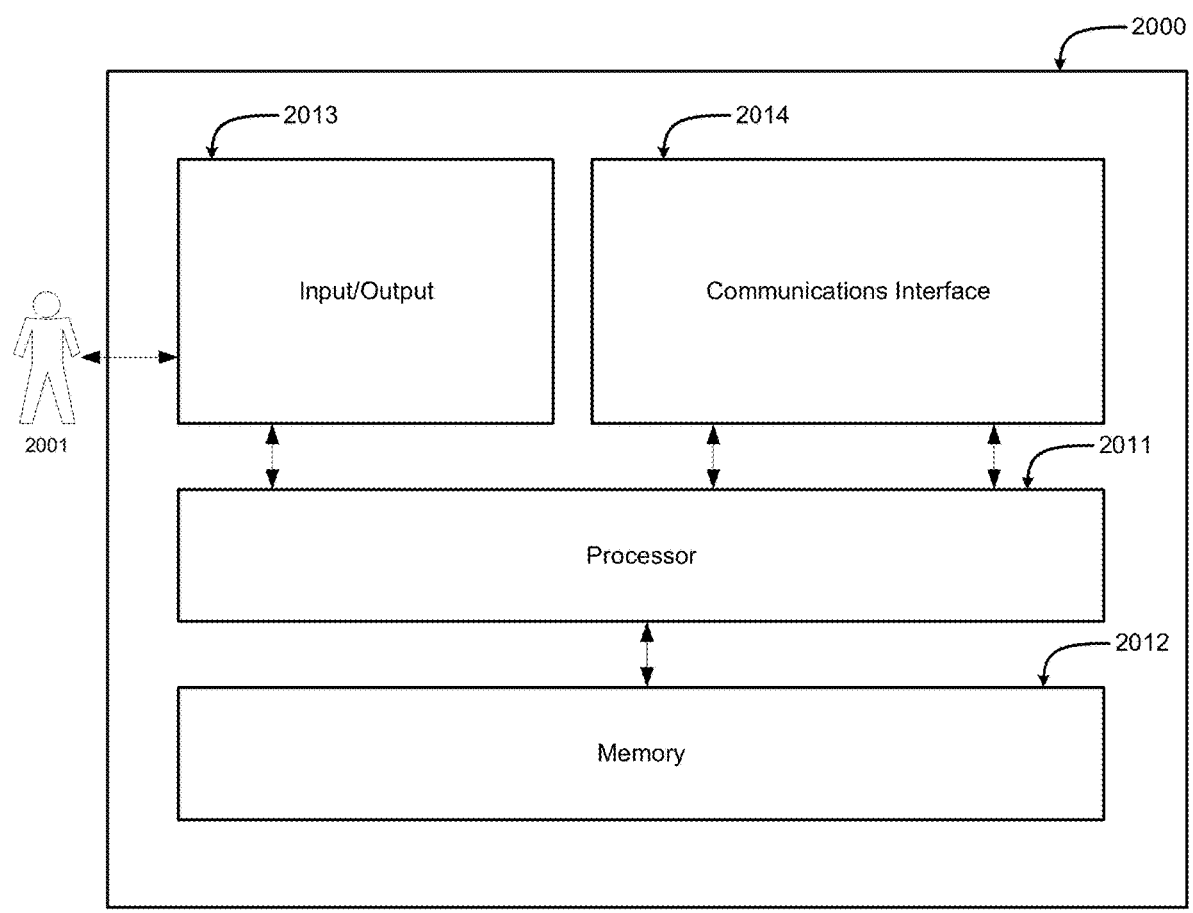
FIG. 20 is a functional block diagram of an example computing device that may be used in the environments described herein.

FIG. 20 is a functional block diagram of an example computing device 2000 that may be used in the environments described herein. Specifically, computing device 2000 illustrates an exemplary configuration of a computing device. Computing device 2000 illustrates an exemplary configuration of a computing device operated by a user 2001 in accordance with one embodiment of the present invention. Computing device 2000 may include, but is not limited to, a surgical navigation computing device, an imaging computing device in communication with an imaging device, a surgical robotic computing device, and any other suitable device. Computing device 2000 may also include mobile computing devices, stationary computing devices, computing peripheral devices, smart phones, wearable computing devices, medical computing devices, vehicular computing devices, end user computing devices, tablets, terminals, and health care provider end user devices. Alternatively, computing device 2000 may be any computing device capable of performing the event processing methods for providing resilient message processing using asynchronous communications described herein. In some variations, the characteristics of the described components may be more or less advanced, primitive, or non-functional.

In the exemplary embodiment, computing device 2000 includes a processor 2011 for executing instructions. In some embodiments, executable instructions are stored in a memory area 2012. Processor 2011 may include one or more processing units, for example, a multi-core configuration. Memory area 2012 is any device allowing information such as executable instructions and/or written works to be stored and retrieved. Memory area 2012 may include one or more computer readable media.

Computing device 2000 also includes at least one input/output component 2013 for receiving information from and providing information to user 2001. In some examples, input/output component 2013 may be of limited functionality or non-functional as in the case of some wearable computing devices. In other examples, input/output component 2013 is any component capable of conveying information to or receiving information from user 2001. In some embodiments, input/output component 2013 includes an output adapter such as a video adapter and/or an audio adapter. Input/output component 2013 may alternatively include an output device such as a display device, a liquid crystal display (LCD), organic light emitting diode (OLED) display, or "electronic ink" display, or an audio output device, a speaker or headphones. Input/output component 2013 may also include any devices, modules, or structures for receiving input from user 2001. Input/output component 2013 may therefore include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output and input device of input/output component 2013. Input/output component 2013 may further include multiple sub-components for carrying out input and output functions.

Computing device 2000 may also include a communications interface 2014, which may be communicatively coupleable to a remote device such as a remote computing device, a remote server, or any other suitable system. Communication interface 414 may include, for example, a wired or wireless network adapter or a wireless data transceiver for use with a mobile phone network, Global System for Mobile communications (GSM), 3G, 4G, or other mobile data network or Worldwide Interoperability for Microwave Access (WIMAX). Communications interface 2014 is configured to allow computing device 2000 to interface with any other computing device or network using an appropriate wireless or wired communications protocol such as, without limitation, BLUETOOTH®, Ethernet, or IEEE 802.11. Communications interface 2014 allows computing device 2000 to communicate with any other computing devices with which it is in communication or connection.

Figure 21:
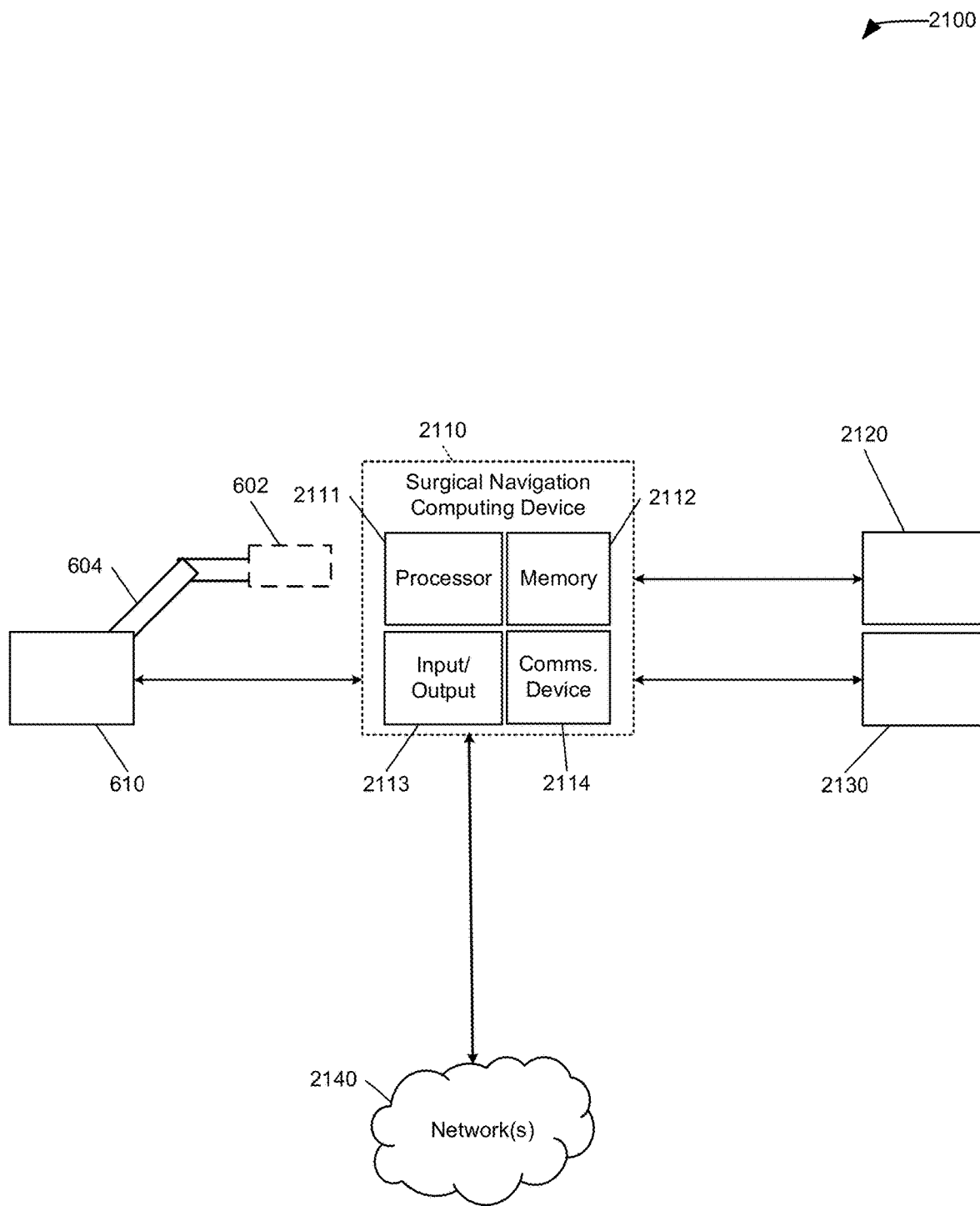
FIG. 21 is a functional block diagram of a surgical navigation system including multiple computing devices shown in FIG. 20.

FIG. 21 is a functional block diagram of a surgical navigation system 2100 including multiple computing devices similar to computing device 2000 (shown in FIG. 2000). As described herein, surgical navigation system 2100 is provided for defining and implementing a surgical navigation plan to correct a deformed spinal alignment. In an example embodiment, surgical navigation system includes surgical navigation computing device 2110 which further includes processor 2111, memory area 2112, input/output 2113, and communications device 2114. In some embodiments, surgical navigation computing device 2110 includes, is integrated with, and/or is in communication with other devices including imaging device(s) 2120, surgical instrument sensor(s) 2130 (e.g., strain gauges). In several embodiments, surgical navigation computing device 2110 is also in communication with surgical robot 600 (as described in FIG. 6). Surgical robot system 600 may comprise end-effector 602, robot arm 604, guide tube (not shown in FIG. 21), instrument (not shown in FIG. 21), and robot base 610. As described herein, surgical robot 600 may be integrated within surgical navigation system 2100, may functionally integrate with surgical navigation computing device 2110, and both systems may functionally integrate with imaging device(s) 2120. In several embodiments, the devices and systems 2100, 2110, 2120, 2130, and 600 may further interact with external devices including via network 2140.

Figure 22:
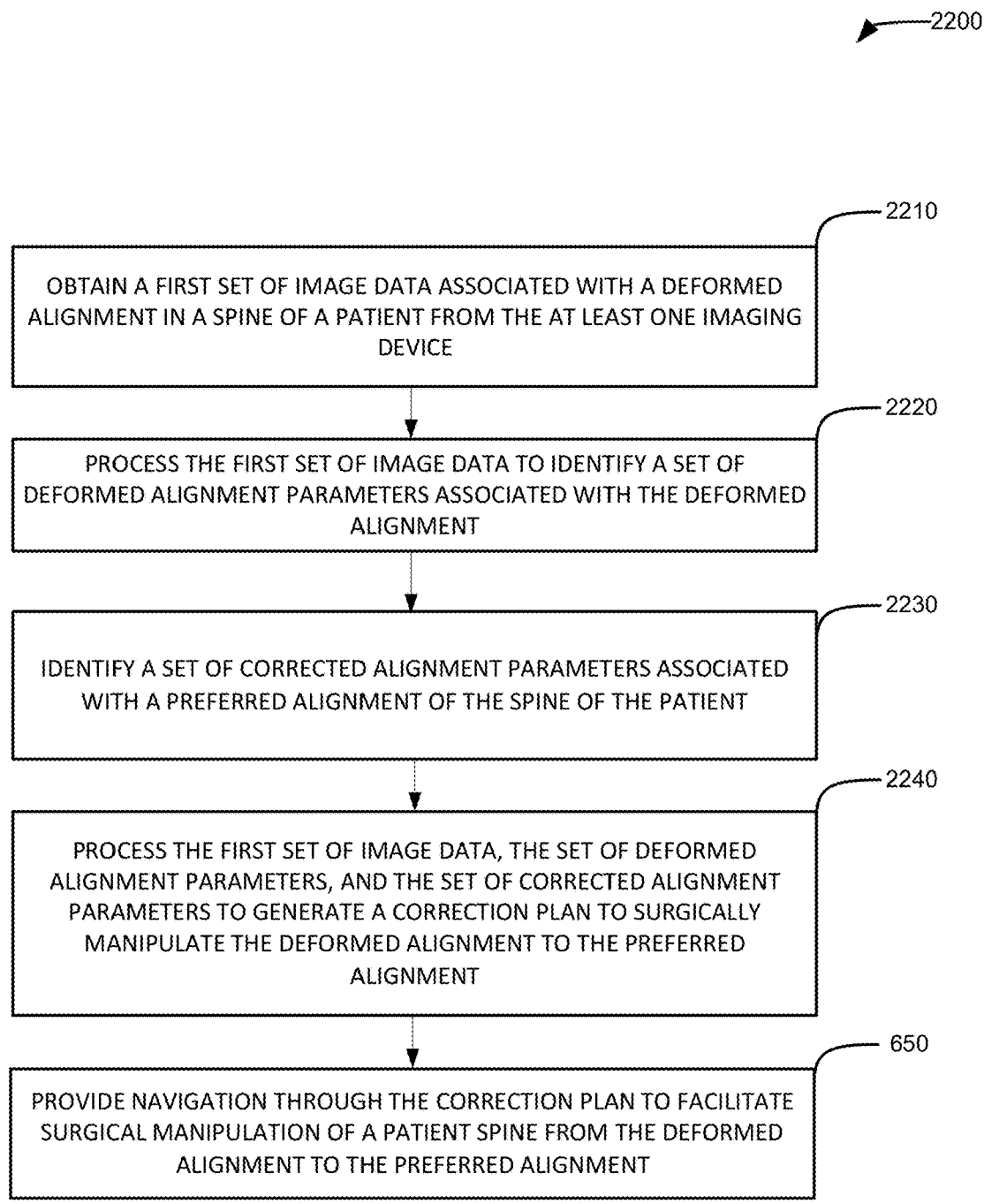
FIG. 22 is a flow diagram representing a method for defining and implementing a surgical navigation plan to correct a deformed spinal alignment performed by the surgical navigation computing device of the surgical navigation system shown in FIG. 21.

FIG. 22 is a flow diagram 2200 representing a method for defining and implementing a surgical navigation plan to correct a deformed spinal alignment performed by the surgical navigation computing device 2110 of the surgical navigation system 2100 (shown in FIG. 21). In at least one embodiment, surgical navigation computing device 2110 is configured to obtain 2210 a first set of image data associated with a deformed alignment in a spine of a patient from the at least one imaging device. Surgical navigation computing device 2110 is also configured to process 2220 the first set of image data to identify a set of deformed alignment parameters associated with the deformed alignment. Surgical navigation computing device 2110 is further configured to identify 2230 a set of corrected alignment parameters associated with a preferred alignment of the spine of the patient. Surgical navigation computing device 2110 is also configured to process 2240 the first set of image data, the set of deformed alignment parameters, and the set of corrected alignment parameters to generate a correction plan to surgically manipulate the deformed alignment to the preferred alignment. Surgical navigation computing device 2110 is also configured to provide 2250 navigation through the correction plan to facilitate surgical manipulation of a patient spine from the deformed alignment to the preferred alignment.

Figure 23:
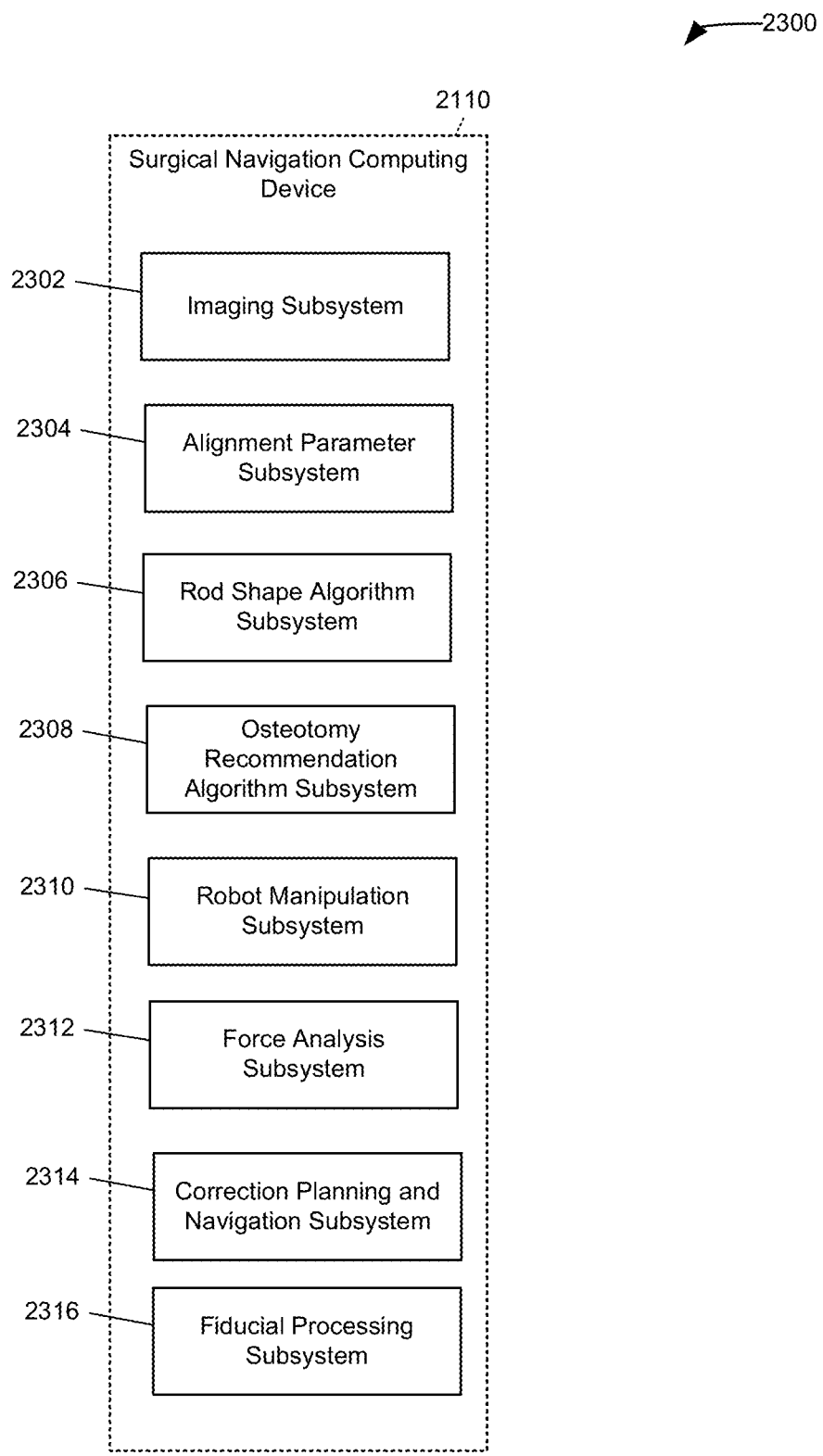
FIG. 23 is a diagram of elements of one or more example computing devices that may be used in the system shown in FIGS. 20-21.

FIG. 23 is a diagram of elements of one or more example computing devices that may be used in the system shown in FIGS. 1-5. As described herein, the elements 2302, 2304, 2306, 2308, 2310, 2312, 2314, and 2316 are configured to perform the processes and methods described herein. Imaging subsystem 2302 is configured to capture, process, obtain, generate and store the images, scans, models, and simulate models and images related to the pre-operative, intra-operative, post-operative, and preferred spinal alignments. As such, imaging subsystem 2302 interacts with and consumes information from imaging device(s) 2120 and may control imaging device(s) 2120 to perform the functions described herein. Alignment parameter subsystem 2304 is configured to obtain values for alignment parameters (or other suitable definitions and descriptions associated with spinal alignment) including but not limited to Cobb angle, lumbar lordosis, thoracic kyphosis, cervical lordosis, axial rotation, sagittal vertical axis, sagittal curve size, pelvic tilt, pelvic incidence, T1 pelvic angle, 3D kyphosis, angle of the plane of maximum kyphosis, measurements for upper end vertebrae ("UEV"), measurements for lower end vertebrae ("LEV"), measurements for upper end instrumented vertebrae ("UIV"), and measurements for lower end instrumented vertebrae ("LIV"). As such alignment parameter subsystem 2304 may calculate or otherwise determine such values or definitions for pre-operative, intra-operative, post-operative, and preferred spinal alignments. Alignment parameter subsystem 2304 may also provide and receive output and input to users and thereby update alignment parameters based on surgeon preferences. Rod shape algorithm subsystem 2306 is configured to provide or otherwise obtain the preferred rod shape for a bent rod in post-surgery use. In one example, the rod shape algorithm functions as follows. The surgical navigation computing device uses the pre-operative and intra-operative image and scan data (and the alignment parameters or definition data derived therefrom) to determine the amount of deflection that will occur to the permanent rod when it is inserted. The algorithm also receives information regarding the size, shape, material composition, and properties of the rod. (Such information may be provided by a manufacturer definition file or a user.) The data regarding the amount of deflection and the rod are used to determine the optimal, ideal, or preferred rod shape will take into consideration the size and material properties of the rod. In some examples, the algorithm also incorporates other variables that may influence preferred rod bend including spinal balance, and patient height, patient weight, and patient bone density.

The osteotomy recommendation algorithm subsystem 2308 is configured to processes orientation and location data along with force data from sensors to determine preferred locations and extents (or sizes) of osteotomies. In some examples, the touchscreen user interface presents proposed osteotomies identified by the osteotomy algorithm. The robot manipulation subsystem 2310 provides the interface between the surgical navigation computing device 2110 and the surgical robot 600 (both shown in FIG. 21) and allows the surgical robot 600 to perform steps described herein. The force analysis subsystem 2312 processes force and stress information identified by the system from sensors such as sensors 2130 (shown in FIG. 21) to determine magnitude, direction, and location of forces acting on the spine or surgical devices. Force analysis subsystem 2312 is therefore used in several aspects of the systems described including identifying recommended osteotomy locations and extents, defining preferred rod bends, and identifying corrective loads. Correction planning and navigation subsystem 2314 is used to define correction plans based at least on the first set of image data, the set of deformed alignment parameters, and the set of corrected alignment parameters. Fiducial processing subsystem 2316 is used to identify, process, and analyze fiducial locations with respect to attached surgical devices, and to identify absolute locations and orientations and relative locations and orientations for fiducials and surgical devices.

FIG. 24 illustrates rod link reducer instrumentation 2410 and 2420 including temporary rods and fiducial markers. Fiducial markers 2413, 2414, 2423, and 2424 are placed on the temporary rods 2412 and 2422 according to one embodiment of the invention. Each of the rod link reducer instrumentation 2410 and 2420 includes an associated manipulating arm 2411 and 2421 for use in guiding or navigating the temporary rod 2412 and 2422 that is attached thereto. Each rod link reducer instrumentation 2410 and 2420 is attached with screws 2417, 2418, 2419 and 2427, 2428, and 2429. In one example, for each of rod link reducer instrumentation 2410 and 2420, two fiducial markers 2413, 2414, 2423, and 2424 are placed on opposing ends of each of the temporary rods 2412 and 2422. In operation, in some examples an additional fiducial marker is placed on the spinous process of the vertebrae at the apex of the deformity (not shown). The two fiducial markers 2413 and 2414 and 2423 and 2424 on each temporary rod 2412 and 2422 may be tracked to create a line segment at the proximal and distal ends of the deformity. The orientation of the line segments with respect to one another gives a visual representation of the magnitude of the curve in the coronal plane. The line segments may be used to display measurements of applicable spinal parameters such as coronal Cobb angle. Similarly, the fiducial markers 2413 and 2414 and 2423 and 2424 may be used to determine a visual representation of the spinal alignment in the sagittal and axial planes that may be presented on a user interface.

The fiducial markers 2413, 2414, 2423, and 2424 may be attached to the temporary rods with unique clamping instruments 2415 and 2425. In another embodiment, the fiducial markers may be attached to the manipulating arms, to the coupling rod, or to any other suitable apparatus within the system.

FIG. 25 illustrates a locking cap system 2500 with integrated fiducial markers according to one embodiment of the invention. In such an embodiment, a clamping system 2501 secures a temporary rod 2510 using a clamp 2502. The locking cap system 2500 further includes fiducial markers 2511, 2521, and 2531 that are integrated with or engage with locking caps 2512, 2522, and 2532 to secure temporary rod 2510. Locking cap system 2500 also includes screws 2513, 2523, and 2533 to secure the apparatus in operation.

Additional fiducial markers could be placed on the vertebral segments at the apex of the deformity in order to track motion of the entire spine. These fiducial markers could be secured directly to the anatomy via specialized clamping mechanisms or indirectly by attaching to pedicle screws.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. It is further envisioned that features from one embodiment may be combined or used with the features from a different embodiment described herein. Moreover, although specific terms are employed herein, as well as in the claims which follow, they are used only in a generic and descriptive sense, and not for the purposes of limiting the described invention, nor the claims which follow. The entire disclosure of each patent and publication cited herein is incorporated by reference in its entirety, as if each such patent or publication were individually incorporated by reference herein. Various features and advantages of the invention are set forth in the following claims.

What is claimed is:

1. A surgical navigation system for defining and implementing a surgical navigation plan to correct a deformed spinal alignment, comprising:
at least one imaging device configured to capture image data;
a surgical navigation computing device in communication with the at least one imaging device, said surgical navigation computing device comprising a processor and a memory, said processor is configured to:

obtain a first set of image data associated with a deformed alignment in a spine of a patient from the at least one imaging device;

process the first set of image data to identify a set of deformed alignment parameters associated with the deformed alignment;

identify a set of corrected alignment parameters associated with a preferred alignment of the spine of the patient;

process the first set of image data, the set of deformed alignment parameters, and the set of corrected alignment parameters to generate a correction plan to surgically manipulate the deformed alignment to the preferred alignment; and provide navigation through the correction plan to facilitate surgical manipulation of a patient spine from the deformed alignment to the preferred alignment; and a strain gauge sensor attached to a rod link reducer, wherein the rod link reducer is applied to manipulate the patient spine from the deformed alignment to the preferred alignment, wherein the strain gauge sensor is in communication with the surgical navigation computing device.

2. The surgical navigation system of claim 1, further comprising a surgical robot in communication with the surgical navigation computing device, wherein the processor is further configured to:

cause the surgical robot to apply the correction plan to surgically manipulate the patient spine from the deformed alignment to the preferred alignment.

3. The surgical navigation system of claim 2, wherein the processor is further configured to:

obtain feedback from the surgical robot describing the movement of the surgical robot;

identify a planned movement of the surgical robot based on the correction plan;

compare the feedback to the planned movement to identify deviations in the robot movement from the correction plan; and transmit an alert when a deviation from the correction plan is identified.

4. The surgical navigation system of claim 1, wherein the processor is further configured to:

obtain a second set of image data associated with an intra-operative spinal alignment in a patient during surgery from the at least one imaging device;

identify a planned intra-operative spinal movement based on the correction plan;

process the second set of image data and the planned intra-operative spinal movement to identify deviations from the correction plan; and transmit an alert when a deviation from the correction plan is identified.

5. The surgical navigation system of claim 1, wherein the processor is further configured to:

obtain feedback from the strain gauge sensor;

process the correction plan to identify an acceptable range of strain on the rod link reducer; and transmit an alert when the feedback exceeds the acceptable range of strain.

6. The surgical navigation system of claim 1, wherein the processor is further configured to:

obtain feedback from the strain gauge sensor identifying strain forces acting on the spine; and process the feedback and the correction plan to identify a preferred bend of a permanent rod, wherein a permanent rod with the preferred bend is configured to maintain a form resistant to the identified strain forces.

7. The surgical navigation system of claim 6, further comprising a rod bending machine in communication with the surgical navigation computing device, wherein the processor is further configured to instruct the rod bending device to bend a first permanent rod to the shape of the preferred bend.

8. The surgical navigation system of claim 1, wherein the processor is further configured to:

obtain feedback from the strain gauge sensor identifying forces acting on the spine;

analyze the feedback and the correction plan to anticipated forces acting on a pedicle screw used in the surgical manipulation of the patient spine;

determine that the anticipated forces exceed a threshold defining a risk of pull out or plowing by the pedicle screw;

identify at least one osteotomy plan to mitigate the anticipated forces to below the threshold, wherein the osteotomy plan includes at least an osteotomy location and an osteotomy depth; and update the correction plan with the at least one osteotomy plan.

9. The surgical navigation system of claim 1 further comprising a surgical robot in communication with the surgical navigation computing device, wherein the processor is further configured to:

instruct the surgical robot to the apply the correction plan by controlling and manipulating the rod link reducer to manipulate the patient spine from the deformed alignment to the preferred alignment.

10. The surgical navigation system of claim 1, wherein the processor is further configured to:

obtain a second set of image data associated with an intra-operative spinal alignment in a patient during surgery from the at least one imaging device;

identify a set of pedicle screw placement definitions from the correction plan, the set of pedicle screw placement definitions identifying a preliminary location and orientation for each of an associated set of pedicle screws;

process the second set of image data and the correction plan to identify anticipated corrective loads on each of the associated set of pedicle screws;

revise the set of pedicle screw placement definitions for each of the associated set of pedicle screws, based in part on the anticipated corrective loads; and update the correction plan with the revised set of pedicle screw placement definitions.

11. The surgical navigation system of claim 1, wherein the processor is further configured to:

identify an associated fiducial marker attached to each of a plurality of surgical devices used to manipulate the patient spine from the deformed alignment to the preferred alignment, wherein each associated fiducial marker has a fixed spatial relationship to the respective surgical device;

obtain a second set of image data associated with an intra-operative spinal alignment in a patient during surgery from the at least one imaging device; and process the second set of image data to identify a set of position information for each of the plurality of surgical devices based at least in part on the associated fiducial marker, wherein each of the set position information includes location information and orientation information.

12. The surgical navigation system of claim 11, wherein the processor is further configured to:
- identify an expected navigation plan for each of the plurality of surgical devices from the correction plan;
- process the expected navigation plans and the set of position information to identify deviations from the navigation plans; and
- transmit an alert when a deviation from each of the navigation plans is identified.

13. A method for defining and implementing a surgical navigation plan to correct a deformed spinal alignment, said method is performed by a surgical navigation computing device in communication with at least one imaging device, the surgical navigation computing device including a processor and a memory, said method including:
- obtaining a first set of image data associated with a deformed alignment in a spine of a patient from the at least one imaging device;
- processing the first set of image data to identify a set of deformed alignment parameters associated with the deformed alignment;
- identifying a set of corrected alignment parameters associated with a preferred alignment of the spine of the patient;
- processing the first set of image data, the set of deformed alignment parameters, and the set of corrected alignment parameters to generate a correction plan to surgically manipulate the deformed alignment to the preferred alignment; and
- providing navigation through the correction plan to facilitate surgical manipulation of a patient spine from the deformed alignment to the preferred alignment,
- wherein the surgical navigation computing device is in communication with a strain gauge sensor attached to a rod link reducer, wherein the rod link reducer is applied to manipulate the patient spine from the deformed alignment to the preferred alignment.

14. The method of claim 13, further comprising:
- obtaining a second set of image data associated with an intra-operative spinal alignment in a patient during surgery from the at least one imaging device;
- identifying a planned intra-operative spinal movement based on the correction plan;
- processing the second set of image data and the planned intra-operative spinal movement to identify deviations from the correction plan; and
- transmitting an alert when a deviation from the correction plan is identified.

15. The method of claim 13, further comprising:
- obtaining feedback from the strain gauge sensor;
- processing the correction plan to identify an acceptable range of strain on the rod link reducer; and
- transmitting an alert when the feedback exceeds the acceptable range of strain.

16. The method of claim 13, further comprising:
- obtaining feedback from the strain gauge sensor identifying strain forces acting on the spine; and
- processing the feedback and the correction plan to identify a preferred bend of a permanent rod, wherein a permanent rod with the preferred bend is configured to maintain a form resistant to the identified strain forces.

17. The method of claim 13, further comprising:
- obtaining a second set of image data associated with an intra-operative spinal alignment in a patient during surgery from the at least one imaging device;
- identifying a set of pedicle screw placement definitions from the correction plan, the set of pedicle screw placement definitions identifying a preliminary location and orientation for each of an associated set of pedicle screws;
- processing the second set of image data and the correction plan to identify anticipated corrective loads on each of the associated set of pedicle screws;
- revising the set of pedicle screw placement definitions for each of the associated set of pedicle screws, based in part on the anticipated corrective loads; and
- updating the correction plan with the revised set of pedicle screw placement definitions.

18. A surgical navigation computing device for defining and implementing a surgical navigation plan to correct a deformed spinal alignment, said surgical navigation computing device in communication with at least one imaging device, said surgical navigation computing device comprising a processor and a memory, said processor is configured to:
- obtain a first set of image data associated with a deformed alignment in a spine of a patient from the at least one imaging device;
- process the first set of image data to identify a set of deformed alignment parameters associated with the deformed alignment;
- identify a set of corrected alignment parameters associated with a preferred alignment of the spine of the patient;
- process the first set of image data, the set of deformed alignment parameters, and the set of corrected alignment parameters to generate a correction plan to surgically manipulate the deformed alignment to the preferred alignment; and
- provide navigation through the correction plan to facilitate surgical manipulation of a patient spine from the deformed alignment to the preferred alignment,
- wherein the surgical navigation computing device is in communication with a strain gauge sensor attached to a rod link reducer, wherein the rod link reducer is applied to manipulate the patient spine from the deformed alignment to the preferred alignment.

* * * * *